(12) United States Patent
Qu

(10) Patent No.: US 11,226,314 B2
(45) Date of Patent: Jan. 18, 2022

(54) REFLECTION-DIFFRACTION-DEFORMATION FLAW DETECTION METHOD WITH TRANSVERSE WAVE OBLIQUE PROBE

(71) Applicant: TEWARE, INC., Liaoning (CN)

(72) Inventor: Shifa Qu, Liaoning (CN)

(73) Assignee: TEWARE, INC., Liaoning (CN)

(*) Notice: Subject to any disclaimer, the term of this patent is extended or adjusted under 35 U.S.C. 154(b) by 113 days.

(21) Appl. No.: 16/637,390

(22) PCT Filed: Aug. 7, 2018

(86) PCT No.: PCT/CN2018/099171
§ 371 (c)(1),
(2) Date: Feb. 7, 2020

(87) PCT Pub. No.: WO2019/029524
PCT Pub. Date: Feb. 14, 2019

(65) Prior Publication Data
US 2021/0116422 A1  Apr. 22, 2021

(30) Foreign Application Priority Data

Aug. 10, 2017 (CN) .......................... 201710680381.6
Aug. 1, 2018 (CN) .......................... 201810860988.7

(51) Int. Cl.
*G01N 33/207* (2019.01)
*G01N 29/04* (2006.01)
(Continued)

(52) U.S. Cl.
CPC ....... *G01N 29/4445* (2013.01); *G01N 29/043* (2013.01); *G01N 29/2487* (2013.01);
(Continued)

(58) Field of Classification Search
CPC ........... G01N 29/2487; G01N 29/4454; G01N 29/30; G01N 29/069; G01N 29/343;
(Continued)

(56) References Cited

U.S. PATENT DOCUMENTS 4,570,487 A * 2/1986 Gruber ................. G01N 29/043
73/624
6,813,950 B2 * 11/2004 Glascock ............. G01N 29/221
73/622
(Continued)

FOREIGN PATENT DOCUMENTS

| | | | |
|---|---|---|---|
| CN | 101454663 A | 6/2009 | |
| CN | 101839895 A | 9/2010 | |
| CN | 103954687 A | 7/2014 | |
| CN | 107505394 A | 12/2017 | |
| JP | 09033490 A * | 2/1997 | ............. G01N 29/00 |

*Primary Examiner* — Jacques M Saint Surin
(74) *Attorney, Agent, or Firm* — Novick, Kim & Lee, PLLC; Allen Xue

(57) ABSTRACT

A reflection-diffraction-deformation flaw detection method employs a transverse wave oblique probe. When an ultrasonic transverse wave encounters a defect during propagation, a reflected wave, a diffracted wave, and a deformed wave are generated. Through a comprehensive analysis of these waves, the presence or absence of the defect is determined by the reflected wave having reflection characteristics and the diffracted wave having the diffraction characteristics. The shape and size of the defect are determined by the deformed wave having deformation characteristics, namely the deformed surface wave generated at the endpoints of the defect which propagates on the defect surface. Furthermore, by the combination of paths trailed by the deformed surface wave, the deformed transverse wave, and the deformed longitudinal wave that are generated by the defect as well as that trailed by the transmit transverse wave, causes of all those waves in the screen can be revealed.

8 Claims, 30 Drawing Sheets

(51) Int. Cl.
 *G01N 29/24* (2006.01)
 *G01N 29/44* (2006.01)
(52) U.S. Cl.
 CPC ... *G01N 33/207* (2019.01); *G01N 2291/0289* (2013.01); *G01N 2291/0422* (2013.01); *G01N 2291/056* (2013.01); *G01N 2291/267* (2013.01)
(58) Field of Classification Search
 CPC ....... G01N 29/4445; G01N 2291/0422; G01N 2291/267; G01N 2291/056; G01N 2291/0289; G01N 2291/044
 USPC .......................................................... 73/588
 See application file for complete search history.

(56) References Cited

U.S. PATENT DOCUMENTS

| | | | | |
|---|---|---|---|---|
| 7,900,516 | B2* | 3/2011 | Fukutomi | G01N 29/2487 73/598 |
| 8,100,014 | B2* | 1/2012 | Fukutomi | G01N 29/069 73/598 |
| 9,207,214 | B2* | 12/2015 | S | G01N 29/04 |
| 9,423,380 | B2* | 8/2016 | Mizota | G01N 29/069 |
| 9,625,424 | B2* | 4/2017 | LePage | G01N 29/262 |
| 10,712,317 | B2* | 7/2020 | Shin | G01N 29/2487 |
| 2005/0110988 | A1* | 5/2005 | Nishiyama | G01N 21/95684 356/237.5 |
| 2008/0151259 | A1* | 6/2008 | Yoo | G01N 21/9501 356/521 |
| 2014/0333923 | A1* | 11/2014 | Taniguchi | G01N 21/95684 356/237.5 |

* cited by examiner

REFLECTION-DIFFRACTION-DEFORMATION FLAW DETECTION METHOD WITH TRANSVERSE WAVE OBLIQUE PROBE

CROSS-REFERENCE TO RELATED APPLICATIONS

This application is a U.S. National Phase application of International Patent Application number PCT/CN2018/099171 filed on Aug. 7, 2018, entitled "SHEAR WAVE OBLIQUE PROBE REFLECTED/DIFFRACTED/DEFORMED WAVE DETECTION METHOD", which claims the benefit of and priority to China Patent Application No. 201710680381.6, entitled "ULTRASONIC SHEAR WAVE OBLIQUE PROBE REFLECTED/DIFFRACTED/DEFORMED WAVE DETECTION METHOD" and filed Aug. 10, 2017, and the benefit of and priority to China Patent Application No. 201810860988.7, entitled "SHEAR WAVE OBLIQUE PROBE REFLECTED/DIFFRACTED/DEFORMED WAVE DETECTION METHOD" and filed Aug. 1, 2018, before China National Intellectual Property Administration of People's Republic of China, disclosures of all of which are incorporated herein by reference in their entireties.

TECHNICAL FIELD

The present disclosure relates to the technical field of flaw detection, and more particularly relates to a reflection-diffraction-deformation flaw detection method with a transverse wave oblique probe.

BACKGROUND

The existing Amplitude-mode (A-mode) pulse ultrasonic flaw detection technology can be simply explained as follows. An ultrasonic flaw detection instrument emits ultrasonic waves through an ultrasonic probe, and the ultrasonic waves enter the workpiece under inspection at a specified angle. During their propagation, the ultrasonic waves may encounter a heterogeneous interface (a flaw) and then reflect. The reflected ultrasonic waves partially return along the same original path and are reflected in the form of pulses on a screen of the instrument. As such, the flaw or defect can be located, and quantitatively and qualitatively analyzed based on the location where the reflected pulses show up as well as the height and shape of the reflected pulses. As shown in FIGS. 1-1 through 1-4, FIG. 1-1 is a schematic diagram illustrating the flaw detection with a longitudinal wave normal probe, FIG. 1-2 is a schematic diagram illustrating the flaw detection with a longitudinal wave oblique probe, FIG. 1-3 is a schematic diagram illustrating the flaw detection with a transverse wave oblique probe, and FIG. 1-4 is a schematic diagram illustrating the flaw detection with a surface wave probe.

The current A-ultrasound technology bases on waves reflected from a defect in order to locate, characterize, and quantify the defect. The first goal is to maximize the reflected echo from the defect, where the reflected echo is the highest only when the sound beam poses perpendicular to the defect surface. However, the shape of the defect in the weld is unknown. Only a defect on a groove bevel surface of the weld is known, because the bevel angle is known. FIG. 2 is a schematic diagram illustrating a weld groove.

Since the emergence of the welding technology, the weld groove bevel angle has finally been basically determined, through a large number of experiments and practices, that a thin plate is 20°, a medium thick plate is 30°, and a thick plate is 45°. Only when the bevel angle plus the probe refraction angle β is equal to 90°, the sound beam is perpendicular to the bevel surface, and the defect reflection on the groove bevel surface reaches its largest, as illustrated in FIG. 3, where there is shown a schematic diagram illustrating the derivation of the probe angle.

Therefore, with respect to the weld groove bevel angles established by the welding technique at the time, there came up probes with three refraction angles of 45°, 60°, and 70°. In addition, the A-ultrasound flaw detection technology we used is based on a manually made standard reference object, which is also called a sensitivity test block. A corresponding reflected wave height is obtained on the sensitivity test block, which is the initial sensitivity of the flaw detection. As shown in FIGS. 4-1 and 4-2, FIG. 4-1 show a schematic diagram of a lateral through hole sensitivity test block, and FIG. 4-2 shows a schematic diagram of a flat bottom hole sensitivity test block.

When flaw detection is performed according to this sensitivity, the capability of detecting the defect would vary due to the different sizes or shapes of the reference reflector. The reference reflector for flaw detection determines the sensitivity of the flaw detection. The question comes as which, among the different ultrasonic flaw detection initial sensitivities (including lateral through holes, flat bottom holes, rectangular grooves, etc.), is closer to the accurate flaw detection results? None.

Defects in the weld come in different types, shapes, sizes, positions, and orientations. And they are neither visible nor touchable. The ultrasonic wave reflection method cannot accurately determine the five differences; it can only compare these five differences against a same specified standard transverse through hole or flat bottom hole, etc., under the same sensitivity, for a wave height comparison. Such comparison, however, cannot determine the five differences of the defect; it at best regards the defect as an equivalent of the transverse through hole or the flat bottom hole. Such comparison method is referred to as the equivalent method. The question is can this comparison be able to show that the transverse through hole, the flat bottom hole, and the defect with the same reflected wave height have the same influence the on the weld strength? No, it cannot.

There are currently three equivalent methods in use—one is the equivalent test block comparison method, the second is the equivalent calculation method, and the third is the equivalent AVG curve method. At present, transverse wave flaw detection mainly uses the equivalent test block method. The equivalent defect is merely the defect found at the position where the probe is located. So when the size of the defect in the workpiece is larger than the sound beam interface, then the length of the defect needs to be measured. The length measurement method consists in determining the size of the defect based on the wave height of the defect and the moving distance of the probe. The length measurement methods are divided into relative sensitivity method, absolute sensitivity method, and endpoint peak value method.

If the same defect is measured with different methods mentioned above, there would be different results. The results will also be different with probes at different angles. As such, so many different length measurement methods will lead to confusion in length measurement. Which means a short defect may be measured as a long one, while a long defect may be measured as a short one. Using the above methods to measure the length, the result can only be called the indicated length, not the actual length of the defect.

In current flaw detection, the characterization of the defect is overall determined mainly based on the size of the defect equivalent, the location of the defect, the waveform reflected by the defect, the welding process, the material of the workpiece under inspection, the equipment used for the flaw detection, and the experience of the flaw detector. These however are insufficient to characterize the nature of the defect.

At present, regarding the positioning of the defect, the location of the defect is mainly determined by the position corresponding to the highest point of the reflected wave. However, the highest point of the defect's reflected wave is merely a certain part of the defect itself. The highest point of the defect's reflected wave may be the upper part of the defect, the middle part of the defect, or the lower part of the defect.

In current A-mode pulse ultrasonic flaw detection technology, the size of the defect is an equivalent, the measured length of the defect is an indicated length, the location of the defect is determined as a certain point on the defect, such that the nature of the defect is not guaranteed. One who has worked in flaw detection knows that the flaw detection using the reflection method with A-ultrasound cannot determine that the reflected echo is the reflected echo of the largest surface of the defect. In the current flaw detection method, the fact is present that a large defect may return a small reflected echo, a small defect may return a large reflected echo, a small flaw may be disqualified, or a large defect may be ignored. Reference is made to FIG. 32.

Recent years have seen new progress in ultrasonic flaw detection, and new flaw detection techniques have been born. In the reflection method, ultrasonic phased array scanning technology is emergent, which uses multiple probes at multiple angles for flaw detection. It is essentially an organic arrangement of multiple wafers of a probe. The probe refraction angle can cover 35° to 80° and the ultrasonic waves refracted by these wafers can enter the workpiece simultaneously. Software can be used to individually control the excitation time of each wafer in the phased array probe, so as to control the angle, focus position and focus size of the generated beam, thus completing the inspection and storing the inspection results. Reference is made to FIG. 5, which is a schematic diagram illustrating the principle of electronic focusing and beam deflection realized by an ultrasonic phased array transducer.

This technology falls in the category of A-ultrasonic flaw detection, which more consists in the use of computer technology for the processing, judgement, and storage of the signals captured by the ultrasound. Because the phased array flaw detection technology still employs the principle of the reflection method, the positioning, quantification, and characterization of the defect cannot reflect the true appearance of the defect. For example, the characterization of some defects still relies on experience, and there are still errors in distinguishing defects near the surface of the weld.

In acoustic theory, when an ultrasonic wave propagates through a medium and encounters a heterogeneous interface (defect), according to Huygens' principle, there will be diffraction happening at its edges in addition to generating reflected waves, so that newly excited diffraction waves will be generated. Reference is made to FIG. 6, which shows schematic diagram illustrating the principle of diffraction.

In accordance with this theory, a new ultrasonic diffraction time of flight diffraction method, called TOFD flaw detection technology, is emergent in ultrasonic flaw detection. It uses a pair of wide-sound beam, wide-band unfocused longitudinal wave oblique probes (one wafer per probe), where the probes are respectively arranged on the two opposite sides of the weld, and the flow detection is performed using the one-shot-one-receive mode. The diffraction energy obtained from the "endpoints" and "end corners" of the defect in the weld is used for the detection, quantification and positioning of the defect. However, it only uses the diffraction technique and can only reflect the height of the defect having upper and lower endpoints. Reference is made to FIG. 7, which shows a schematic diagram illustrating the TOFD diffraction technique.

According to acoustic theory, the types of ultrasonic waves include longitudinal waves, transverse waves, plate waves, and surface waves. Each of these waves have capabilities of reflection, diffraction, and deformation. A single wave and a single function in combination cannot reflect the full picture of the defect. For example, the reflection method with the transverse wave including the phased array, and the diffraction method with the longitudinal wave both fail to reflect the full picture of the defect.

Longitudinal wave and transverse wave have been used for flaw detection in welds, and the size can only be determined by the height of the reflected wave of the defect, which cannot reflect the shape of the defect. The plate wave is used to detect thin plates and thin-walled pipes with a thickness less than 6 mm. Surface waves can only propagate on solid surfaces. Surface waves can continue to propagate after encountering surface- or near-surface defects or after reflected waves are generated on the end faces of the workpiece. As such, the positions of these defects and the dimensions of the workpiece can be known by the positions of these reflected waves. In FIG. 1-4, for example, the probe used is called a surface wave probe.

SUMMARY

In view of the technical problem of the lack of a flaw detection method capable of accurately detecting defects in the prior art as discussed above, the present disclosure provides a reflection-diffraction-deformation flaw detection method with a transverse wave oblique probe. The present disclosure mainly uses the reflected wave having the reflection characteristics and the diffracted wave having the diffraction characteristics to determine the presence or absence of the defect. Further, through the deformed wave having deformation characteristics, namely the deformed surface wave produced at the endpoints of the defect, and through the propagation of the surface wave along the defect surface, the shape and size of the defect are obtained. Further, through the combination of paths trailed by the deformed surface wave, deformed transverse wave, and deformed longitudinal wave that are generated by the defect as well as that trailed by the transmit transverse wave, the causes of all the waves in the screen are revealed, thereby obtaining the basis for determining the angle or orientation of the defect. Which thereby realizes the precise positioning, quantification and characterization of the defect, enabling the three-dimensional rendering of truthful shape of the defect relying solely on A-ultrasound technology.

The technical means adopted by the present invention are as follows.

There is provided a reflection-diffraction-deformation flaw detection method with a transverse wave oblique probe, the method including the following operations.

When an ultrasonic transverse wave encounters a defect during propagation, it can generate a reflected wave, a diffracted wave, and a deformed wave. Through a comprehensive analysis of these waves, the presence or absence of the defect is determined by the reflected wave having reflection characteristics and the diffracted wave having the diffraction characteristics. The shape and size of the defect are determined by the deformed wave having deformation characteristics, namely the deformed surface wave generated at the endpoints of the defect which propagates on the defect surface. Furthermore, by the combination of paths trailed by the deformed surface wave, the deformed transverse wave, and the deformed longitudinal wave that are generated by the defect as well as that trailed by the transmit transverse wave, causes of all those waves in the screen can be revealed, thereby realizing the precise positioning, quantification and characterization of the defect, enabling the three-dimensional rendering of the truthful shape of the defect relying solely on A-ultrasound technology.

In the ultrasonic flaw detection process, first a primary-wave flaw detection is performed on one side. When a defect is encountered, a defect waveform A will appear. The defect waveform A includes at least one or more selected from the group consisting of a reflected wave, a diffracted wave, and a deformed wave. When a secondary-wave flaw detection is used and a defect is encountered, a defect waveform B will appear, which includes at least one or more selected from the group consisting of a reflected wave, a diffracted wave, and a deformed wave.

Secondly, when a primary-wave flaw detection is performed on the other side and a defect is encountered, then a defect waveform C will appear which includes at least one or more selected from the group consisting of a reflected wave, a diffracted wave, and a deformed wave. When a secondary-wave flaw detection is used and a defect is encountered, then a defect waveform D will appear which includes at least one or more selected from the group consisting of a reflected wave, a diffracted wave, and a deformed wave.

When defect waveform A and defect waveform B, or defect waveform C and defect waveform D are exactly the same, then the defect is symmetrical up and down on one side; otherwise when defect waveform A and defect waveform C, or defect waveform B and defect waveform D are exactly the same, then the defect is symmetrical left and right on both sides.

Thereby, the reflection-diffraction-deformation flaw detection method using a transverse wave oblique probe is enabled employing the combined flaw detection with the ultrasonic primary-wave and ultrasonic secondary-wave and waves of even higher orders at the two sides of the weld, which essentially combines the reflected wave, the diffracted wave and the deformed wave that are generated by the defect. Some defects can be accurately positioned, quantified, and characterized by presence of the defect's reflected wave, diffracted wave, and deformed wave, after performing a primary-wave flaw detection on one side. Some defects can be accurately positioned, quantified, and characterized by presence of the defect's reflected wave, diffracted wave, and deformed wave, after performing a secondary-wave flaw detection on one side. Likewise, Some defects can be accurately positioned, quantified, and characterized by presence of the defect's reflected wave, diffracted wave, and deformed wave, after performing a primary-wave flaw detection on the other side, or can be accurately positioned, quantified, and characterized by presence of the defect's reflected wave, diffracted wave, and deformed wave, after performing a secondary-wave flaw detection. Each flow detection result can be verified against each other. The method includes the following operations.

S1. Determination of flaw detection sensitivity: The sensitivity of the reflection-diffraction-deformation flaw detection method is based on the existing Φ3 mm transverse through-hole sensitivity, which is so increased by more than 10 dB that it does not affect the flaw detection; or uses the Φ0.5 mm transverse through-hole as the initial sensitivity, alternatively, the sensitivity can also be determined according to the smallest defect allowed by design requirements. Different products have different requirements for the type and size of the defect, so the sensitivity is also different. The determination of sensitivity is based on the detection of the smallest defect. After the defect is found, the assessment of the defect is not based on sensitivity, but on the reflected-diffracted-deformed waves of the defect. When the reflected wave of the defect is relatively low, the sensitivity needs to be promoted. When the defect has only one reflected wave, the sensitivity needs to be lifted so as to make the reflected wave, the diffracted wave, and the deformed wave of the defect appear at the same time. When the reflected wave, the diffracted wave, and the deformed wave of the defect are relatively high thus affecting the judgement, then the sensitivity should be appropriately reduced so that it doesn't affect the judgment.

S2. Determination of the probe angle: In the reflection-diffraction-deformation flaw detection method, the selection of the probe angle is independent of the groove bevel angle of the weld, and is unrelated to the thickness of the plate. It is associated with the ability of uncovering and assessing defects. Only one probe angle is selected, namely 45° transverse wave oblique probe. If the detection with the 45° transverse wave oblique probe leads to unpenetrated zones (dead zones) on the detection site, then probes at other angles are all used for compensation or for auxiliary flaw detection. Regarding special welds and special defects, special probes may need to be made.

S3. Determination of the type and size of the defect: the defects are composed of plane defects, circular and semi-circular defects, and volume defects.

S4. Length measurement of the defect: 6 dB method and 15°-45° rotation reflection-diffraction-deformation method are employed to measure the length.

S5. Positioning of the defect: After the size and shape of the defect are determined, the defect can be relatively accurately positioned on all directions, including up, down, left, and right.

S6. Characterization of the defect: After the shape and position of the defect are determined, the defect can be characterized as the same time.

Further, in step S3, the types of the plane defect includes the following cases: the plane defect is parallel to the detection surface, the plane defect is perpendicular to the detection surface, the plane defect is inclined from being perpendicular to the detection surface to the probe side, and the plane defect is inclined from being perpendicular to the detection surface to the opposite side of the probe side. The types of flaw detection for circular and semi-circular defects include: spherical air hole inspection, transverse through-hole inspection, flat-bottom inspection, and semi-circular defect inspection. Types of polygonal defect consisting of planar shapes include: triangular defects, quadrilateral defects, and hexagonal defect detection.

Further, in step S4, when the length defect needs to be measured, it is first checked whether the length direction of the defect is regular. If the reflected, diffracted, and deformed waves to the endpoints are all the same, then 6 dB method is used to measure the length. If the reflected, diffracted, and deformed waves to the endpoints are different, the 6 dB is used to measure the endpoints, and then the probe is tilted 15°-45° and moved to aim at different endpoints, so as to find out the reflected, diffracted, and deformed waves of the endpoints. Then measurements are performed on both sides of the weld and the measured longest point is taken.

Further, in addition to the reflected, diffracted, and deformed waves generated by the defect, the reflected waves and deformed waves generated by the weld corners are used to evaluate the quality of the weld formation, and to assess the presence of defects on the surface and near-surface of the weld. The equivalent method considers that the reflected wave appearing in front of the weld corner reflected wave is determined as a defect's reflected wave, and the wave appearing after the weld corner reflected wave is not considered. Because the reflected waves and deformed waves and multiple reflected waves generated by the weld corners are regular, the reflection-diffraction-deformation flaw detection method with the transverse wave oblique probe believes that of the waves appearing behind the reflected waves of the weld corners are not regular, they would be considered as defects, and all the waves appearing on the scanning line must be analyzed.

Further, the endpoint of the defect generates a surface wave under the action of a transverse wave, and the surface wave propagates along the defect surface. When propagating to an end corner (endpoint) of the defect, a Q wave will be generated. The appearance of Q wave during flaw detection proves that there are surface waves generated by the defect. When the surface wave propagates to the end corner (endpoint), a reflected wave would be generated, and so the size of the defect surface can be calculated based on the position of the reflected wave. The surface wave would continue propagating a full circle around the polyhedron after being reflected at the end corner so as to generate a circumferential echo surrounding the polyhedron. These combined are the shape of the defect, and can be mutually verified against each other.

Further, after the defect is found by the transverse wave, the reflected wave, diffracted wave and deformed wave from the defect, together with the reflected wave from the weld corners, will form specific reflection loops. These loops can be mapped or programmed into software so as to confirm the generation of each reflected echo appearing in the weld flaw detection screen.

The reflection-diffraction-deformation flaw detection method is used to specify the return paths of the defect wave. And by plotting, all the reflected pulses appearing on the screen, totaling 77+2Q echoes, are analyzed to determine how all reflected pulses are generated. Although the 77+2Q echoes don't actually appear at the same time, all the reflected pulses appearing would not fall out of the principle of generation of the 77+2Q echoes. The formation of the 77+2Q echoes is related to the formation of the weld and the shape and location of the defect. The 77+2Q echoes don't include multiple reflections at one location.

Further, the reflected pulses generated by different sound velocities and different paths on the screen are processed by software and displayed in different colors. A normal transverse wave is set to one color, a longitudinal wave to one color, a surface wave to one color, a transverse to longitudinal transition is set to one color, a longitudinal to transverse transition is set to one color. Similarly, a transverse to surface transition, a surface to longitudinal transition, a surface to transverse transition all have their respective set colors, and combinations of these colors. Which enables the observation to be more intuitive.

Further, the pulses are processed by software to show up in one line, which reduces the influence of the blind areas brought about by the pulse width.

Further, according to the positions where the reflected wave, the diffracted wave, and the deformed wave appear, the three-dimensional shape and size of the defect are displayed on the screen through software processing.

Compared with the related art, the present disclosure provides the following advantages.

1. Sound waves have the principles of optical reflection, refraction, and diffraction, but the process of sound wave vibration generates forces, which are not available in optical reflection characteristics. Due to the generation of forces, the defect endpoints have different theories from optical reflection, refraction, and diffraction. The main reason includes the theory that the endpoints produce deformed surface waves, the decomposition of forces at the endpoints, as well as the common reflection and diffraction, so that 77+2Q echoes are generated, thereby achieving precise positioning, quantification, and characterization of the defect.

2. The defect endpoints generate surface waves, and the propagation of the surface waves along the defect surface is also in conformity with the Snell's law. Thus, applying the propagation theory of the endpoint surface waves, the shape of the defect can be precisely determined.

3. A reflection-diffraction-deformation flaw detection method and Q-wave theory are proposed to accurately locate, quantify, and characterize defects.

4. On the basis of the analysis of a wave-front line, a wave-rear line, as well as a peak of the pulse wave by push, pull, and observation of the pulses on the screen by push, pull, and twist of the probe, the pulses changing synchronously are subjected to merger-of-similar-terms analysis, enabling precise positioning, quantification, and characterization of the defect.

5. Proposal and application of 77+2Q echo analysis method to precisely positioning, quantification, and characterization of the defect.

6. The formula of the 77+2Q echo analysis method are programmed into software, and the data is processed through the software to display the three-dimensional shape and position of the defect on the screen, enabling precise positioning, quantification, and characterization of the defect.

7. The reflected pulses generated by different sound velocities are processed by software and displayed in different colors. For example, normal transverse waves are indicated by one color, longitudinal waves are indicated by one color, surface waves are indicated by one color, transverse-to-longitudinal transitions are indicated by one color, and longitudinal-to-transverse transitions are indicated by one color. Similarly, transverse-to-surface transitions, surface-to-longitudinal transitions, surface-to-transverse transitions all have their respective colors and combinations of these colors. Therefore, the observation is more intuitive, the input is more convenient, and the defects can be precisely positioned, quantified, and characterized.

8. The 77+2Q echo pulses are each processed by software to appear in one line, which reduces the impact of the blind area caused by the pulse width, enabling precise positioning, quantification, and characterization of the defect.

9. Determination of sensitivity. First, use Φ0.5 mm transverse through hole as the initial sensitivity. Second, determine the sensitivity according to the design requirements. Different products have different requirements for the type and size of the defect, so the sensitivity is also different. The determination is based on the detection of the smallest defect. The judgement of the defect is not based on the sensitivity after the defect is found, but based on the reflected, diffracted, and deformed waves of the defect. When the reflected wave of the defect is relatively low, the sensitivity needs to be increased. When the defect has only one reflected wave appearing, the sensitivity needs to be lifted up to make the reflected, diffracted, and deformed waves appear at the same time. When the reflected, diffracted, and deformed waves are relatively high thus affecting the judgement, the sensitivity then needs to be appropriately reduced so as not to affect the judgment. Then the defects can be precisely positioned, quantified, and characterized.

10. Weld flaw detection uses only one angle, namely 45°. If with the detection with the 45° probe there are areas that are not within the reach of the scan range, a probe at another angle can be added for complement flaw detection thereby enabling precise positioning, quantification, and characterization of the defect.

11. The grain size should be considered in the flaw detection of the weld. Even if there is no defect in the weld, the coarseness of the grain caused by the non-standard welding will also affect the strength.

Based on the above reasons, the present disclosure can be widely promoted in the fields of flaw detection and the like.

BRIEF DESCRIPTION OF DRAWINGS

To better illustrate the technical solutions in the embodiments of the present disclosure or those in the related art, the drawings used in the description of these embodiments or the related art will be briefly illustrated. It is evident that the drawings in the following description are merely some embodiments of the present disclosure, and other drawings can be obtained based on these drawings by those having ordinary skill in the art, without making creative efforts.

In which reference signs represent the following components. 1. Probe; 2. Center of point of incidence; 3. Detection surface; 4. Flaw or defect; 5. Workpiece; 0. Initial wave; F. Flaw or defect echo; W. Side echo; B. Bottom echo.

Figure 1:
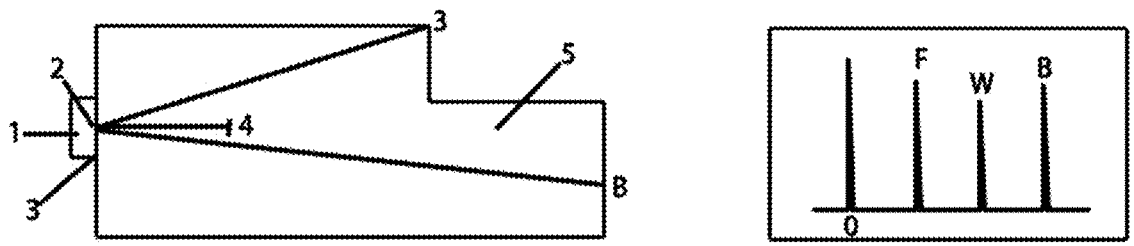
FIG. 1-1 is a schematic diagram illustrating the flaw detection with a longitudinal wave normal probe in the related art.
Figures 1, 2:
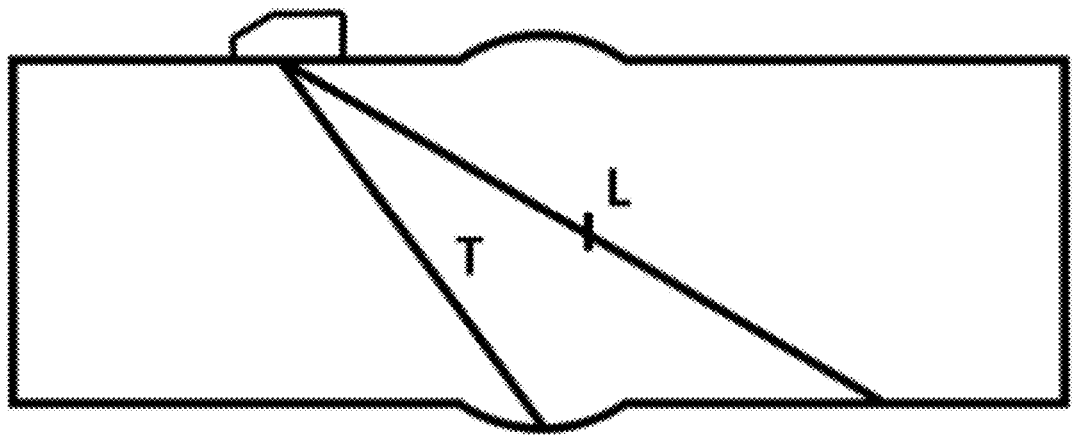

FIG. 1-2 is a schematic diagram illustrating the flaw detection with a longitudinal wave oblique probe in the related art.

In which, L strands for longitudinal wave, while T stands for transverse wave.

Figures 1, 2, 3:
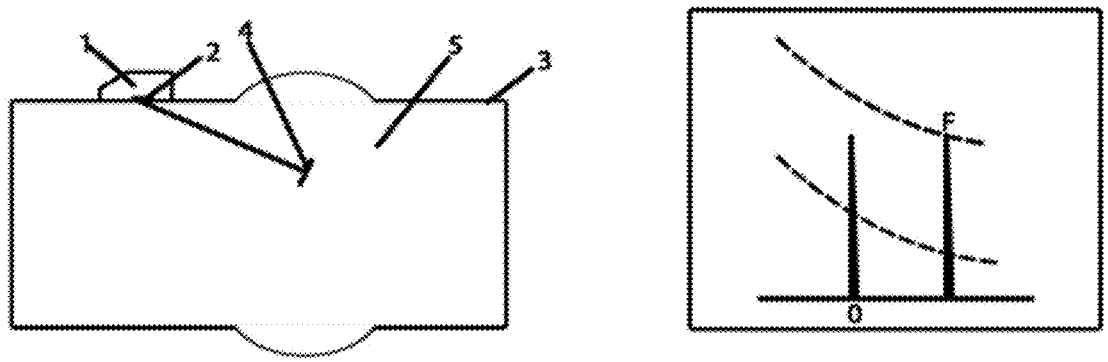

FIG. 1-3 is a schematic diagram illustrating the flaw detection with a transverse wave oblique probe in the related art.

In which reference signs represent the following components. 1. Oblique probe; 2. Center of point of incidence; 3. Detection surface; 4. Flaw or defect; 5. Workpiece (piece under inspection); 0. Initial wave; F. Flaw or defect echo.

FIG. 1-4 is a schematic diagram illustrating the flaw detection with a surface wave probe in the related art.

In which reference signs represent the following components. 1. Probe; 2. Center of point of incidence; 3. Detection surface; 4. Flaw or defect; 5. Workpiece; 6. R surface wave; F. Defect wave; 0. Initial wave; abcdef are reflected waves from end corners.

FIG. 2 is a schematic diagram illustrating a weld groove in the related art.

FIG. 3 is a schematic diagram illustrating the origin of a probe angle in the related art.

Figures 1, 2, 3, 4:
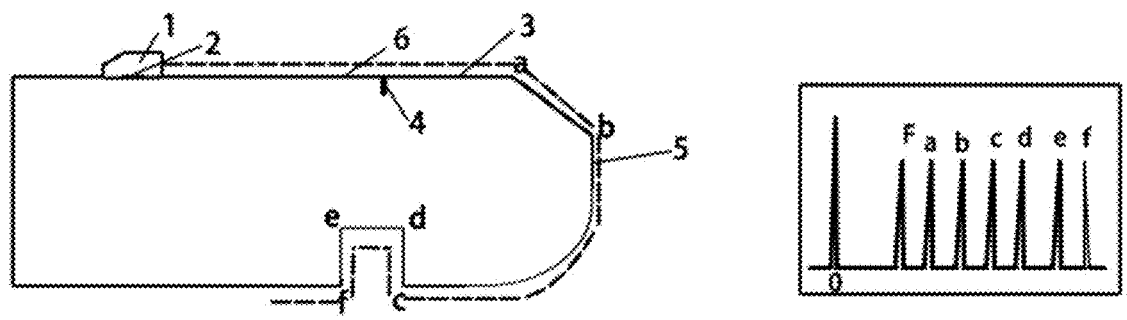
Figure 2:
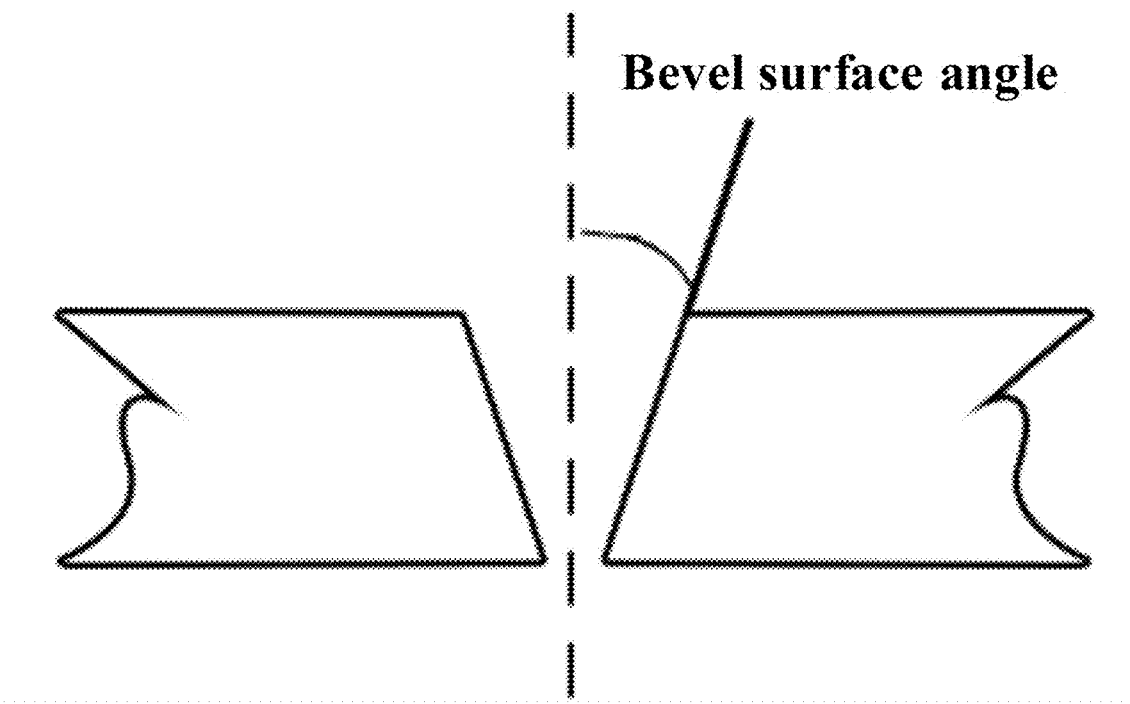
Figure 3:
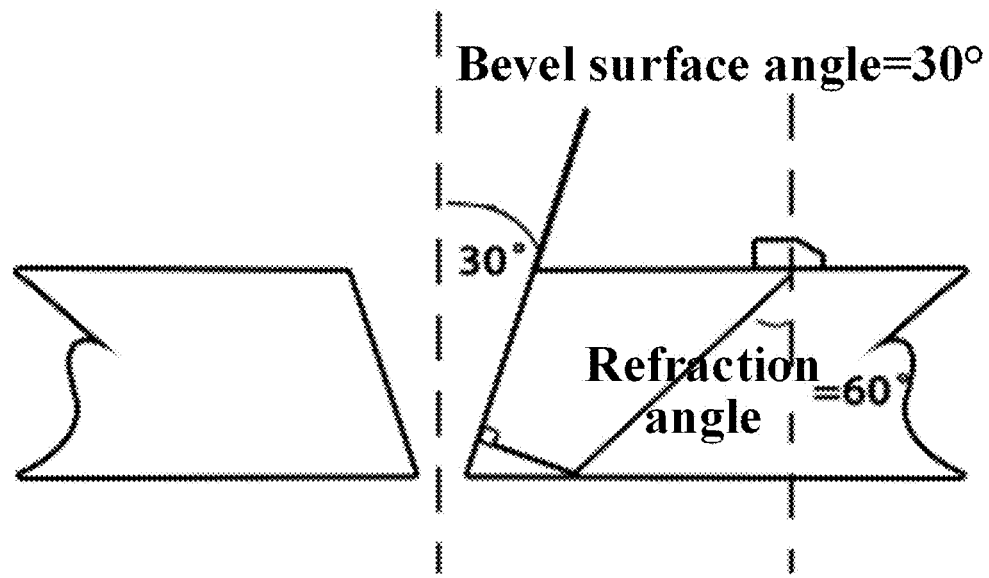
Figures 1, 4:
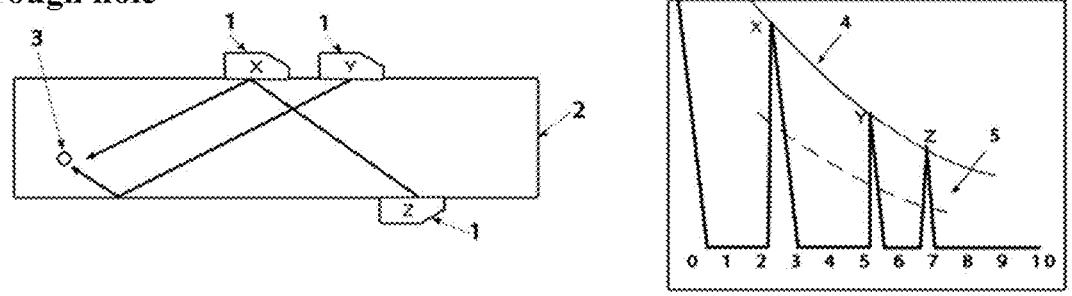
Figures 2, 4:
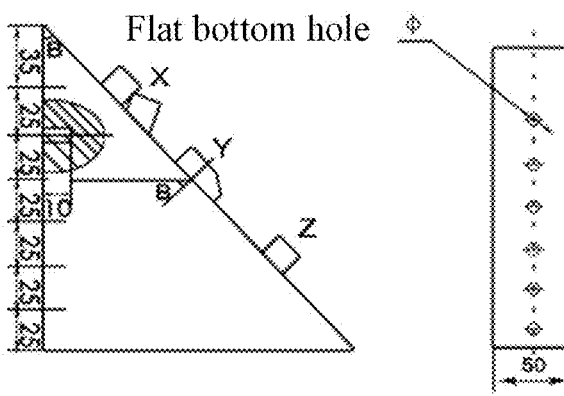

FIG. 4-1 is a schematic diagram illustrating a transverse through hole sensitivity test block in the related art.

In the figure, 1. Oblique probe; 2. Reference test block; 3. Reference reflector; 4. Distance amplitude curve (DAC); 5.50% DAC; X, Y, Z represent probe positions.

FIG. 4-2 is a schematic diagram illustrating a flat bottom hole sensitivity test block in the related art.

Figure 5:
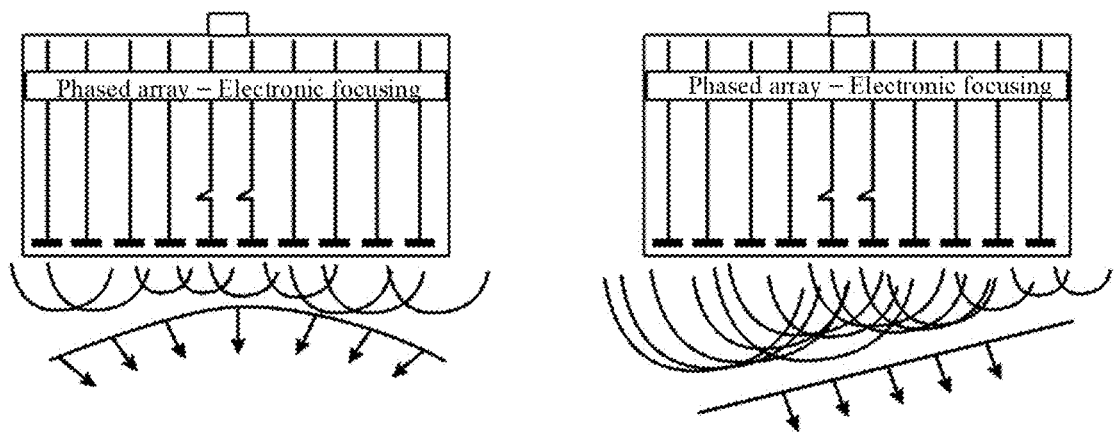

FIG. 5 is a schematic diagram illustrating the principle of electronic focusing and beam deflection realized by an ultrasonic phased array transducer in the related art.

Figure 6:
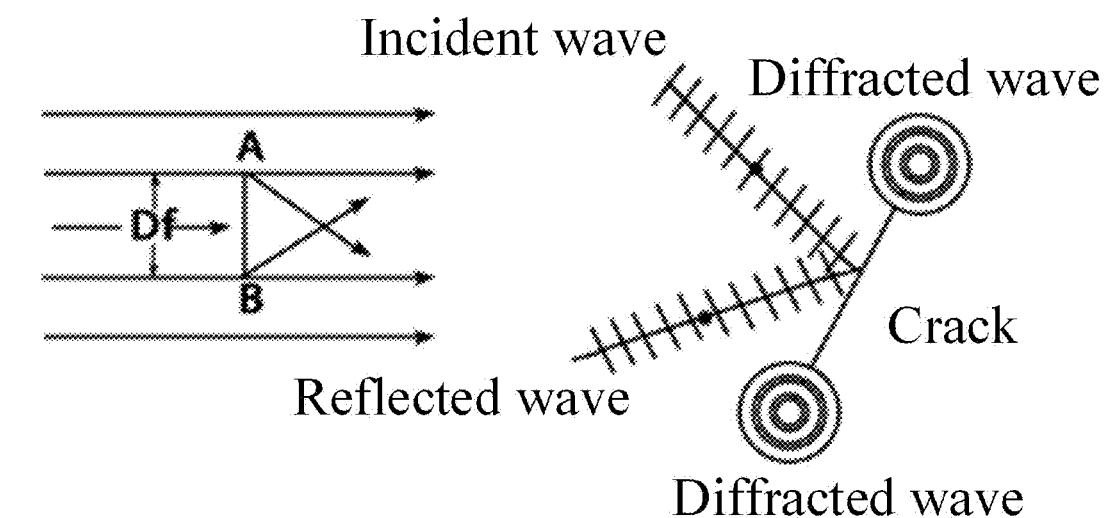

FIG. 6 is a schematic diagram illustrating the principle of diffraction in the related art.

Figure 7:
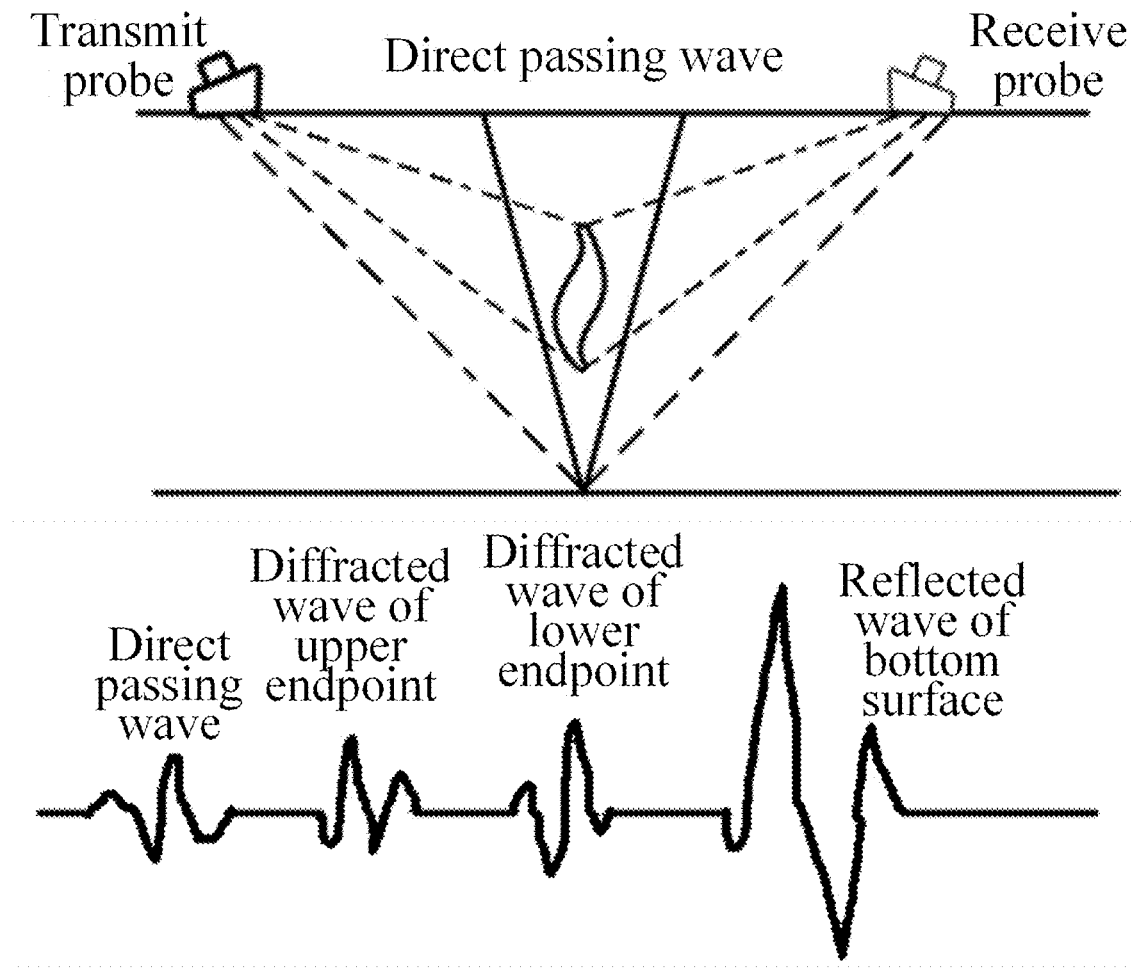

FIG. 7 is a schematic diagram illustrating the TOFD diffraction technique in the related art.

Figure 8:
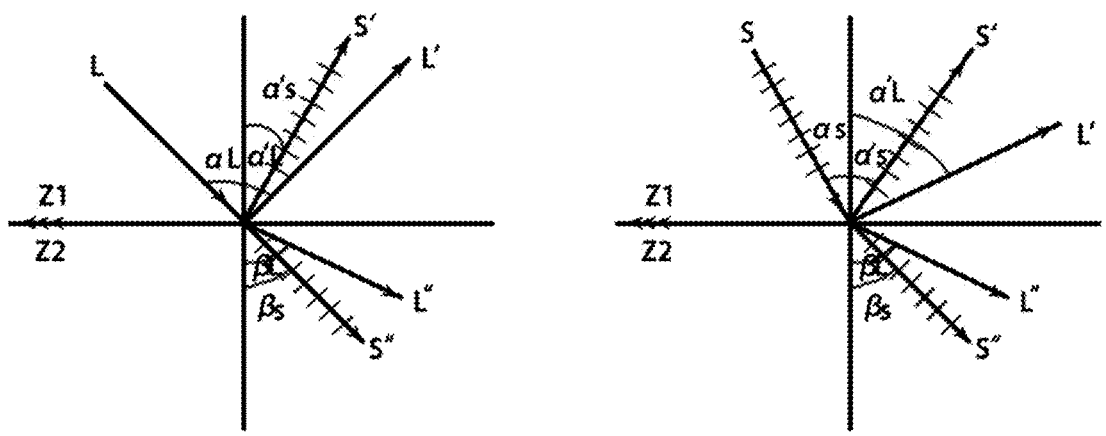

FIG. 8 is a schematic diagram illustrating wave mode conversion in the related art.

Figure 9:
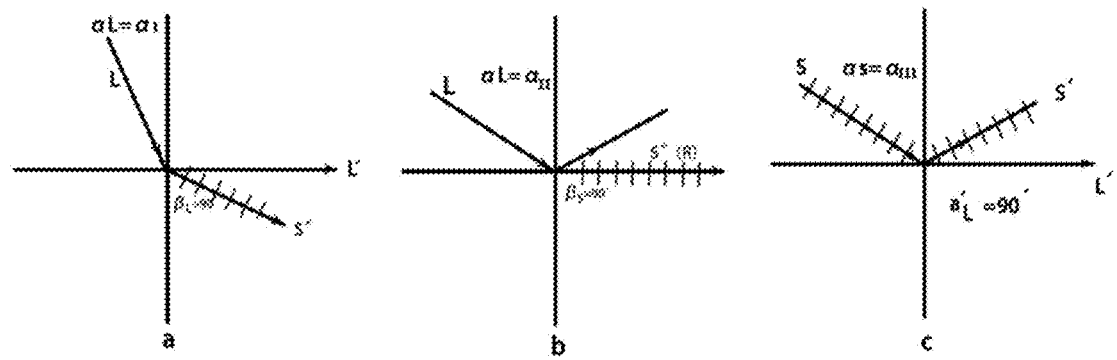

FIG. 9 is a schematic diagram illustrating the surface wave at a second critical angle in the related art.

Figure 10:
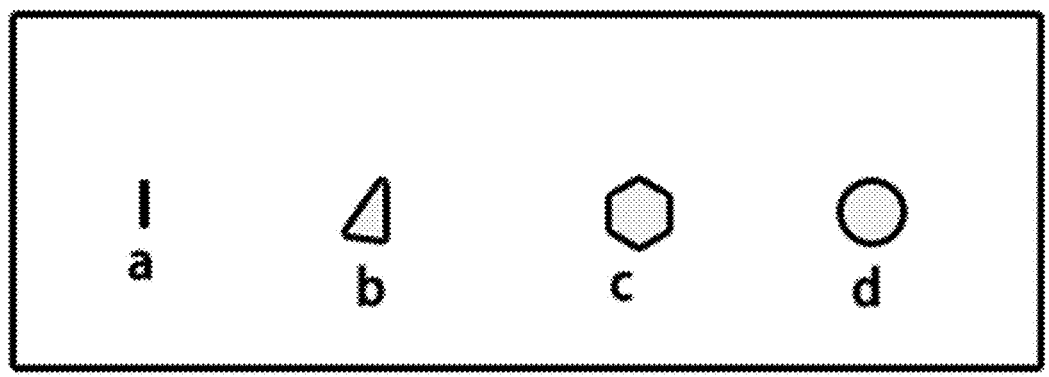

FIG. 10 is a schematic diagram of an artificial defect test block in the present disclosure.

In the figure, a. Plane; b. Triangle; c. hexagon; d. circle.

Figures 1, 11:
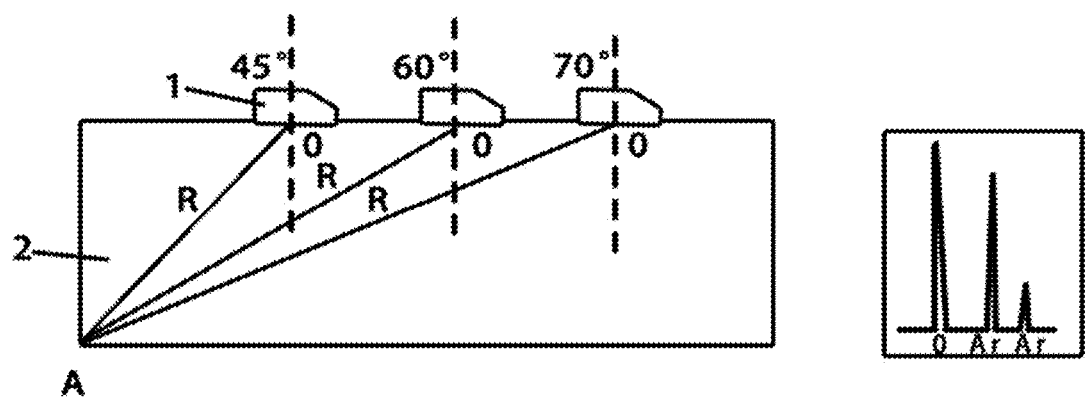
Figures 2, 11:
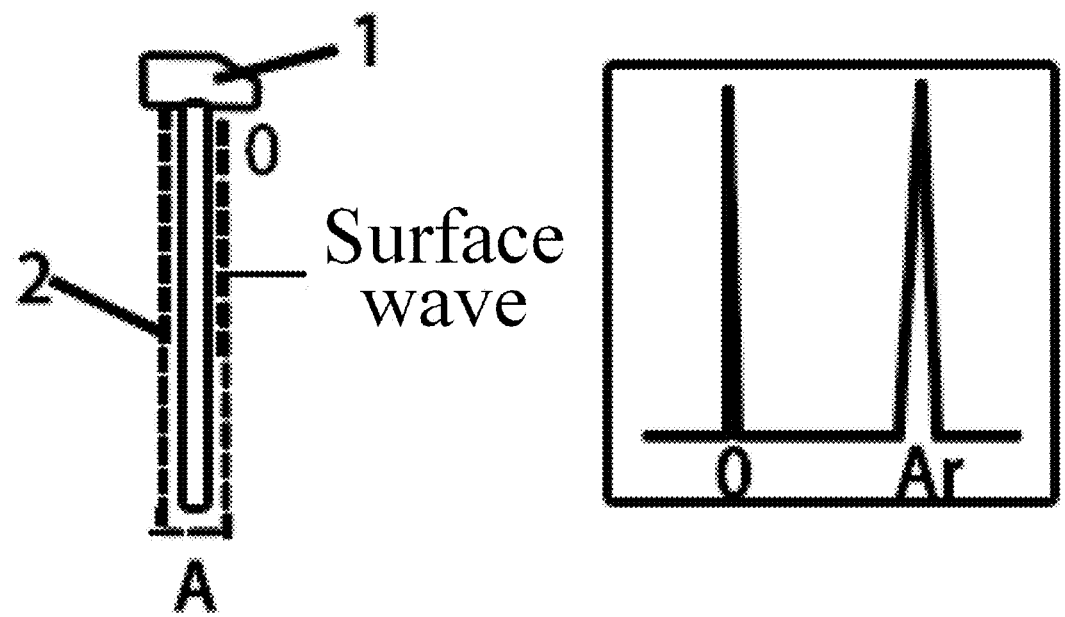

FIG. 11-1 is a schematic diagram illustrating a surface wave detection steel sheet of a transverse wave oblique probe in accordance with the present disclosure.

In the figure, 1. Transverse wave oblique probe; 2. Steel sheet; R. Surface wave; Ar. Reflected wave of surface wave; At. Reflected wave of transverse wave.

FIG. 11-2 is a schematic diagram illustrating surface wave detection steel sheet of a transverse wave oblique probe where the steel sheet is rotated 90°, in accordance with the present disclosure.

In the figure, 1. Transverse wave oblique probe; 2. Steel sheet; Ar. Reflected wave of surface wave.

Figure 12:
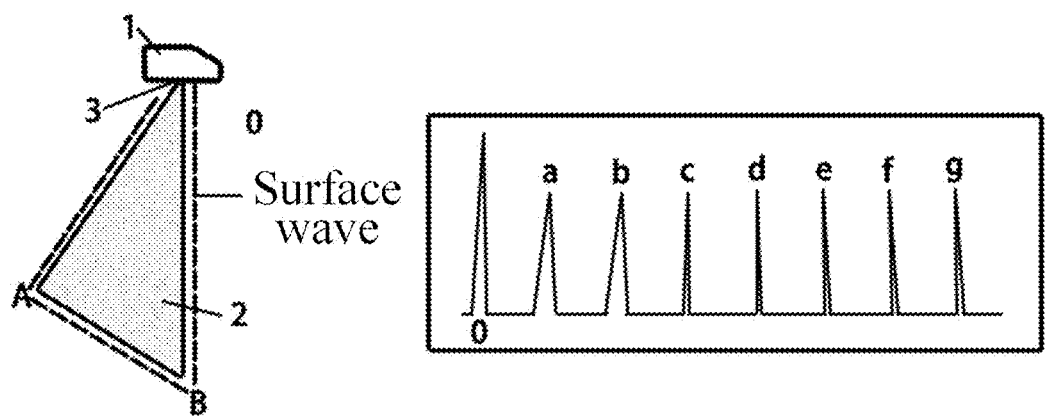

FIG. 12 is a schematic diagram illustration the detection of a triangle with surface wave using a transverse wave oblique probe, in accordance with the present disclosure.

In the figure, 1. Transverse wave oblique probe; 2. Triangular workpiece; 3. Coupling endpoint.

A is the A point reflected wave of the surface wave of the OA surface; b is the B point reflected wave of the surface wave of the OB surface; c is the superimposed reflected waves of the circumferential surface waves in the two directions of OABO and OBAO; d is the reflected wave of the surface wave of the OAB surface at the point B; e is the reflected wave of the surface wave of the OBA surface at point A.

Figures 1, 13:
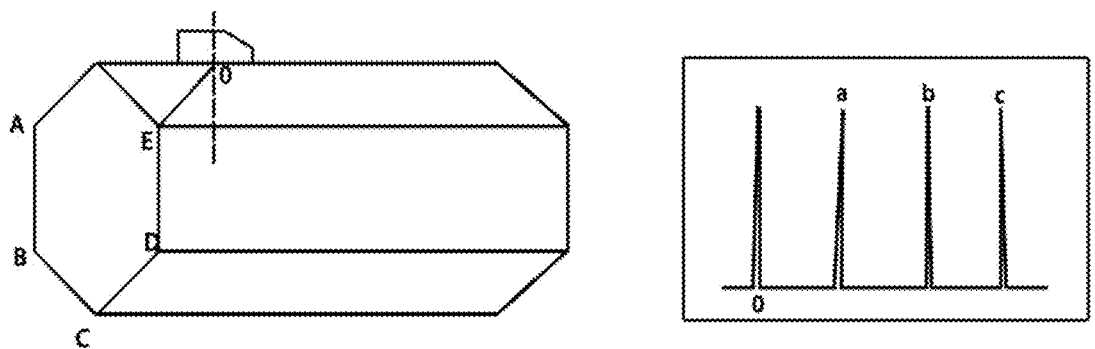
Figures 2, 13:
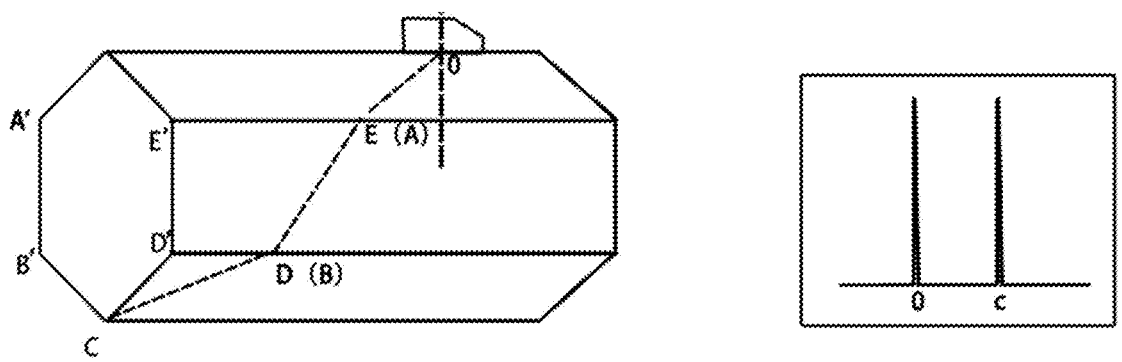
Figures 3, 13:
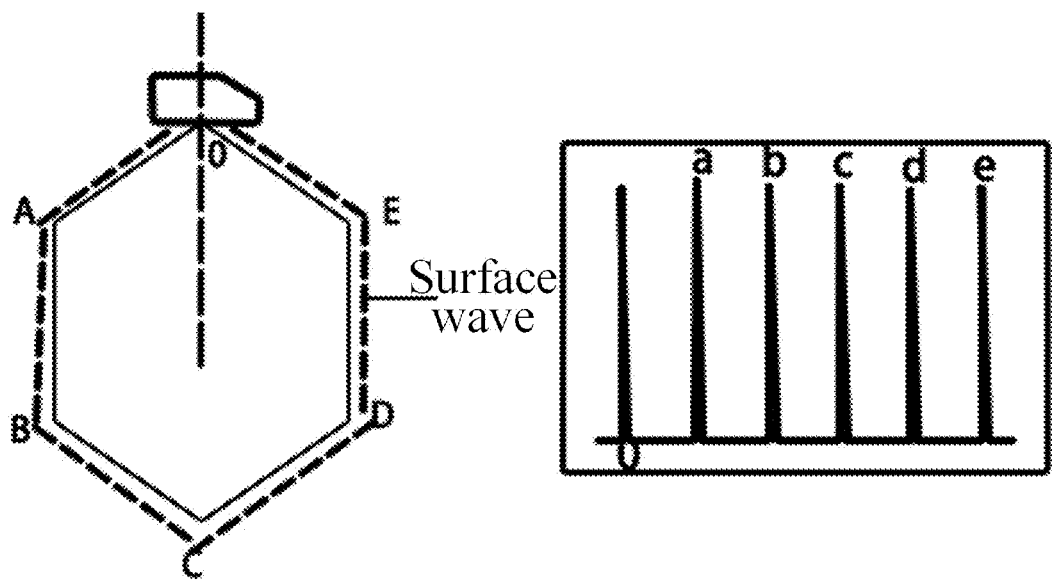

FIG. 13-1 is a schematic diagram illustrating the flaw detection of a hexagon with surface waves using a transverse wave oblique probe in accordance with the present disclosure.

In the figure, a stands for reflection as point A(E), b stands for the superimposed reflection of one circle of OEAO (OAEO), c stands for superimposed reflected wave of OEA (OAE).

FIG. 13-2 is a schematic diagram illustrating the flaw detection of a hexagon with surface waves using a transverse wave oblique probe in accordance with the present disclosure.

In the figure, c is the reflected waves of OEDC and OABC superimposed at point C, and is also the reflected waves of one circle of each of OEDCBAO and OABCDEO, where one circle of OCO is equal to the OC reflected distance, so that the reflected waves are coincident.

FIG. 13-3 is a schematic diagram illustrating the flaw detection of a hexagon with surface waves using a transverse wave oblique probe rotated 90° in accordance with the present disclosure.

In the figure, A is the superimposed reflected waves of OA and OE. b is the superposed reflected waves of OAB and OED; c is the superposed reflected waves of OABC and OEDC, which is also the superposed reflected waves of OABCDEO and OEDCABO; d is the superposed reflected waves of OABCD and OEDCD; e is the superimposed reflected waves of OABCDE and OEDCBA.

Figures 1, 14:
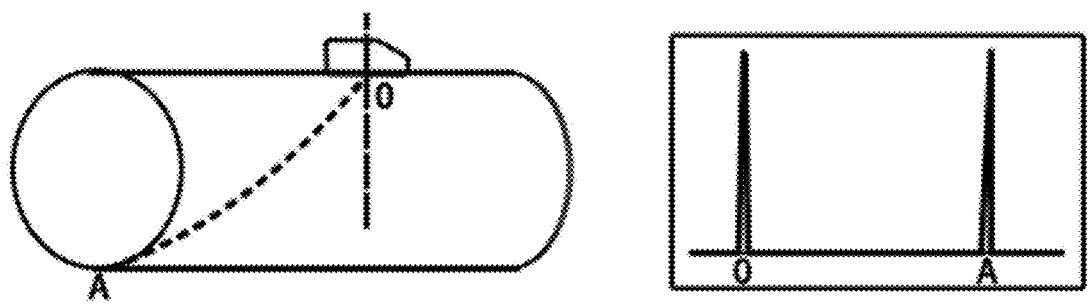
Figures 2, 14:
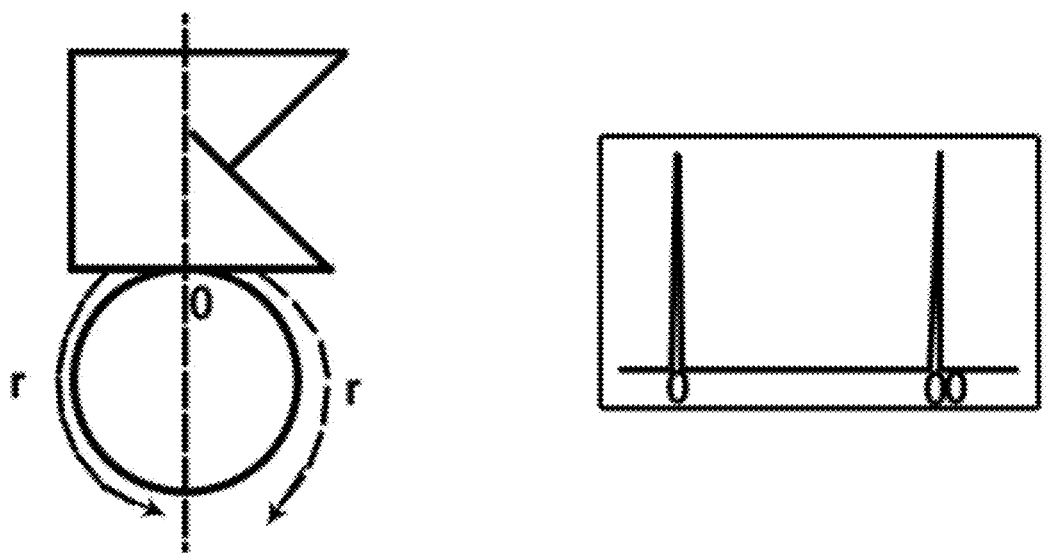
Figures 3, 14:
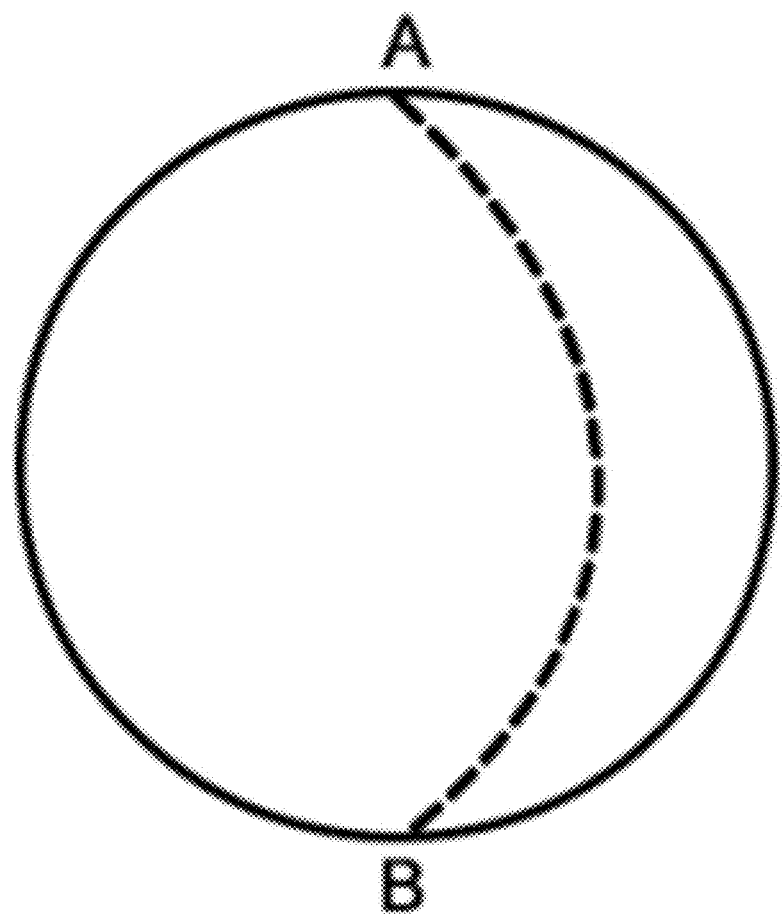
Figures 4, 14:
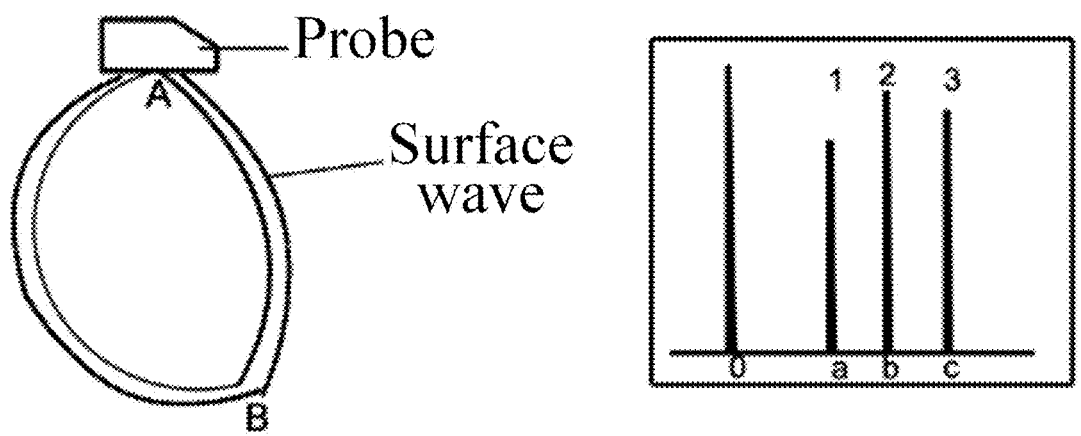
Figures 5, 14:
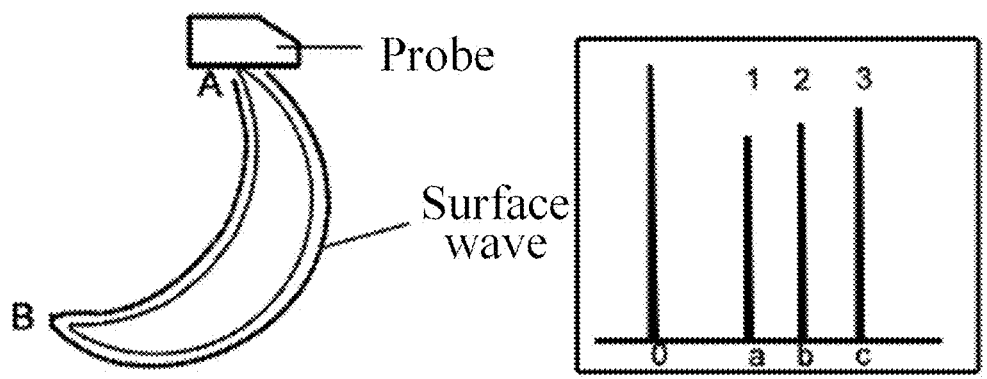

FIG. 14-1 is a schematic diagram illustrating the flaw detection of a cylinder with surface waves using a transverse wave oblique probe in accordance with the present disclosure.

FIG. 14-2 is a schematic diagram illustrating the flaw detection of a cylinder with surface waves using a transverse wave oblique probe in accordance with the present disclosure.

FIG. 14-3 is an exploded view of a cylinder in accordance with the present disclosure.

FIG. 14-4 is a schematic diagram illustrating the flaw detection of a half-moon shape with surface waves of a transverse wave oblique probe in accordance with the present disclosure.

FIG. 14-5 is a schematic diagram illustrating the flaw detection of a crescent-shaped with surface waves of a transverse wave oblique probe in accordance with the present disclosure.

Figure 15:
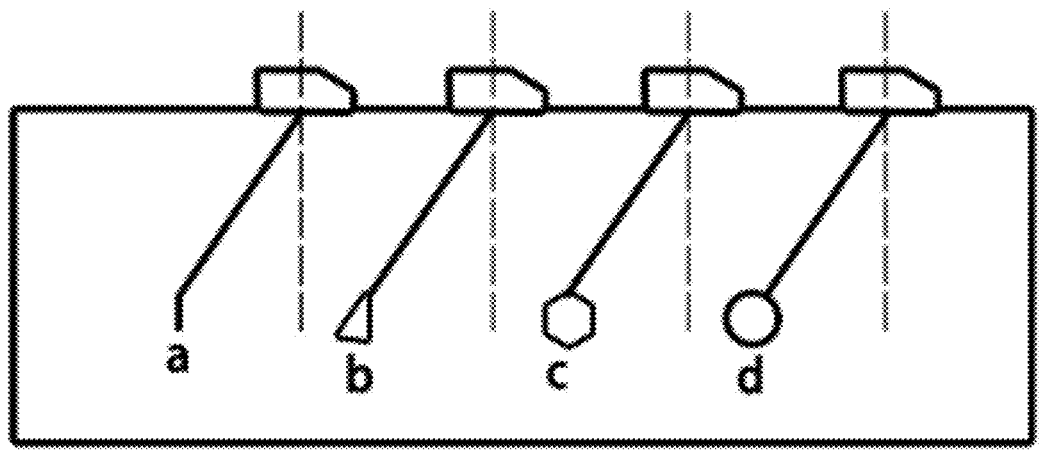
Figures 1, 15:
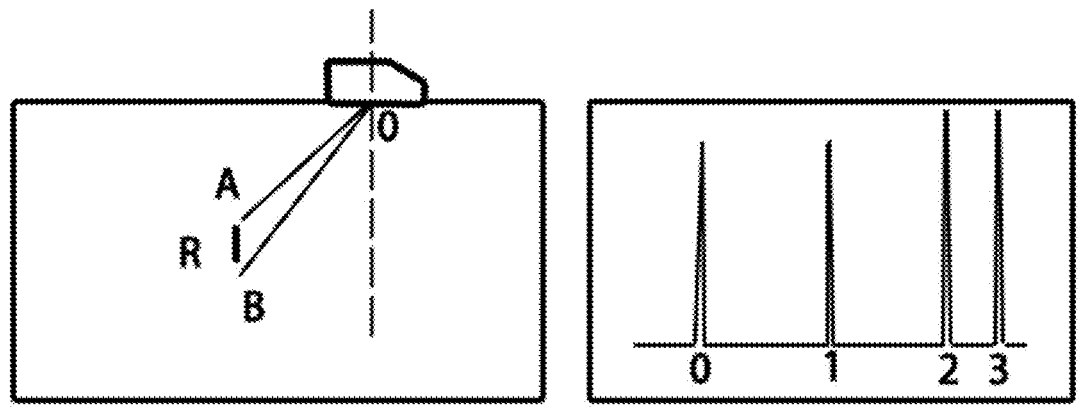
Figures 2, 15:
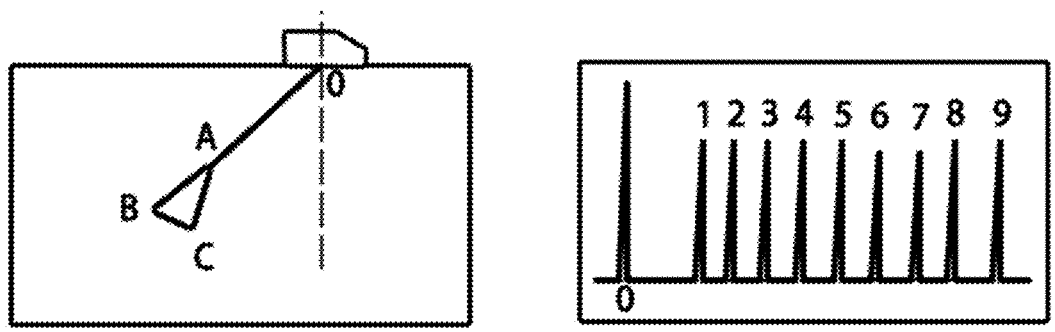
Figures 3, 15:
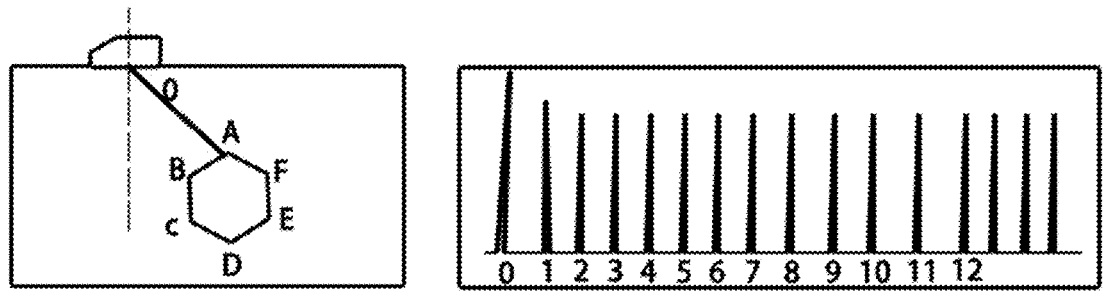
Figures 4, 15:
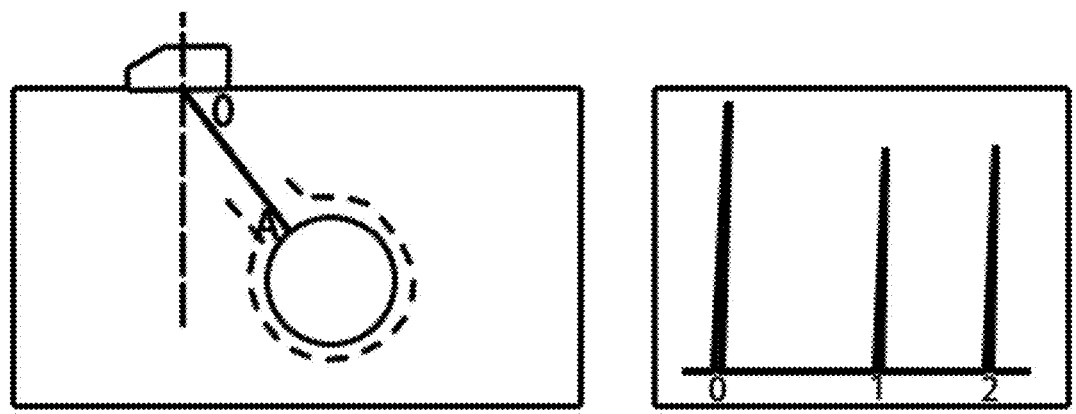
Figures 5, 15:
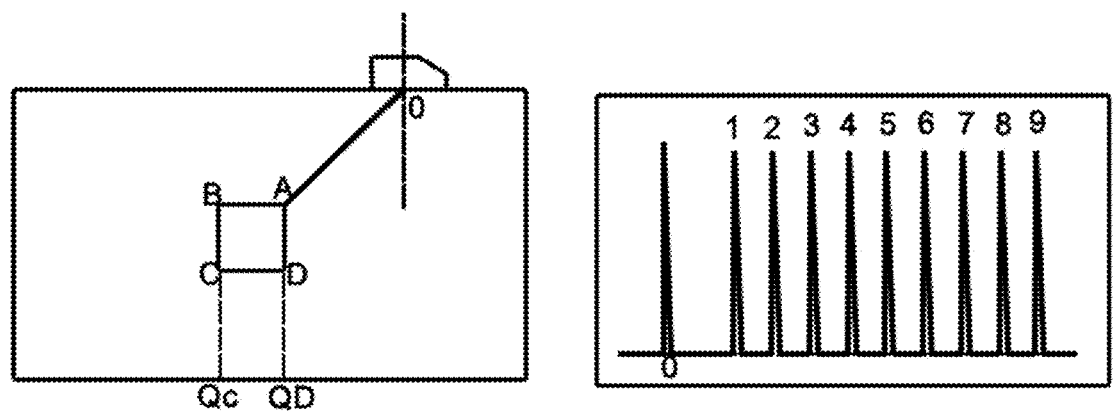

FIG. 15 is a schematic diagram illustrating the heterogeneous hole flaw detection test block in accordance with the present disclosure.

FIG. 15-1 is a schematic diagram illustrating the flaw detection of a planar shaped defect using endpoint surface waves in accordance with the present disclosure.

In the figure, 1 stands for point A reflected wave; 2 stands for point B reflected wave; 3 stands for point B reflected wave of the surface wave of the AB surface.

FIG. 15-2 is a schematic diagram illustrating the flaw detection of a triangular defect using endpoint surface waves in accordance with the present disclosure.

In the figure, 1 is the point A reflected wave; 2 is the point B diffracted wave; 3 is the point C diffracted wave; 4 is the reflected wave of the AC surface wave at point C; 5 is the reflected wave of the AB surface wave at point B; 6 is the superposed reflected waves of surface waves in two directions of ABCA and ACBA; 7 is the point B reflected wave of the ACB surface wave after passing point C; 8 is the point C reflected wave of the ABC surface wave after passing point B.

FIG. 15-3 is a schematic diagram illustrating the flaw detection of a polygon using the endpoint surface wave in accordance with the present disclosure.

In the figure, 1 stands for point A reflected wave, each point has reflected wave and surface wave reflected wave as well as superimposed reflected waves of surface waves in two directions.

FIG. 15-4 is a schematic diagram illustrating the flaw detection of a circular shaped defect using endpoint surface waves in accordance with the present disclosure.

In the figure, 1 stands for point A reflected wave, and 2 stands for the superimposed reflected waves of the circular surface waves in two directions.

FIG. 15-5 is a schematic diagram illustrating the flaw detection of a square-shaped defect using endpoint surface waves in accordance with the present disclosure.

Figure 16:
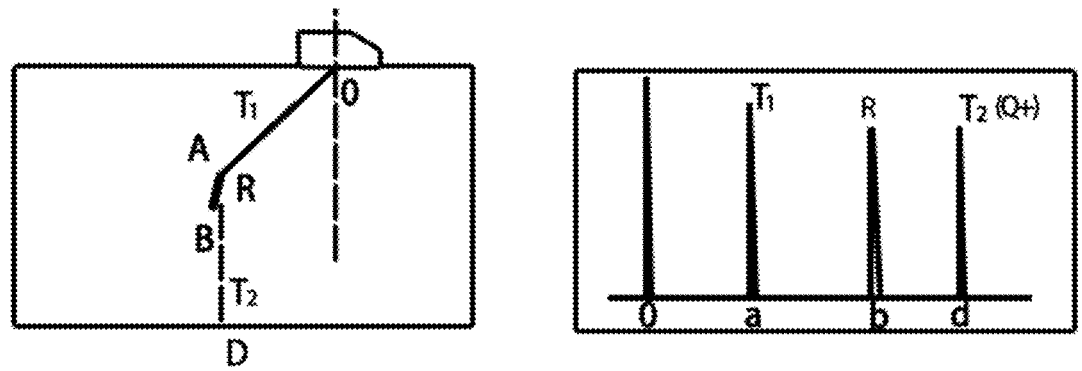

FIG. 16 is a schematic diagram illustrating the generation of TRT wave.

Figures 1, 17:
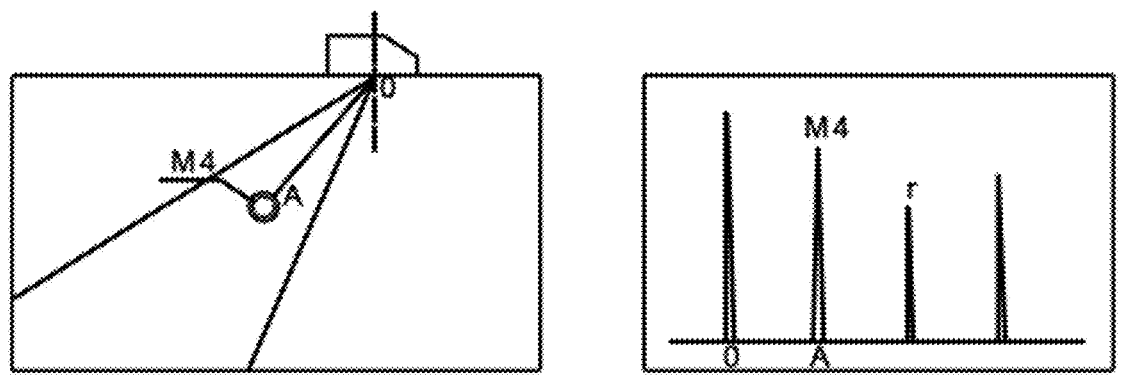
Figures 2, 17:
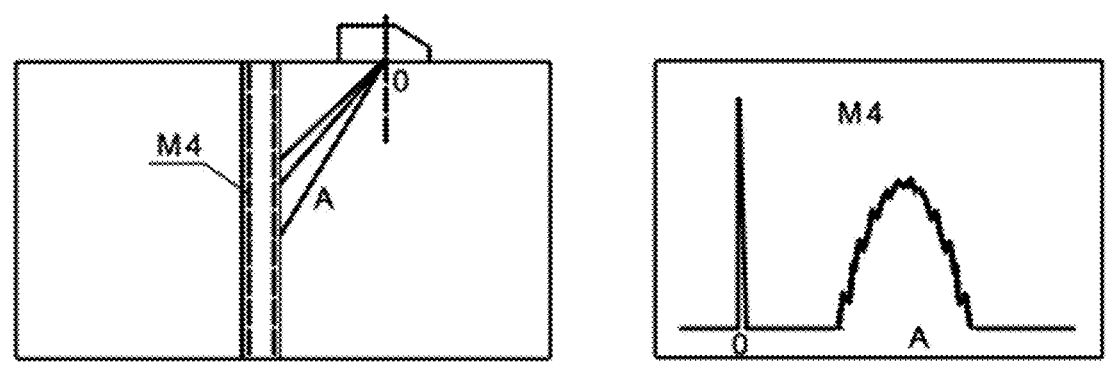

FIG. 17-1 is a schematic diagram illustrating the flaw detection of a horizontal through-hole having a thread of a probe in accordance with the present disclosure.

FIG. 17-2 is a schematic diagram illustrating the flaw detection of a vertical through-hole having a thread of a probe in accordance with the present disclosure.

Figure 18:
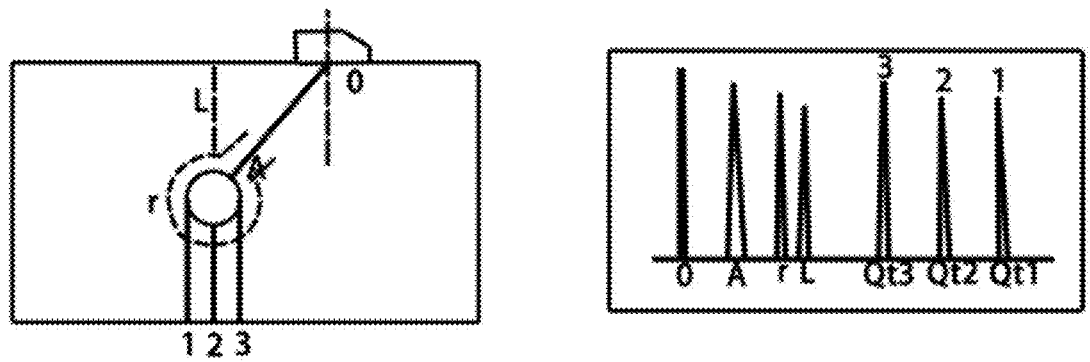

FIG. 18 is a schematic diagram illustrating the number of Qt waves of a circular defect in accordance with the present disclosure.

Figure 19:
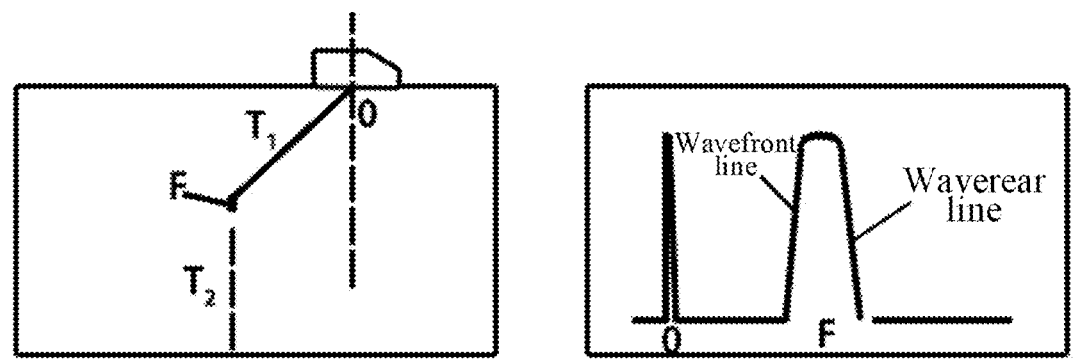

FIG. 19 is a diagram separately illustrating a wave-front line, a wave-rear line, and a peak in accordance with the present disclosure.

Figure 20:
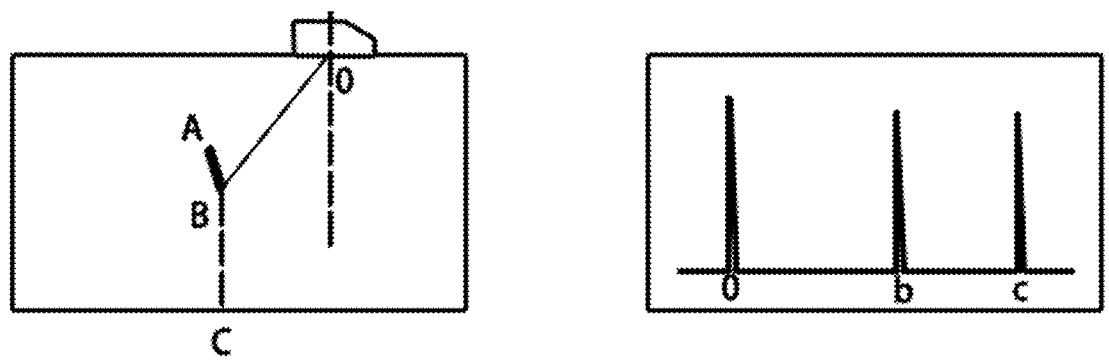

FIG. 20 is a schematic diagram illustrating a pseudo "Qt" wave in accordance with the present disclosure.

In the Figure, b is the point B diffracted wave of the defect, c stands for the reflected wave generated by the point B transverse wave shot to the bottom surface.

Figure 21:
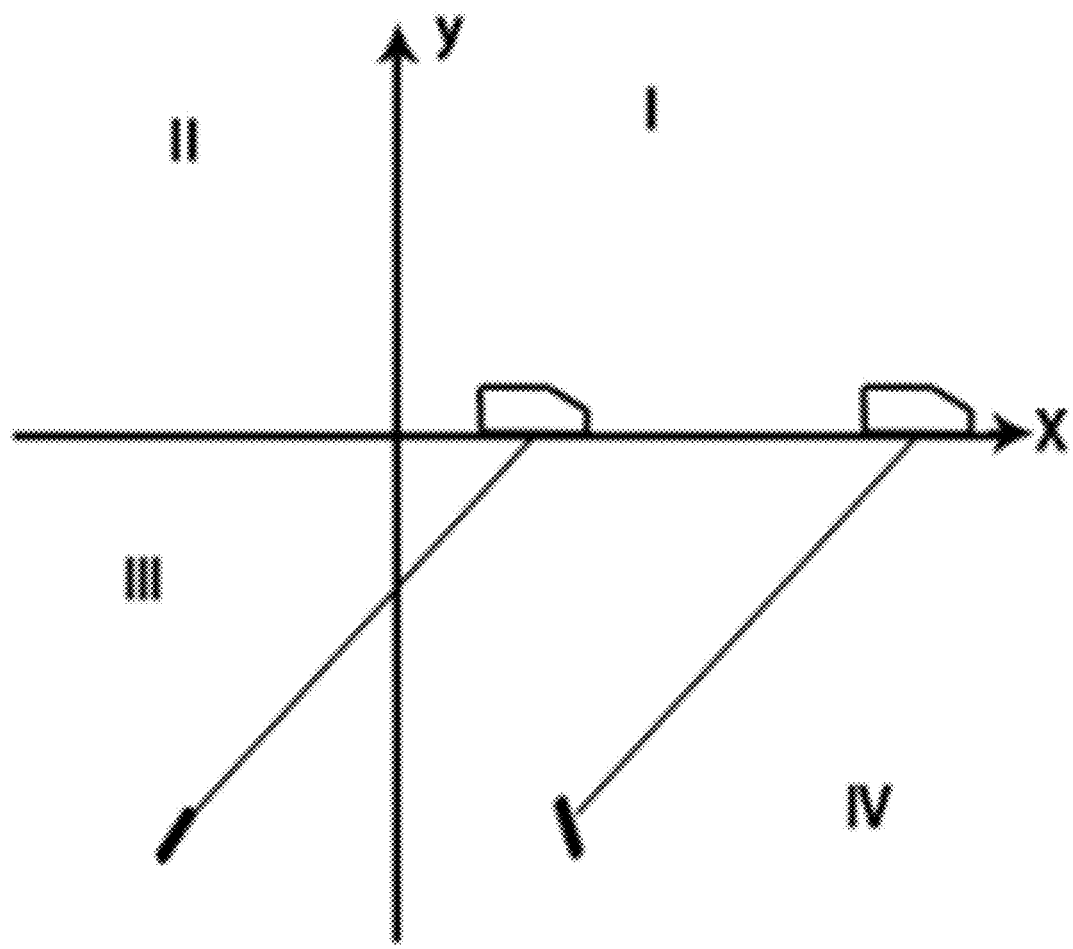

FIG. 21 is a schematic diagram illustrating determining the presence or absence of Qt waves by the orientation of the defect.

Figure 22:
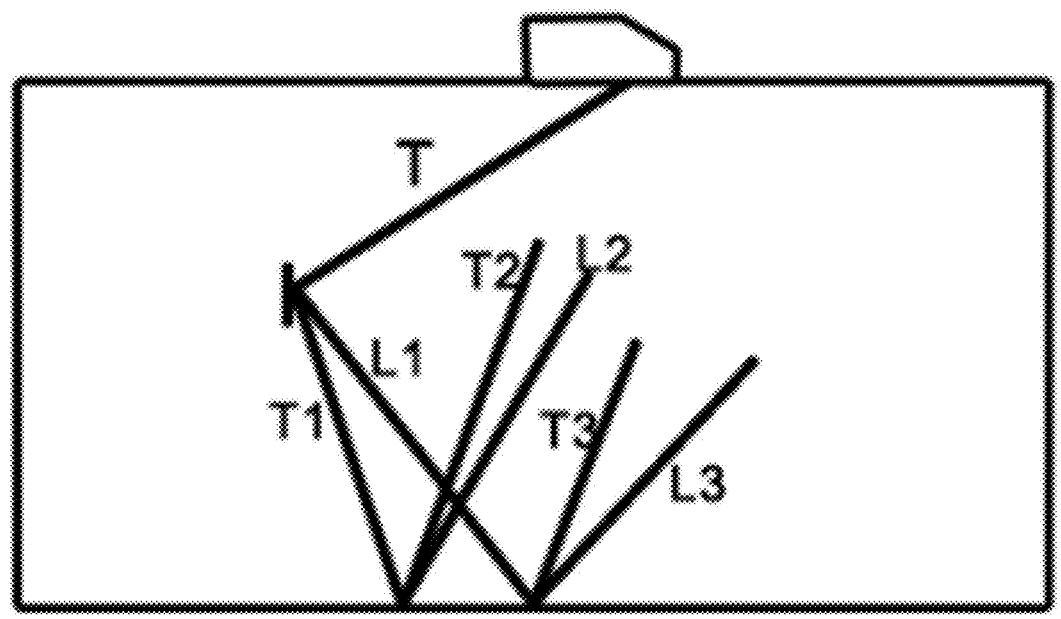

FIG. 22 is a schematic diagram illustrating the reflected wave of the defect in accordance with the present disclosure.

Figure 23:
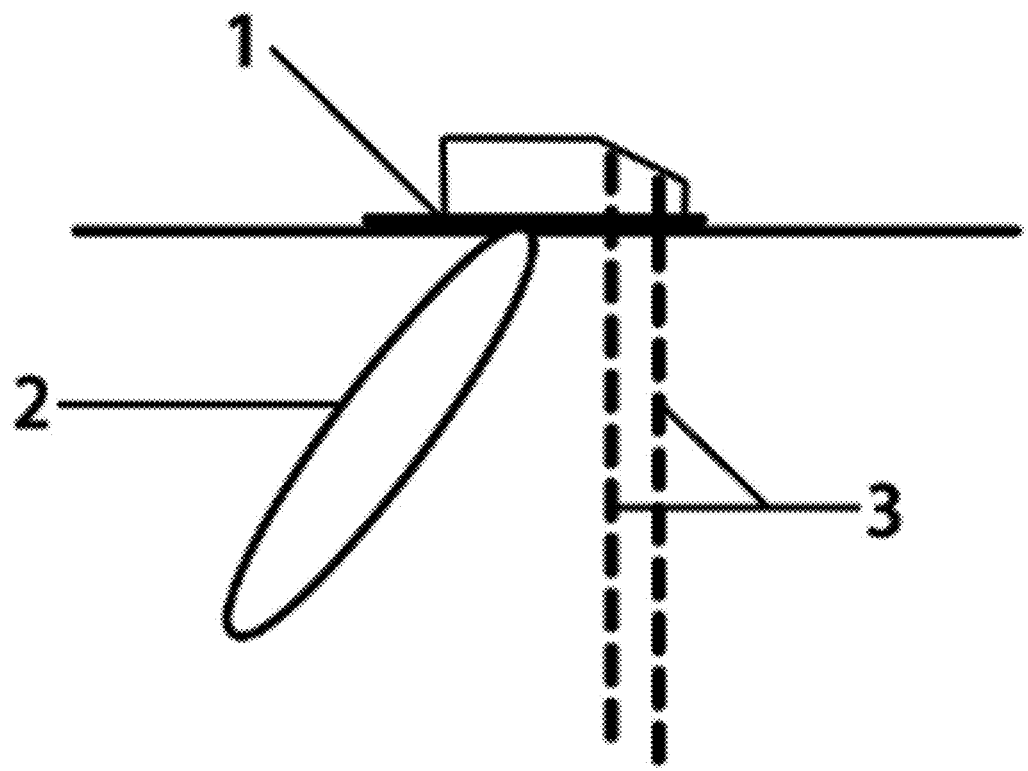

FIG. 23 is a schematic diagram illustrating the wave generation by a transverse wave probe in accordance with the present disclosure.

In the Figure, 1 is surface wave, 2 is transverse wave, and 3 is longitudinal wave.

Figures 1, 24:
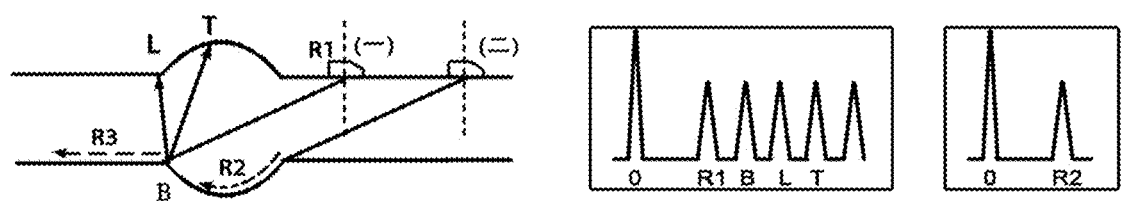
Figures 2, 24:
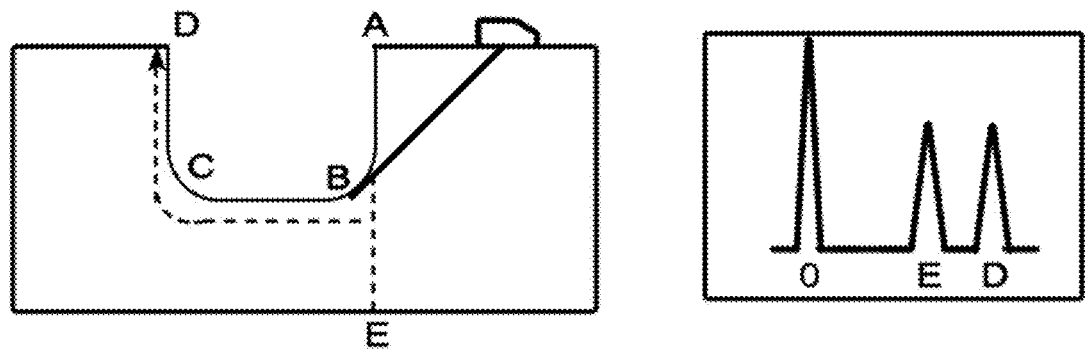
Figures 3, 24:
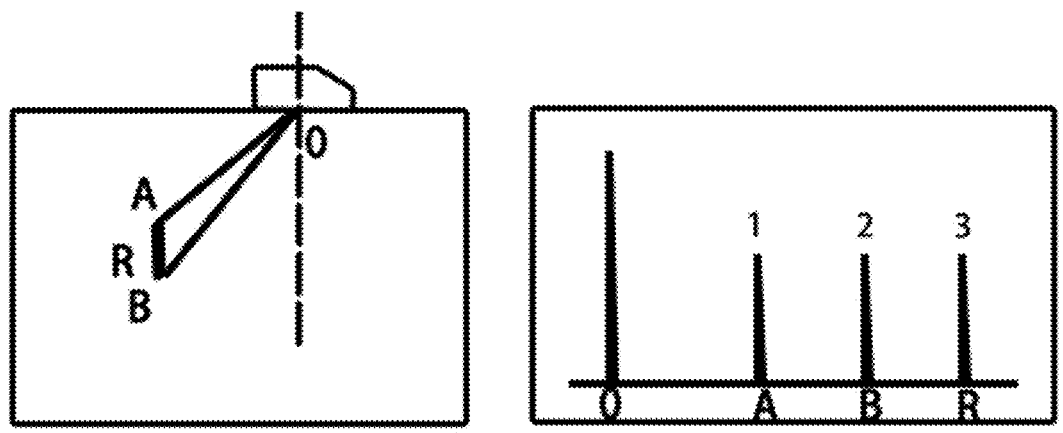

FIG. 24-1 is a schematic diagram illustrating the wave mode conversion in accordance with the present disclosure.

In the Figure, B. bottom wave; T. Transmit and reflected waves; L. Converted longitudinal wave; C. Surface wave direction.

FIG. 24-2 is a schematic diagram illustrating wave mode conversion in accordance with the present disclosure.

In the Figure, E is the reflected wave generated when the transverse wave generated by point B transmits to point E, D stands for the reflected echo generated when the surface wave generated at point B transmits to point D.

FIG. 24-3 is a schematic diagram illustrating wave mode conversion in accordance with the present disclosure.

In the Figure, 1: pulse 1 is the reflected wave at point A of the defect; 2: pulse 2 is the diffracted wave at point B of the defect; 3: pulse 3 is the reflected wave of the surface wave of the surface AB.

Figures 1, 25:
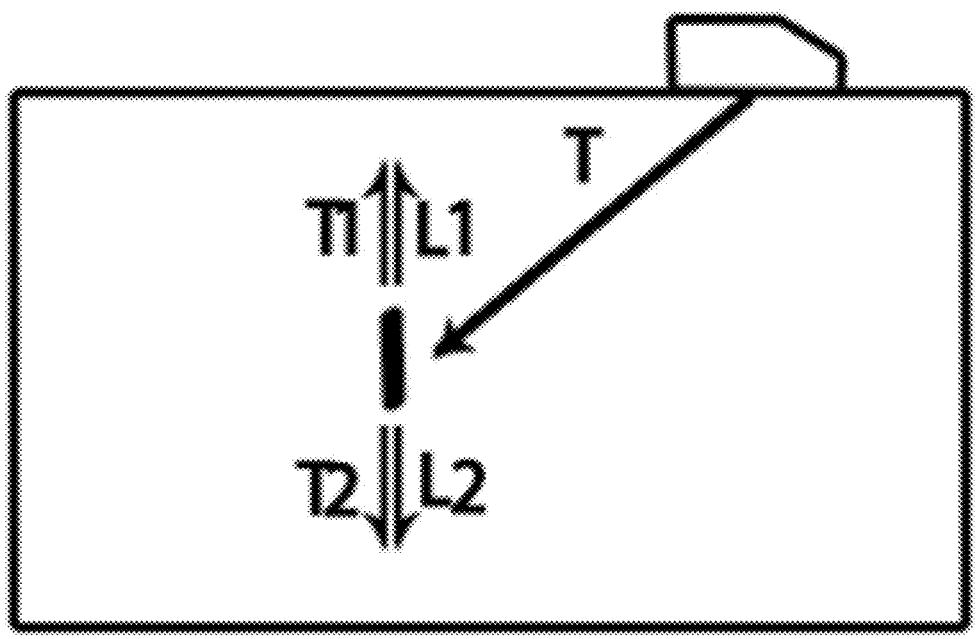
Figures 2, 25:
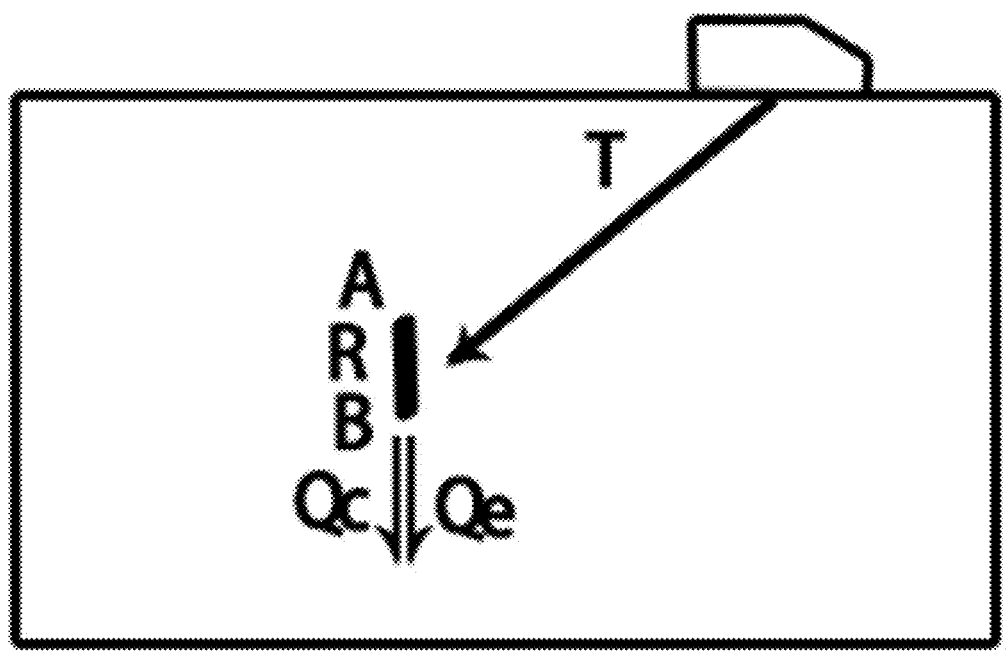
Figures 3, 25:
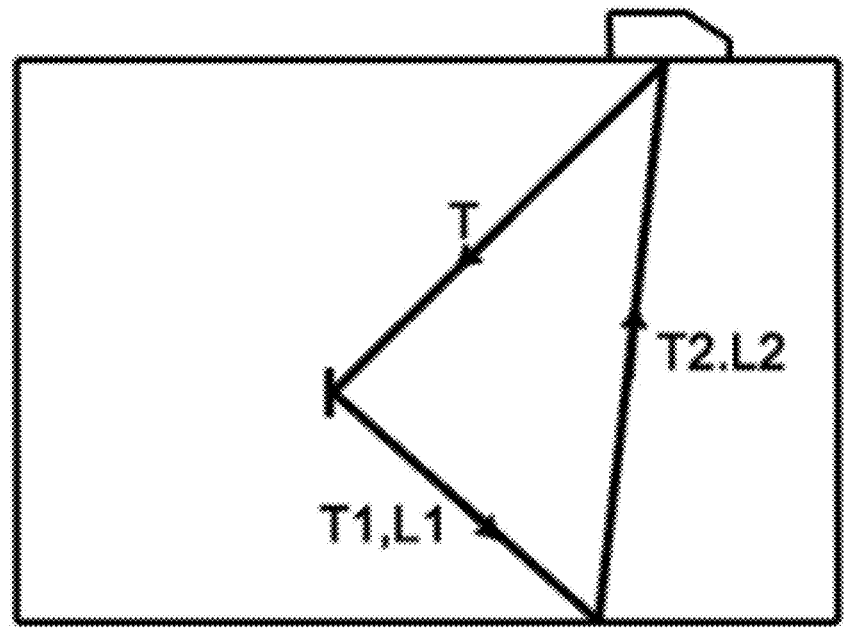
Figures 4, 25:
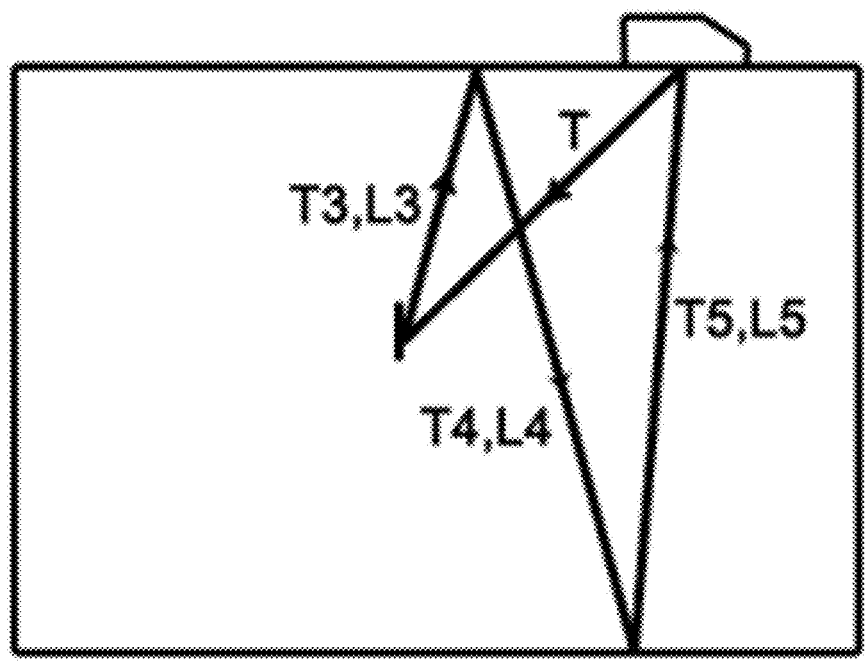
Figures 5, 25:
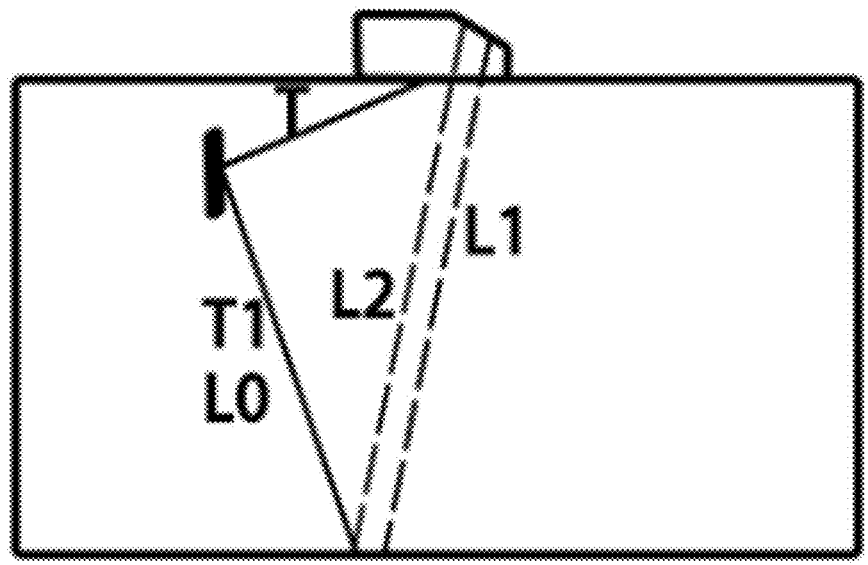
Figures 6, 25:
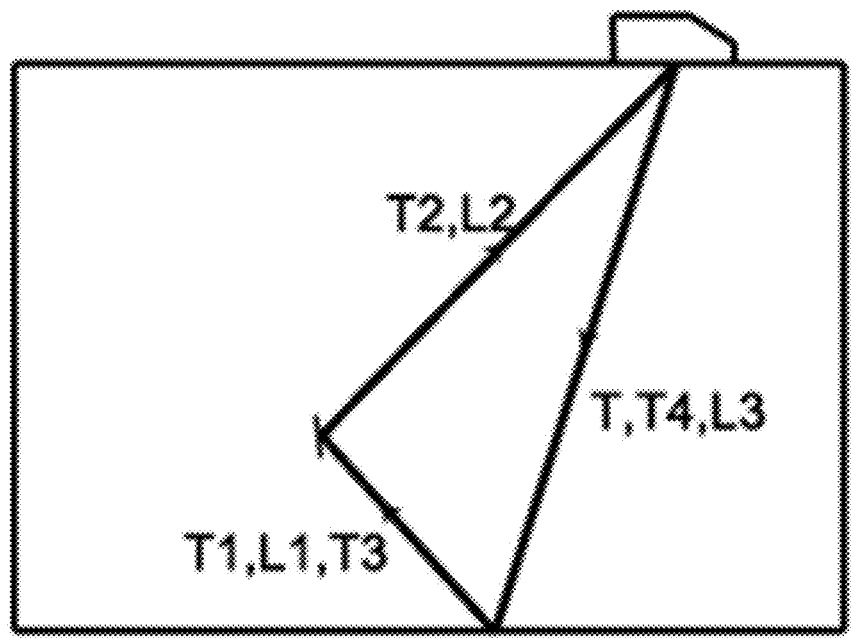
Figures 7, 25:
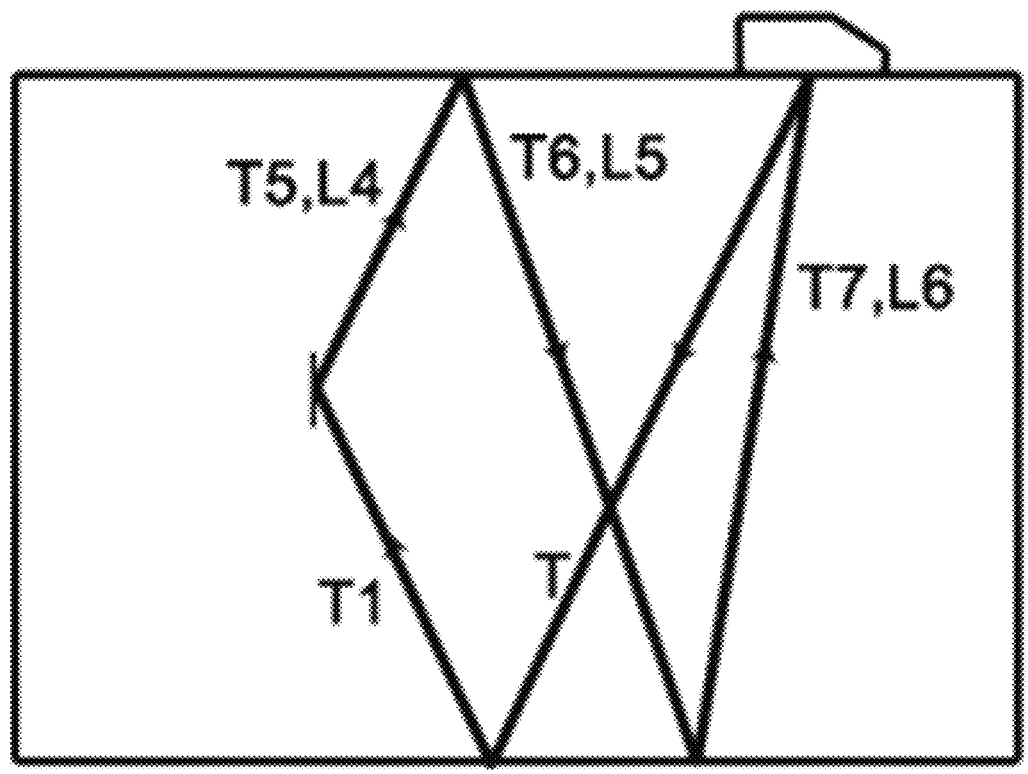
Figures 8, 25:
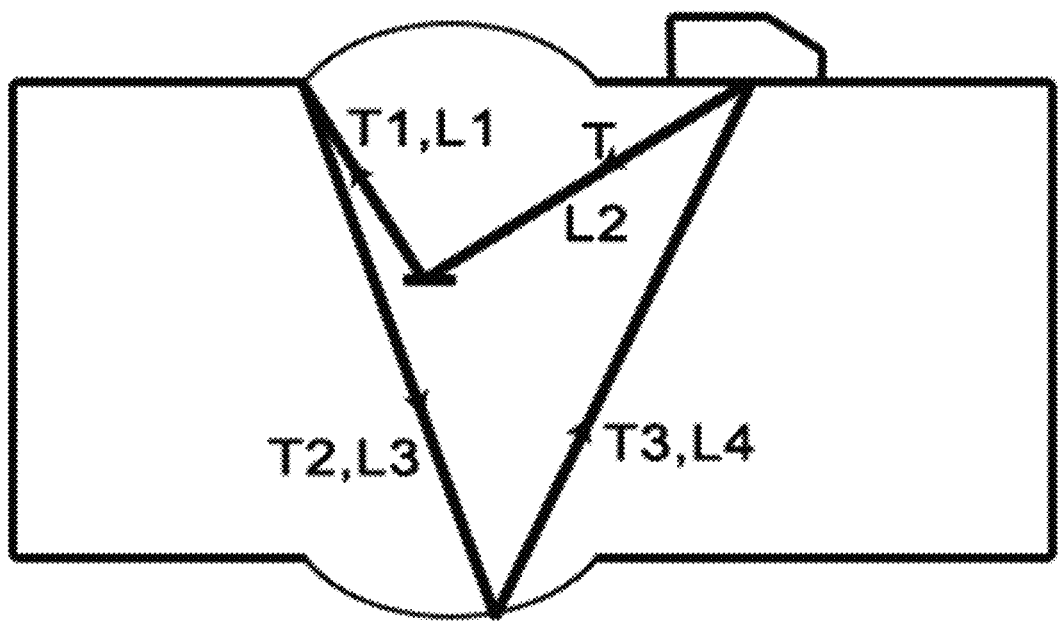
Figures 9, 25:
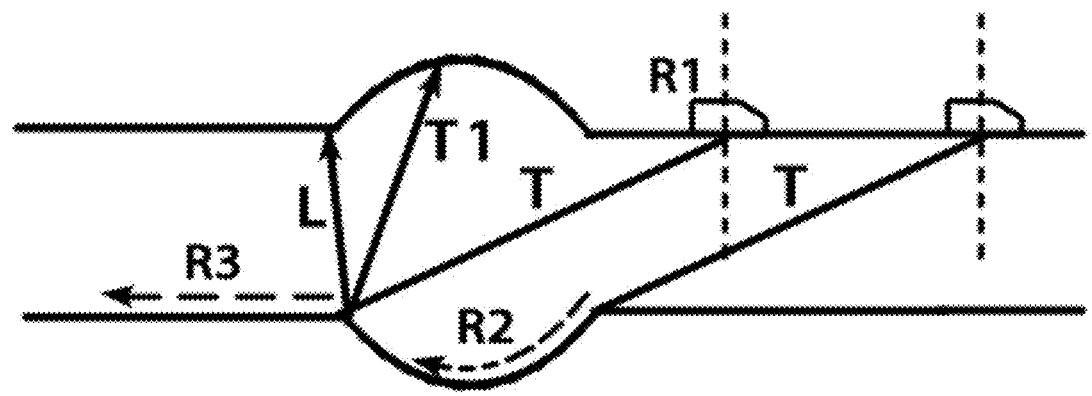
Figures 10, 25:
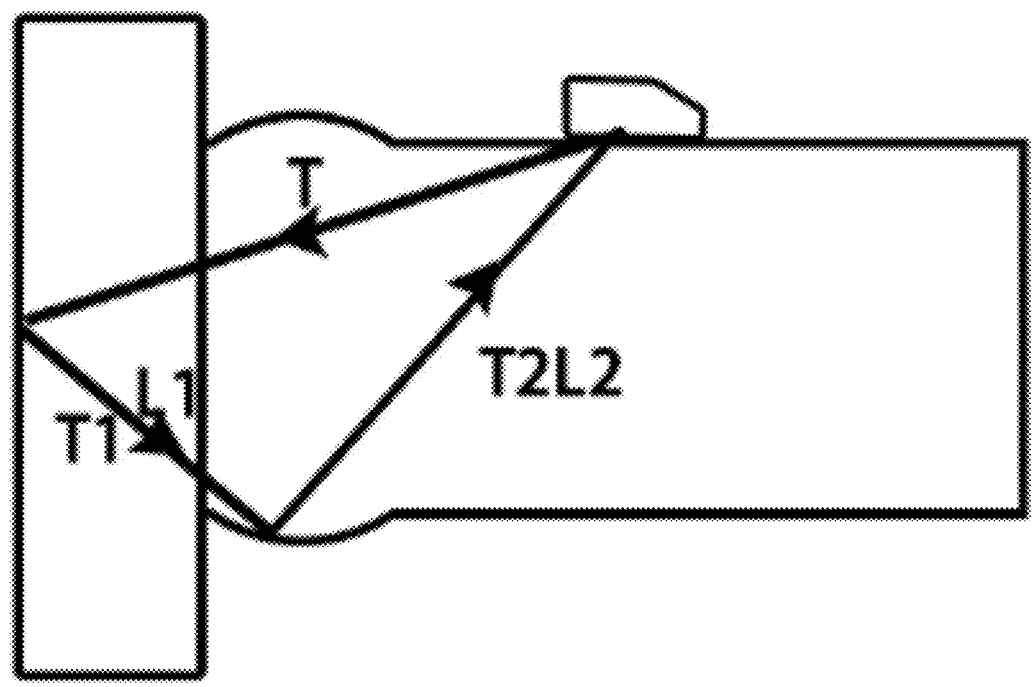
Figures 11, 25:
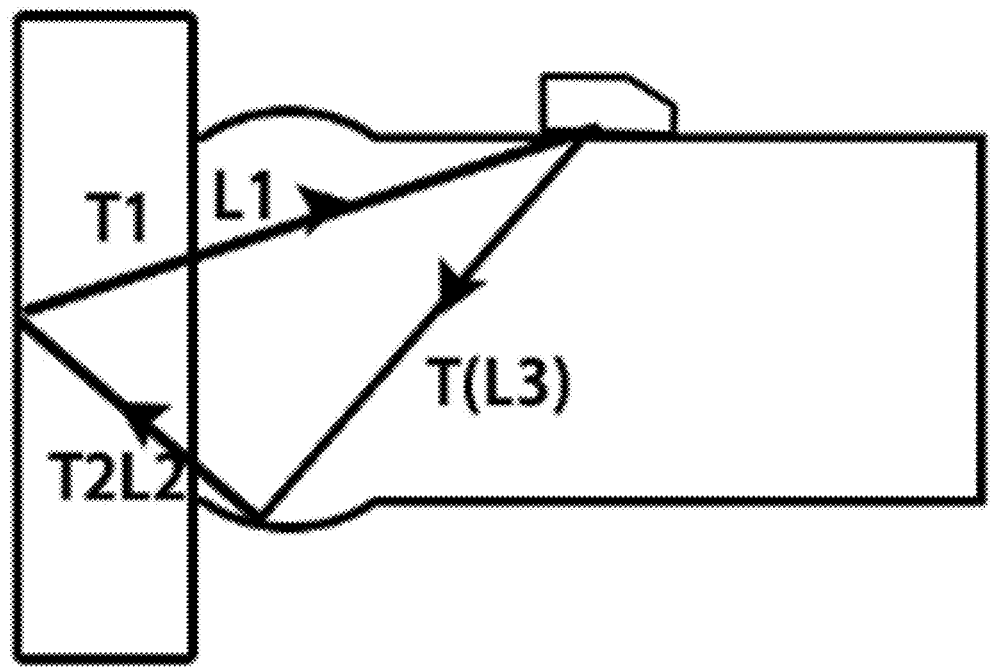
Figures 12, 25:
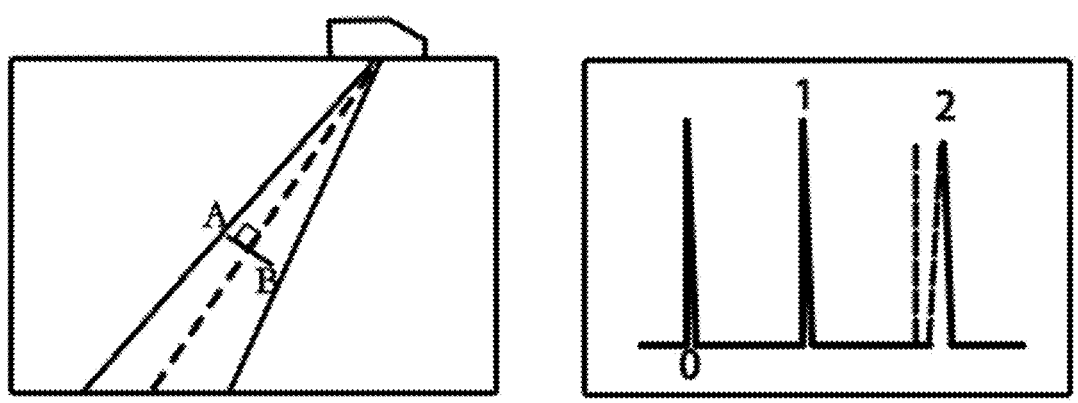
Figures 13, 25:
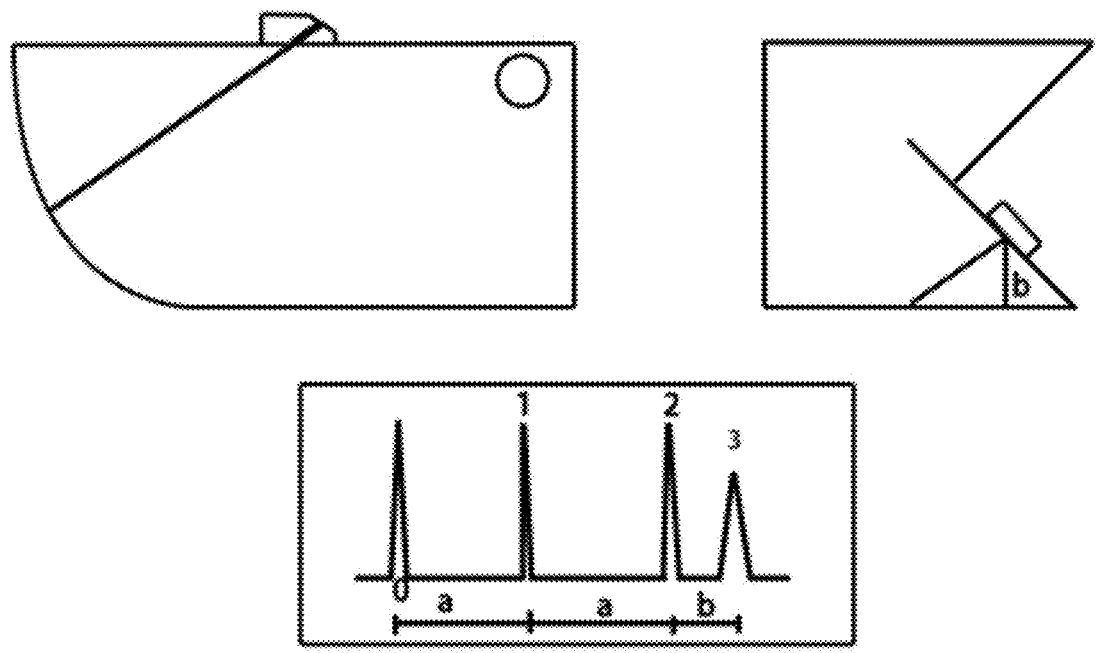

FIG. 25-1 is a schematic diagram illustrating the loop of reflected, diffracted, and deformed waves in primary-wave flaw detection of a defect in accordance with the present disclosure (the first group).

In the Figure, T stands for transverse wave, L stands for longitudinal wave. 1. TT; 2. TT1T1T; 3. TL1L1T; 4. TT2T2T; 5. TL2L2L.

FIG. 25-2 is a schematic diagram illustrating the loop of reflected, diffracted, and deformed waves in primary-wave flaw detection of a defect in accordance with the present disclosure (the second group).

In the Figure, T stands for transverse wave, L stands for longitudinal wave. 1. TT; 2. TAT; 3. TBT; 4. TRT; 5. Ql; 6. Qt.

FIG. 25-3 is a schematic diagram illustrating the loop of reflected, diffracted, and deformed waves in primary-wave flaw detection of a defect in accordance with the present disclosure (the third group).

In the Figure, T stands for transverse wave, L stands for longitudinal wave. 1. TT; 2. TT1T2; 3. TT1L2; 4. TL1T2; 5. TL1L2.

FIG. 25-4 is a schematic diagram illustrating the loop of reflected, diffracted, and deformed waves in primary-wave flaw detection of a defect in accordance with the present disclosure (the third group).

In the Figure, T stands for transverse wave, L stands for longitudinal wave. 1. TT; 2. TT3T4T5; 3. TT3T4L5; 4. TT3L4T5; 5. TT3L4L5; 6. TL3L4L5; 7. TL3L4T5; 8. TL3T4T5; 9. TL3T4L5.

FIG. 25-5 is a schematic diagram illustrating the loop of reflected waves in primary-wave flaw detection of a defect in accordance with the present disclosure (the fourth group).

In the Figure, T stands for transverse wave, L stands for longitudinal wave. 1. TT; 2. TT1L1; 3. TT1L2; 4. TL0L1; 5. 5-TL0L2.

FIG. 25-6 is a schematic diagram illustrating the loop of reflected, diffracted, and deformed waves in secondary-wave flaw detection of a defect in accordance with the present disclosure (the fifth group).

In the Figure, T stands for transverse wave, L stands for longitudinal wave. 1. TT1T1T; 2. TT1T2; 3. TT1L2; 4. TT1L1L3; 5. TT1L1T4; 6. TT1T3L3.

FIG. 25-7 is a schematic diagram illustrating the loop of reflected, diffracted, and deformed waves in secondary-wave flaw detection of a defect in accordance with the present disclosure (the fifth group).

In the Figure, T stands for transverse wave, L stands for longitudinal wave. 1. TT1T1T; 2. TT1T5T6T7; 3. TT1T5T6L6; 4. TT1T5L5L6; 5. TT1T5L5T7; 6. TT1L4L5L6; 7. TT1L4L5T7; 8. TT1L4T6T7; 9. TT1L4T6L6.

FIG. 25-8 is a schematic diagram illustrating the reflected echo when the defect's reflected wave encounters the weld with an enhanced height in accordance with the present disclosure (the sixth group).

In the Figure, T stands for transverse wave, L stands for longitudinal wave. 1. TT1T1T; 2. TT1T1L2; 3. TT1L1L2; 4. TT1L1T; 5. TL1L1L2; 6. TL1T1T; 7. TL1L1T; 8. TL1T1L2; 9. TT1T2T3; 10; TT1T2L4; 11. TT1L3T3; 12. TT1L3L4; 13. TL1T2T3; 14. TL1T2L4; 15. TL1L3T3; 16. TL1L3L4.

FIG. 25-9 is a schematic diagram illustrating the loop of reflected, diffracted, and deformed waves of a weld corner in accordance with the present disclosure (the seventh group).

In the figure, T represents the transverse wave, L represents the longitudinal wave, and R represents the surface wave; 1. R1; the surface wave generated by the transverse wave probe; 2. TT; the reflected echo of the transverse wave by the rear weld corner; 3. TLLT; the deformed longitudinal wave generated by the rear weld corner; 4. TT1T1T; transverse wave reflected echo produced by the rear weld corner; 5. TR3R3T; the echo produced when the deformed surface wave produced by the rear weld corner encounters a plate surface problem, otherwise there would be no echoes when there are not problems; 6. TR2R2T; the deformed surface wave generated by the front weld corner.

FIG. 25-10 is a schematic diagram illustrating the loop of reflected waves of a heterogeneous plate with primary-wave flaw detection of a heterogeneous fillet weld in accordance with the present disclosure (the eighth group).

In the Figure, the heterogeneous fillet weld covers the TKY node, representing various ideas of heterogeneous fillet welds, where the loop of the defect waves in the weld is the same as the previous figures;

T represents a transverse wave, L represents a longitudinal wave; 1, TT; reflected wave of a primary transverse wave; 2, TT1T2; 3, TT1L2; 4, TL1T2; 5, TL1L2.

FIG. 25-11 is a schematic diagram illustrating the loop of reflected waves of a heterogeneous plate with secondary-wave flaw detection of a heterogeneous fillet weld in accordance with the present disclosure (the ninth group).

In the Figure, the heterogeneous fillet weld covers the TKY node, representing various ideas of heterogeneous fillet welds, where the loop of the defect waves in the weld is the same as the previous figures;

In the Figure, T stands for transverse wave, L stands for longitudinal wave. 1. TT1T1T; reflected waves of primary and secondary transverse waves; 2. TT1L1T3; 3. TT1L1L3; 4. TT1L2; 5. TT1T2; 6. TL1L2; 7. TL1T2.

FIG. 25-12 is a schematic diagram illustrating the loop of the secondary-wave perpendicularly reflected by the defect in the weld in accordance with the present disclosure (the tenth group).

In the Figure, 1, pulse 1 is the perpendicular reflecting loop of the primary-wave of the defect surface; 2, pulse 2 is the perpendicular reflecting loop of the primary-wave of the defect surface, of which the spacing is larger than the distance between the wafer in the primary-wave multiple probe and the point of incidence.

FIG. 25-13 is a schematic diagram illustrating the method of measuring the distance between the wafer soundwave transmit center of the oblique probe and the point of incidence of the soundwave of the probe in accordance with the present disclosure.

Figures 1, 26:
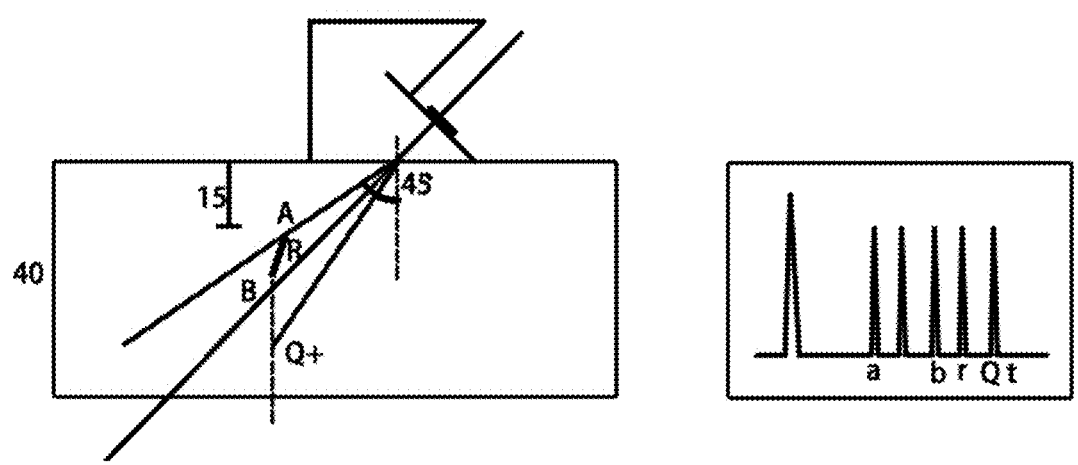
Figures 2, 26:
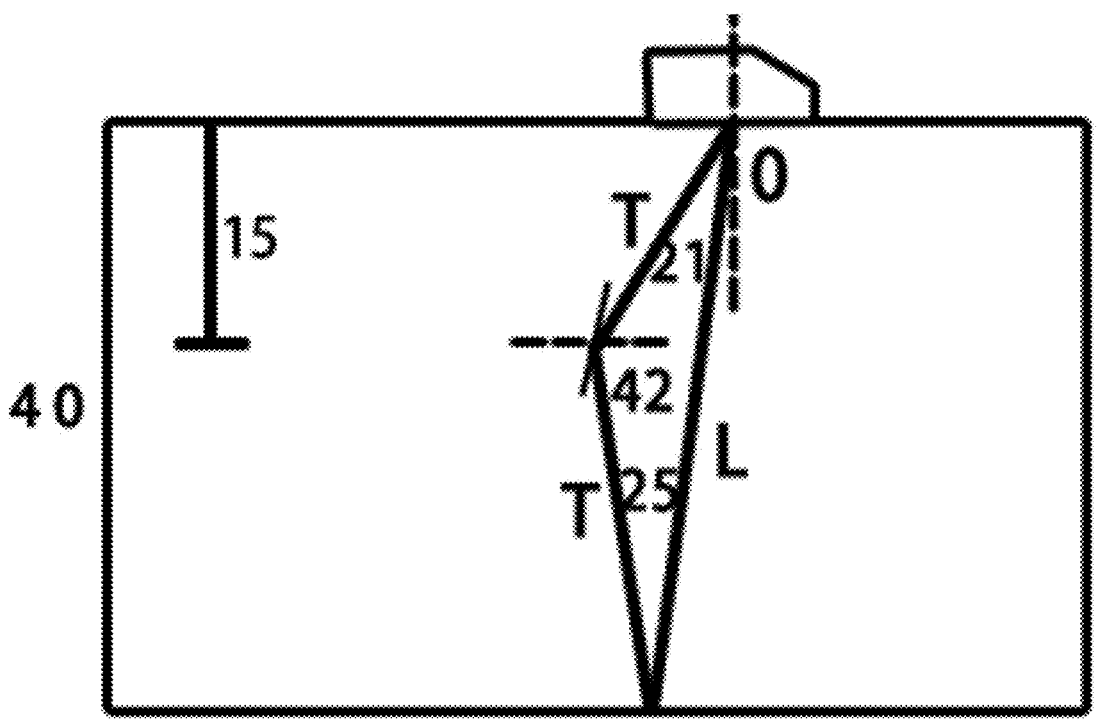
Figures 3, 26:
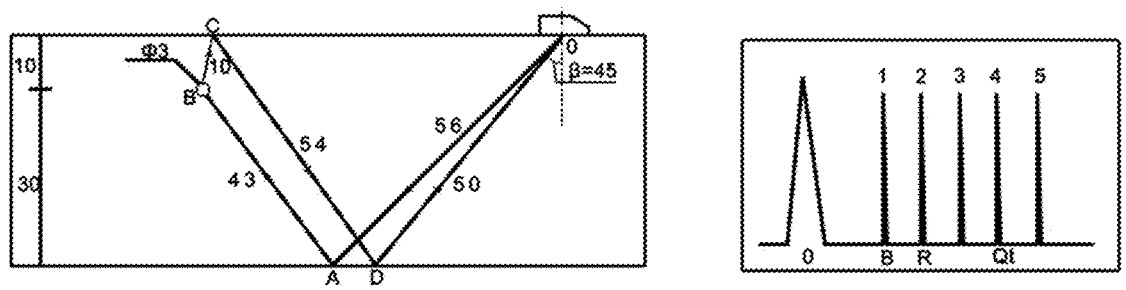

FIG. 26-1 is a schematic diagram illustrating the reflected echo of the defect in primary-wave flaw detection in accordance with the present disclosure.

In the Figure, 1, point A reflected wave of the defect; 2, point B diffracted wave; 3, surface wave of the defect; 4, 24 mm depth display echo; 5, Qt wave.

FIG. 26-2 is a schematic diagram illustrating the reflected echo of the defect in primary-wave flaw detection in accordance with the present disclosure.

FIG. 26-3 is a schematic diagram illustrating the reflected echo of the defect in secondary-wave flaw detection in accordance with the present disclosure.

Figures 1, 27:
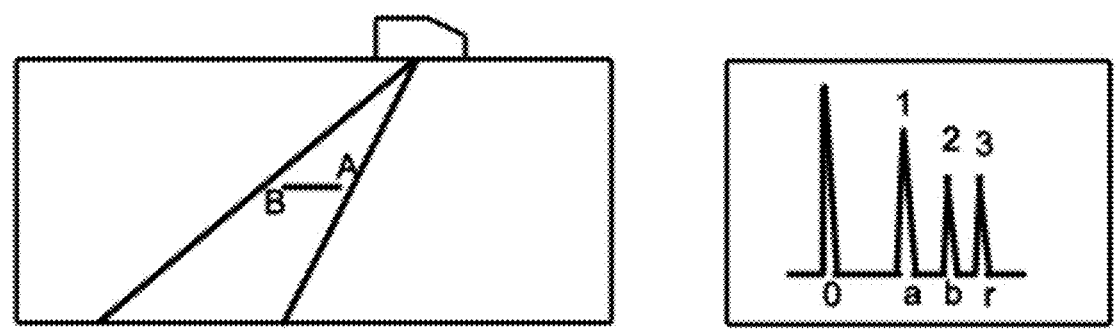
Figures 2, 27:
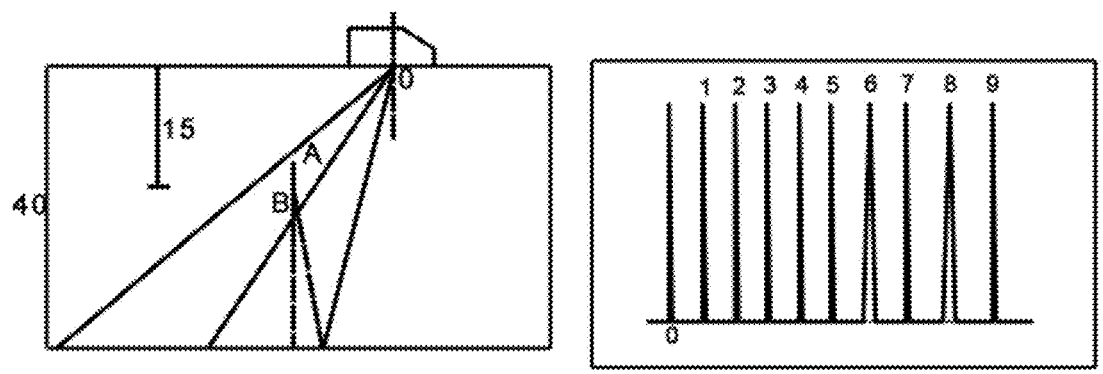

FIG. 27-1 is a schematic diagram illustrating the flaw detection of a horizontal-plane shaped defect in accordance with the present disclosure.

FIG. 27-2 is a schematic diagram illustrating the flaw detection of a vertical-plane shaped defect in accordance with the present disclosure.

Figures 1, 28:
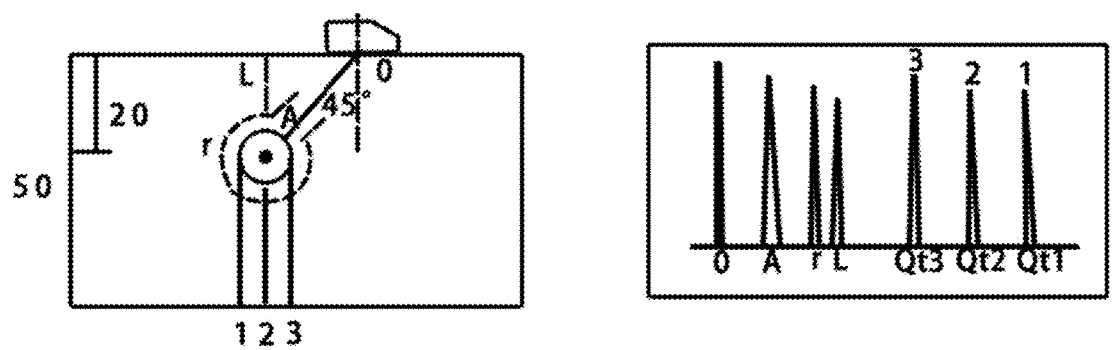
Figures 2, 28:
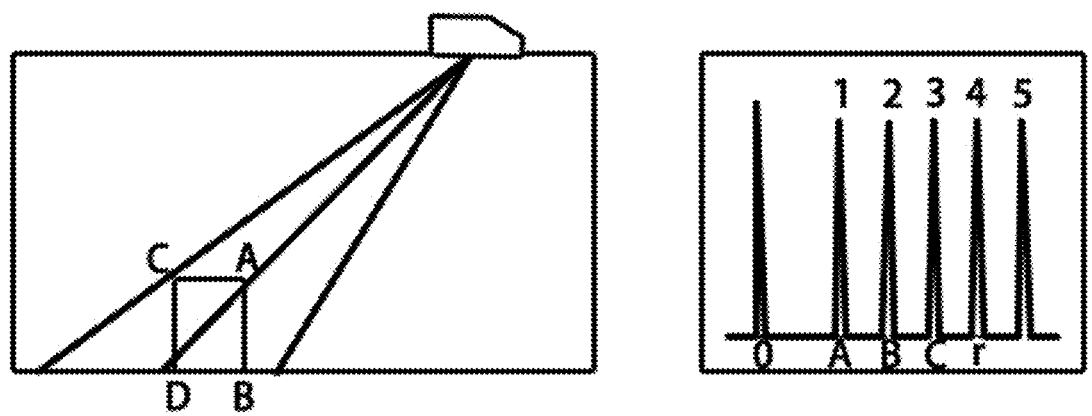
Figures 3, 28:
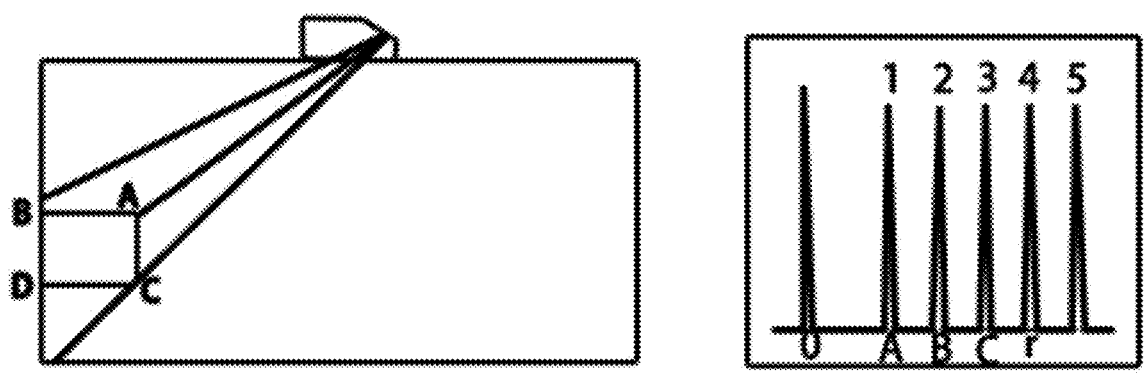

FIG. 28-1 is a schematic diagram illustrating the flaw detection of a transverse through hole a spherical air hole in accordance with the present disclosure.

FIG. 28-2 is a schematic diagram illustrating the flaw detection of a flat bottom hole (vertical detection surface) in accordance with the present disclosure.

FIG. 28-3 is a schematic diagram illustrating the flaw detection of a flat bottom hole (horizontal detection surface) in accordance with the present disclosure.

Figure 29:
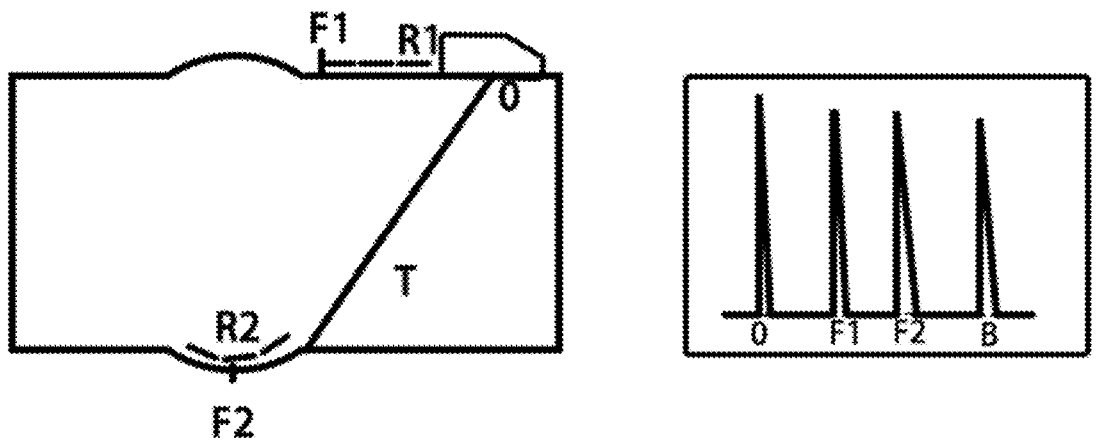

FIG. 29 is a schematic diagram illustrating detecting a weld surface crack using surface waves generated by a weld end corner and detecting a defect on a base material surface of a detection surface using surface waves generated by a transverse wave probe in accordance with the present disclosure.

Figure 30:
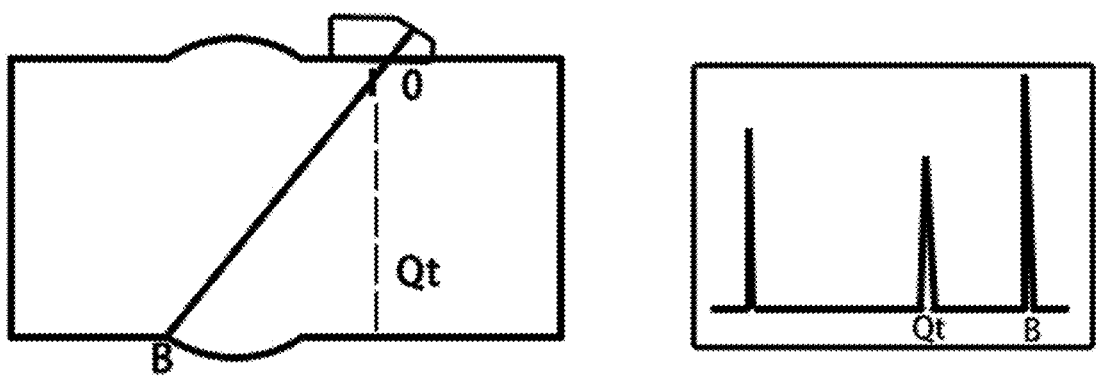

FIG. 30 is a schematic diagram illustrating the correct reflection and wrong judgment in accordance with the present disclosure.

Figure 31:
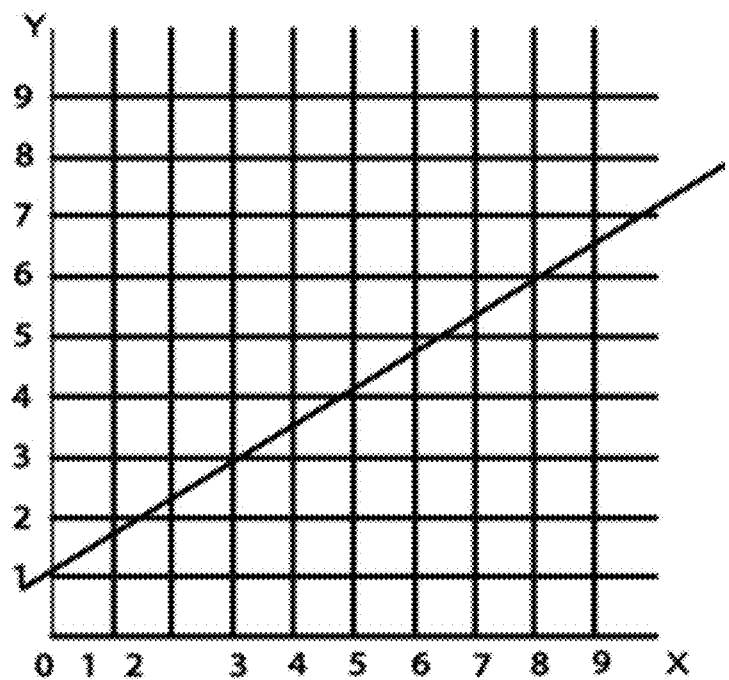

FIG. 31 shows a chart for determining a diameter of a flat bottom hole in transverse wave flaw detection in accordance with the present disclosure.

Figure 32:
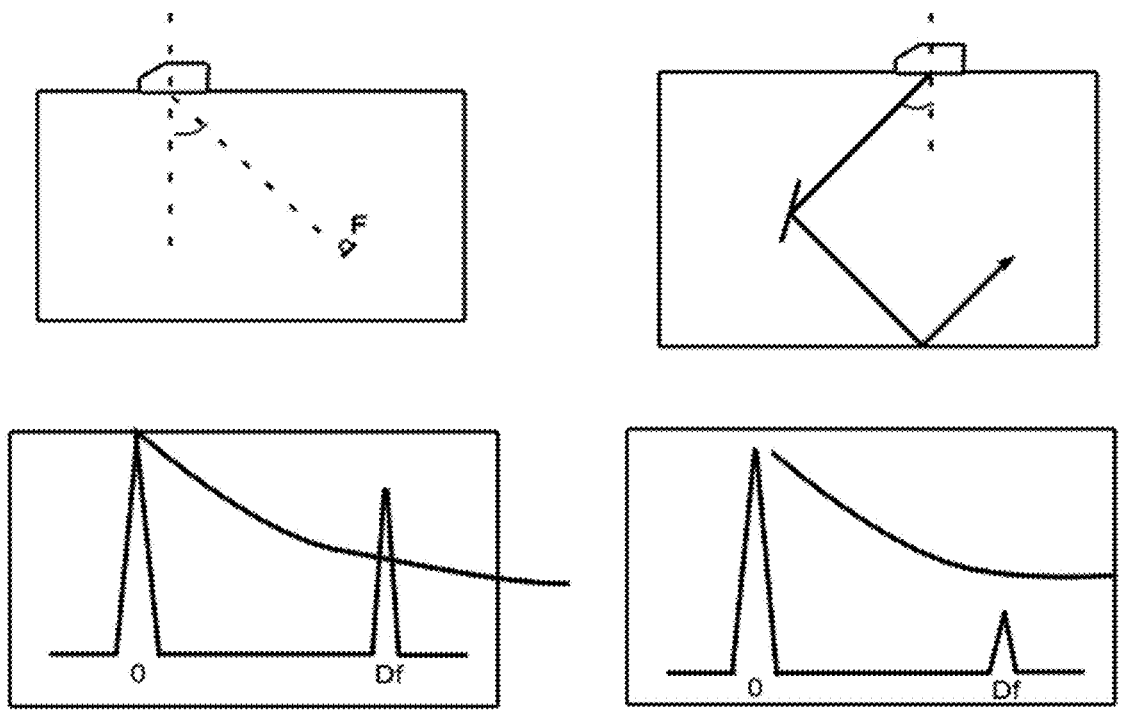

FIG. 32 is a schematic diagram illustrating the reflected echoes of large and big defects in different orientation in accordance with the related art.

Figures 1, 33:
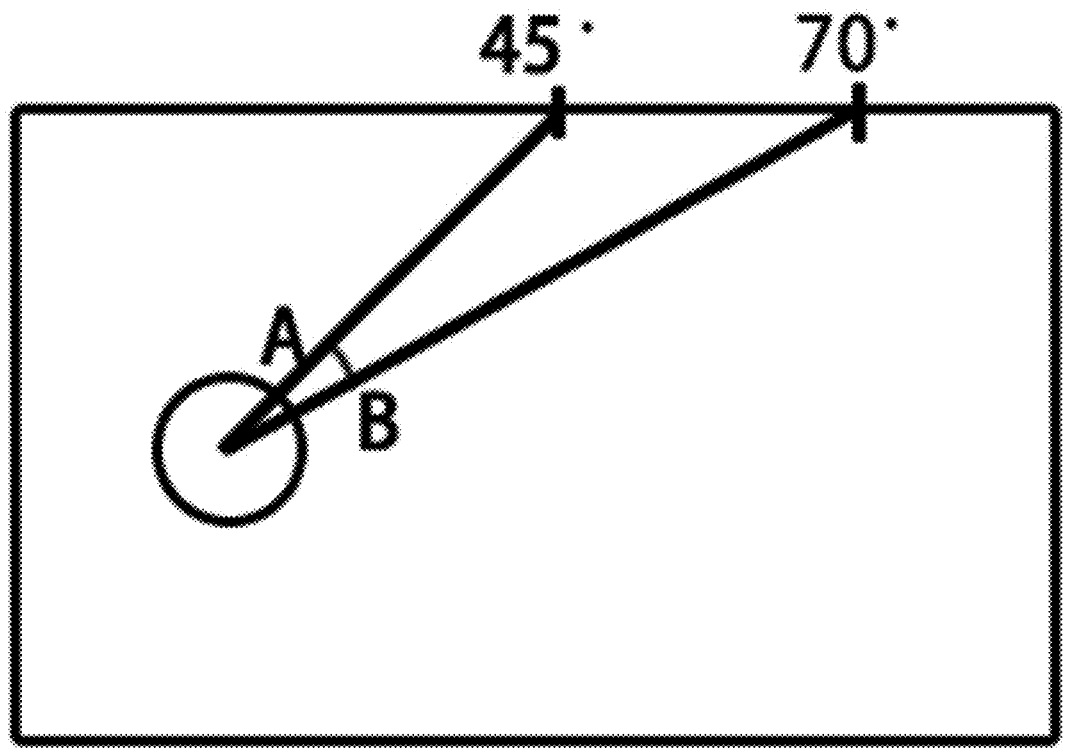
Figures 2, 33:
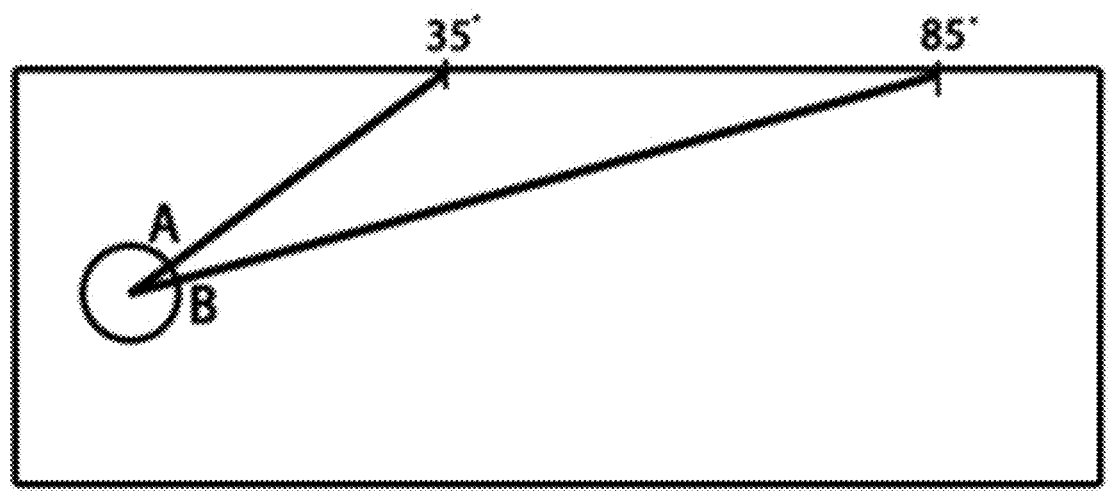

FIG. 33-1 is a schematic diagram illustrating the flaw detection with probes made covering all the angles from 45° to 70°, in circular defects in accordance with the present disclosure.

FIG. 33-2 is a schematic diagram illustrating the flaw detection with probes made covering all the angles from 35° to 85°, in circular defects in accordance with the present disclosure.

Figure 34:
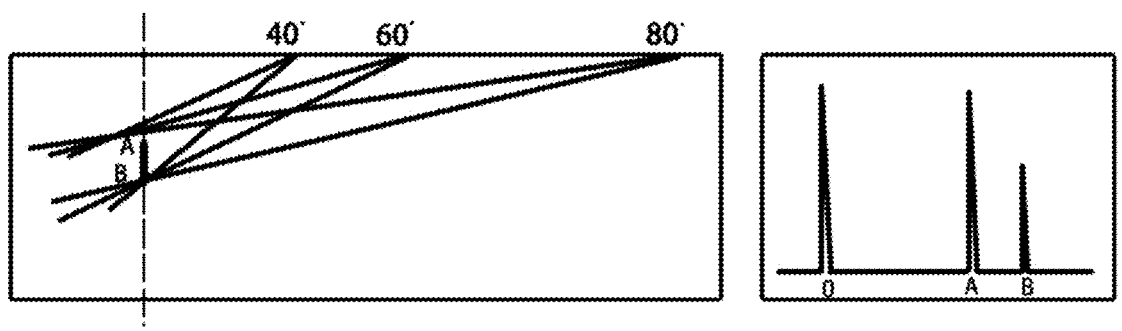

FIG. 34 is a schematic diagram illustrating the flaw detection with probes of all angles using transverse wave, in vertical-plane shaped defect in accordance with the present disclosure.

DETAILED DESCRIPTION

It should be noted that, in the absence of contradiction, the embodiments set forth in the present disclosure and the features in these embodiments can be combined with each other. The present disclosure will be described in detail below with reference to the drawings and embodiments.

In order to make clearer the objectives, technical solutions, and advantages of the embodiments set forth in the present disclosure, the technical solutions embodied in the embodiments of the present disclosure will be clearly and comprehensively described with reference to the accompanying drawings used in the embodiments of the present disclosure. Obviously, the embodiments described herein accounts for merely a part of, rather than all of, the embodiments of the present disclosure. The following description of at least one exemplary embodiment is actually merely illustrative and is in no way intended to limit the present disclosure and its applications or uses. Based on the embodiments of the present disclosure, all other embodiments obtained by a person having ordinary skill in the art without creative efforts shall all fall in the scope of protection of the present disclosure.

It should be noted that the terminology used herein is used for the merely purpose of describing specific embodiments and is not intended to limit the exemplary embodiments set forth in the present disclosure. As used herein, the singular forms are intended to include the plural forms as well, unless the context clearly indicates otherwise, and it should also be understood that when the terms "comprising" and/or "including" are used in this specification, they indicate the presence of features, steps, operations, devices, components, and/or combinations thereof.

Unless specifically stated otherwise, the relative arrangement of the components and steps, numerical expressions, and numerical values set forth in these embodiments do not limit the scope of the present disclosure. At the same time, it should be clear that, for the convenience of description, the dimensions of the various parts shown in the drawings are not drawn according to the actual proportional relationships. Techniques, methods, and equipment known to those having ordinary skill in the relevant field may not be discussed in detail, but where appropriate, the techniques, methods, and equipment should be considered as part of the authorized specification. In all examples shown and discussed herein, any specific value should be construed as exemplary only and not as a limitation. Therefore, other examples of the exemplary embodiments may have different values. It should be noted that similar reference numerals and letters indicate similar items in the following drawings, so once an item is defined in one drawing, it need not be discussed further in subsequent drawings.

In the description of the present disclosure, it should be understood that the orientational words such as "front, back, up, down, left, right", "transverse, vertical, perpendicular, horizontal", "top, bottom" and the like which indicate the orientational or the positional relationships are usually based on the orientational or positional relationship shown in the drawings, which are merely intended for the convenience of describing the present disclosure and simplifying the description. Unless otherwise stated, these orientational words do not indicate and imply that the device or element referred to must bear a specific orientation or be constructed and operated in a specific orientation, so it should not be understood as a limitation on the scope of protection of the present disclosure, where in particular the orientational words "inside and outside" refer to the inside and outside relative to the outline of each component itself.

For the convenience of description, spatially relative terms such as "above", "on the top of", "on the upper surface of", "upper", etc. can be used here to describe the spatial positional relationship between one component or feature and another component or feature shown in the drawings. It should be understood that spatially relative terms are intended to encompass different orientations in use or operation in addition to the orientation of the component as described in the figures. For example, if a component in the figure is turned over, components described as "above" or "on the top of" another component or construction will be positioned "below the other component or construction" or "under the other component or construction". Thus, the exemplary term "above" may include both orientations "above" and "below". The component can also be positioned in other different ways (rotated 90 degrees or at other orientations), and the relative spatial description used here is explained accordingly.

In addition, it should be noted that the use of words such as "first" and "second" to limit parts is intended for the mere purpose of convenience of distinguishing the corresponding parts. Unless otherwise stated, the above terms have no special meaning and cannot be understood to be limiting the scope of protection of the present disclosure.

As illustrated in the drawings, the present disclosure provides a reflection-diffraction-deformation flaw detection method with a transverse wave oblique probe in accordance with the present disclosure. The method includes the following operations.

When an ultrasonic transverse wave encounters a defect during propagation, it can generate a reflected wave, a diffracted wave, and a deformed wave. Through a comprehensive analysis of these waves, the presence or absence of the defect is determined by the reflected wave having reflection characteristics and the diffracted wave having the diffraction characteristics. The shape and size of the defect are determined by the deformed wave having deformation characteristics, namely the deformed surface wave generated at the endpoints of the defect which propagates on the defect surface. Furthermore, by the combination of paths trailed by the deformed surface wave, the deformed transverse wave, and the deformed longitudinal wave that are generated by the defect as well as that trailed by the transmit transverse wave, causes of all those waves in the screen can be revealed, thereby realizing the precise positioning, quantification and characterization of the defect, enabling the three-dimensional rendering of the truthful shape of the defect relying solely on A-ultrasound technology.

In the ultrasonic flaw detection process, first a primary-wave flaw detection is performed on one side. When a defect is encountered, a defect waveform A will appear. The defect waveform A includes at least one or more selected from the group consisting of a reflected wave, a diffracted wave, and a deformed wave. When a secondary-wave flaw detection is used and a defect is encountered, a defect waveform B will appear, which includes at least one or more selected from the group consisting of a reflected wave, a diffracted wave, and a deformed wave.

Secondly, when a primary-wave flaw detection is performed on the other side and a defect is encountered, then a defect waveform C will appear which includes at least one or more selected from the group consisting of a reflected wave, a diffracted wave, and a deformed wave. When a secondary-wave flaw detection is used and a defect is encountered, then a defect waveform D will appear which includes at least one or more selected from the group consisting of a reflected wave, a diffracted wave, and a deformed wave.

When defect waveform A and defect waveform B, or defect waveform C and defect waveform D are exactly the same, then the defect is symmetrical up and down on one side; otherwise when defect waveform A and defect waveform C, or defect waveform B and defect waveform D are exactly the same, then the defect is symmetrical left and right on both sides.

Thereby, the reflection-diffraction-deformation flaw detection method using a transverse wave oblique probe is enabled employing the combined flaw detection with the ultrasonic primary-wave and ultrasonic secondary-wave and waves of even higher orders at the two sides of the weld, which essentially combines the reflected wave, the diffracted wave and the deformed wave that are generated by the defect. Some defects can be accurately positioned, quantified, and characterized by presence of the defect's reflected wave, diffracted wave, and deformed wave, after performing a primary-wave flaw detection on one side. Some defects can be accurately positioned, quantified, and characterized by presence of the defect's reflected wave, diffracted wave, and deformed wave, after performing a secondary-wave flaw detection on one side. Likewise, Some defects can be accurately positioned, quantified, and characterized by presence of the defect's reflected wave, diffracted wave, and deformed wave, after performing a primary-wave flaw detection on the other side, or can be accurately positioned, quantified, and characterized by presence of the defect's reflected wave, diffracted wave, and deformed wave, after performing a secondary-wave flaw detection. The results of each flaw detection can be verified against each other. The method includes the following operations.

S1. Determination of flaw detection sensitivity: The sensitivity of the reflection-diffraction-deformation flaw detection method is based on the existing Φ3 mm transverse through-hole sensitivity, which is so increased by more than 10 dB that it does not affect the flaw detection; or uses the Φ0.5 mm transverse through-hole as the initial sensitivity, alternatively, the sensitivity can also be determined according to the smallest defect allowed by design requirements. Different products have different requirements for the type and size of the defect, so the sensitivity is also different. The determination of sensitivity is based on the detection of the smallest defect. After the defect is found, the assessment of the defect is not based on sensitivity, but on the reflected-diffracted-deformed waves of the defect. When the reflected wave of the defect is relatively low, the sensitivity needs to be promoted. When the defect has only one reflected wave, the sensitivity needs to be lifted so as to make the reflected wave, the diffracted wave, and the deformed wave of the defect appear at the same time. When the reflected wave, the diffracted wave, and the deformed wave of the defect are relatively high thus affecting the judgement, then the sensitivity should be appropriately reduced so that it doesn't affect the judgment.

S2. Determination of the probe angle. In the reflection-diffraction-deformation flaw detection method, the selection of the probe angle is independent of the groove bevel angle of the weld, and is unrelated to the thickness of the plate. It is associated with the ability of uncovering and assessing defects. Only one probe angle is selected, namely 45° transverse wave oblique probe. If the detection with the 45° transverse wave oblique probe leads to unpenetrated zones (dead zones) on the detection site, then probes at other angles are all used for compensation or for auxiliary flaw detection. Regarding special welds and special defects, special probes may need to be made.

S3. Determination of the type and size of the defect: the defects are composed of plane defects, circular and semi-circular defects, and volume defects.

In step S3, the types of the plane defect includes the following cases: the plane defect is parallel to the detection surface, the plane defect is perpendicular to the detection surface, the plane defect is inclined from being perpendicular to the detection surface to the probe side, and the plane defect is inclined from being perpendicular to the detection surface to the opposite side of the probe side. The types of flaw detection for circular and semi-circular defects include: spherical air hole inspection, transverse through-hole inspection, flat-bottom inspection, and semi-circular defect inspection. Types of polygonal defect consisting of planar shapes include: triangular defects, quadrilateral defects, and hexagonal defect detection.

S4. Measurement of length of the defect: 6 dB method and 15°-45° rotation reflection-diffraction-deformation method are employed to measure the length. In step S4, when the length defect needs to be measured, it is first checked whether the length direction of the defect is regular. If the reflected, diffracted, and deformed waves to the endpoints are all the same, then 6 dB method is used to measure the length. If the reflected, diffracted, and deformed waves to the endpoints are different, the 6 dB is used to measure the endpoints, then the probe is tilted 15°-45° and moved to aim at different endpoints, so as to find out the reflected, diffracted, and deformed waves of the endpoints. Then measurements are performed on both sides of the weld and the measured longest point is taken.

S5. Positioning of the defect: After the size and shape of the defect are determined, the defect can be relatively accurately positioned on all directions, including up, down, left, and right.

S6: Characterization of the defect, after the shape and position of the defect are determined, the defect can be characterized at the same time.

In addition to the reflected, diffracted, and deformed waves generated by the defect, the reflected waves and deformed waves generated by the weld corners are used to evaluate the quality of the weld formation, and to assess the presence of defects on the surface and near-surface of the weld. The equivalent method considers that the reflected wave appearing in front of the weld corner reflected wave is determined as a defect's reflected wave, and the wave appearing after the weld corner reflected wave is not considered. Because the reflected waves and deformed waves and multiple reflected waves generated by the weld corners are regular, the reflection-diffraction-deformation flaw detection method with the transverse wave oblique probe believes that of the waves appearing behind the reflected waves of the weld corners are not regular, they would be considered as defects, and all the waves appearing on the scanning line must be analyzed.

The endpoint of the defect generates a surface wave under the action of a transverse wave. The surface wave propagates along the defect surface. When it encounters a corner, reflection happens. The size of the defect surface is calculated based on the position of the reflected wave. After the surface wave is reflected at the corner, it will continue to propagate around the polyhedron for a full cycle to generate circumferential echoes. These combined are the shape of the defect, and can be verified against each other.

After the defect is found by the transverse wave, the reflected wave, diffracted wave and deformed wave from the defect, together with the reflected wave from the weld corners, will form specific reflection loops. These loops can be mapped or programmed into software so as to confirm the generation of each reflected echo appearing in the weld flaw detection screen.

Using the reflection-diffraction-deformation flaw detection method to specify the return paths of the defect wave. And by plotting, all the reflected pulses appearing on the screen, totaling 77+2Q echoes, are analyzed to determine how all reflected pulses are generated. Although the 77+2Q echoes don't actually appear at the same time, all the reflected pulses appearing would not fall out of the principle of generation of the 77+2Q echoes. The formation of the 77+2Q echoes is related to the formation of the weld and the shape and location of the defect. The 77+2Q echoes don't include multiple reflections at one location.

The reflected pulses generated by different sound velocities and different paths on the screen are processed by software and displayed in different colors. A normal transverse wave is set to one color, a longitudinal wave to one color, a surface wave to one color, a transverse to longitudinal transition is set to one color, a longitudinal to transverse transition is set to one color. Similarly, a transverse to surface transition, a surface to longitudinal transition, a surface to transverse transition all have their respective set colors, and combinations of these colors. Which enables the observation to be more intuitive. The pulses are processed by software to be displayed in a line to reduce the blind zone impact caused by the pulse width. According to the position where the reflected, diffracted, and deformed waves show up, the three-dimensional shape and size of the defect are displayed on the screen through software processing.

Surface wave can propagate on the surface of the workpiece. The size and shape of the surface of the workpiece can be determined by reflection. The surface wave cannot propagate inside the medium, and the defect is inside the medium. So can we let the defect obtain the surface wave while the defect is found during the propagation of the transverse wave of the transverse wave oblique probe, such that the surface wave propagates on the surface of the defect. Further, if the defect inside the medium can capture the surface wave, how can we determine whether there is a surface wave among the many waves on the screen and which is the surface wave. In particular, these many waves include reflected transverse waves, reflected longitudinal waves, as well as diffracted waves, and various deformed waves. These waves have the same "look", and each wave has a different origin. So it is only hopeful to determine the shape of the defect by recognizing and distinguishing these waves and learning about and determining the generation and propagation paths of these waves so as to perform an overall determination of at least two of these waves.

When an ultrasonic wave is obliquely incident on the interface between two different media, in addition to generating reflected wave and diffracted wave of the same type, there would also generate reflected wave and diffracted wave of different types. Such phenomenon is referred to as wave mode conversion, as illustrated in FIG. 8, which shows a schematic diagram illustrating the wave mode conversion. The various reflections and refractions of longitudinal wave and transverse wave in FIG. 8 and the wave mode conversion all conform to the laws of reflection and refraction, namely, Snell's law, which are expressed by formulas, namely formula (1) and formula (2).

$$\frac{\sin\alpha_s}{C_{s1}} = \frac{\sin\alpha'_s}{C_{s1}} = \frac{\sin\alpha'_L}{C_{L1}} = \frac{\sin\beta_L}{C_{L2}} = \frac{\sin\beta_s}{C_{S2}} \quad \text{Formula (1)}$$

$$\frac{\sin\alpha_L}{C_{L1}} = \frac{\sin\alpha'_L}{C_{L1}} = \frac{\sin\alpha'_s}{C_{s1}} = \frac{\sin\beta_L}{C_{L2}} = \frac{\sin\beta_s}{C_{S2}} \quad \text{Formula (2)}$$

Snell's law regards the reflection, refraction, and wave mode conversion of longitudinal and transverse waves, excluding surface waves, because surface waves cannot propagate internally, they can only propagate on the surface. When the incident angle of the probe is greater than or equal to 57.7° (second critical angle), the refraction angle of the transverse wave is greater than or equal to 90°, as shown in FIG. 9, which is a schematic diagram of the second critical angle surface wave.

This "transverse wave" propagates on the surface, and this wave that propagates on the surface is called a surface wave. When the transverse wave oblique probe comes into contact with a surface, the wave that enters the other medium is a transverse wave. When the transverse wave oblique probe comes into contact with the medium instead of a surface contact but a point or line contact, then a surface wave is generated, and the surface wave propagates on the surfaces of the medium with different shapes. The propagation of longitudinal and transverse waves conforms to Snell's law, so does surface wave conform to the Snell's law? Snell's law is based on the conversion of angle and speed of sound without considering the wave shape. An experiment is conducted to verify the suitability of Snell's law for surface waves. As shown in FIG. 10, which shows a schematic diagram of an artificial defect test block.

FIG. 10 shows artificial defects of different shapes processed on a test piece, a, representing a plane defect, b, representing a triangular defect, c, being a hexagon, representing a polygonal defect, and d, representing a circular defect. The shaded part on 10 represents the shape of the defect, and the shaded part is taken out. After the a-shaped defect is taken out, it is equivalent to a thin steel sheet, which represents the plane defect. Then, the transverse wave oblique probes of 45°, 60°, and 70° are respectively placed on the top (endpoint) of the steel sheet, where the top is a line. The scanning line of the instrument indicates the adjustment according to the angle and depth of the probe. When the transverse wave oblique probe moves back and forth on the top of the steel sheet, as shown in FIG. 11-1, which shows a schematic diagram of surface wave detection steel sheet with a transverse wave probe.

Two reflected waves appear, both of which are reflections from the end corner A at the bottom of the steel sheet. Find the highest wave of the previous reflected wave, keep the probe still, slide your finger on the side of the steel sheet. When the finger reaches a certain position, the reflected wave Ar beats with the finger. This is a surface wave, which proves that the incident point of the transverse wave oblique probe generates a refracted surface wave at the endpoint of the steel sheet, and the surface wave propagates on the surface at a certain angle. By measuring the surface wave refraction angle of the 45° probe is about 41°, the highest wave of the latter wave is found, which is actually measured as the 45° refracted transverse wave. Similarly, the surface wave refraction angle of a 60° probe is about 54°, accompanied by a 60° refracted transverse wave. The surface wave refraction angle of a 70° probe is about 61°, accompanied by a 70° refracted transverse wave. In the above, the surface wave energy is all higher than the transverse wave.

According to Snell's law, the formula $\sin \beta s/Cs = \sin \beta r/Cr$ is used for the calculation, where:

$\beta s$—Transverse wave refraction angle; (45°, 60°, 70°)
$\beta r$—Refraction angle of surface wave; (41°, 54°, 61°)
Cs—the sound velocity of the transverse wave in the medium; (3230 m/s)
Cs—the sound velocity of the surface wave in the medium; (2980 m/s)

The calculation results are basically consistent with the actual measurement results. It is proved through experiments that the surface waves also enter the steel sheet while the surface waves are generated. A wave At that appears near the surface wave is a reflected wave of the transverse wave. Also, because the energy of the incoming transverse wave is small, the reflected wave of the transverse wave is relatively low at this time. The transverse wave oblique probe does not move, and the steel sheet is rotated 90°, as shown in FIG. 11-2, which shows a schematic diagram of the surface wave detection steel sheet of the transverse wave oblique probe with the steel sheet rotated 90°.

The probe is perpendicular to the length of the steel sheet, the incident point is in contact with the endpoint of the steel sheet, and a surface wave is generated at the endpoint. Find the highest reflected wave, the surface wave propagates on the surface of the steel sheet, and the sound path is 1.08 times that of the transverse wave (3230÷ 2980≈1.08). The contact point between the steel sheet and the probe does not move, and the steel sheet is lowered and swayed. As a result, the position of the reflected wave does not change, but the height changes. The forward sway of the steel sheet leads to an increase of the height of the reflected wave, and the backward sway of the steel sheet leads a decreased height of the reflected wave. After taking out the shaded part of the b-shaped defect, it is a triangle, which is likened to a triangular defect. Then place the probe on any vertex of the triangle to generate a surface wave, as shown in FIG. 12, which is a schematic diagram illustrating the detection of a triangle with surface wave of a transverse wave oblique probe.

The reflected waves OA, OB, OABO and OBAO, and OAB and OBA in the screen respectively represent the reflected waves of the propagating from the left and right directions of the surface wave, and their respective echoes that propagate a full circumference. There are two more reflected waves, one is the BO reflected wave from OABO, and the other is the AO reflected wave from OBAO. The distance of each reflected wave on the screen represents the side length and perimeter of the triangle. Knowing the length of the three sides of the triangle, then the shape of the triangle is known. At this time, the transverse wave also enters the triangular workpiece through the vertices, and there is also reflection, but no interpretation will be made here. After taking out the shaded part of the c-shaped defect, it is a regular hexagon, which is likened to a polygonal defect. Place the transverse wave oblique probe at the vertex of the hexagon, as shown in FIG. 13-1, which shows a schematic diagram illustrating the detection of a hexagon with surface waves of a transverse wave oblique probe.

The endpoint generates a refracted surface wave. According to Snell's law, the surface wave propagates on the surface on the two sides of the hexagon at a specified angle. When propagating to point A (E), superimposed reflected waves a are generated. Surface waves propagate to points E and A respectively through the end faces at the points A and E to generate superimposed reflected waves c (OEA and OAE). Surface waves continue to propagate to generate superimposed reflected waves b (OEAO and OAEO). Pull the transverse wave oblique probe back at the vertex of the hexagon, as shown in FIG. 13-2, which shows a schematic diagram illustrating the flaw detection of a hexagon with surface waves of a transverse wave oblique probe.

The endpoint generates a refracted surface wave. According to Snell's law, the surface wave propagates on the surface on both sides of the hexagon at a specified angle. When it propagates to point A (E), it continues to propagate at the original refraction angle, and when it reaches point B (D), it continues to refract and propagate. When the surface wave propagates to point C, a reflected wave OC appears, which is also a superposition of the surface waves propagating on both sides (OEDC and OABC) and a superposition of the surface waves each propagating a full circle on both sides (OEDCBAO and OABCDEO). Because it is an equilateral shape, the propagation distances of the surface waves on both sides are the same, and the OC wave is a superposition of the four reflected waves.

Turn the probe 90° to be perpendicular to the regular hexagon, as shown in FIG. 13-3, where there is shown a schematic diagram illustrating the flaw detection of a hexagon with surface waves of a transverse wave oblique probe rotated 90°. Because it is equilateral, the reflected waves OA and OE in the screen are superimposed. OAB and OED, OABC and OEDC, OABCDEO and OEDDBAO, OABCD and OEDCD, and OABCDE and OEDCBA, respectively, represent reflected waves of the surface waves traveling from the left and right directions, as well as echoes that propagate a full circumference, where reflected waves are all superimposed. The distance of each reflected wave on the screen represents the side length and circumference of the hexagon. Knowing these surface wave data, you know the shape of the hexagon. Transverse wave reflection is not considered at this time. After taking out the shaded part of the d-shaped defect, it is a circular shape, which is regarded as a cylindrical defect, the probe is placed on the vertex (endpoint) of the cylindrical shape to generate a surface wave, (The transverse wave is not considered), as shown in FIG. 14-1, which shows a schematic diagram illustrating the flaw detection of a cylinder with surface waves of a transverse wave oblique probe.

The surface wave propagates along the two sides of the cylindrical surface probe to point A by the refraction angle, generating superimposed OA reflected waves. After reflection, it continues to propagate back to the point of incidence, producing echoes in two directions of OAO, namely OA reflected wave and OAO echo. The four waves are superimposed into reflected wave A. Turn the probe 90°, as shown in FIG. 14-2, which shows a schematic diagram illustrating the flaw detection of a cylinder with surface waves of a transverse wave oblique probe.

The surface waves travel a full circle at the front and rear of the endpoint between the probe and the circular coupling, respectively. Reflected wave OO is the superposition of two echoes for each revolution. The indicated distance of OO represents the perimeter of the circle trailed by the surface wave. The formula by which it is converted to the diameter is: the formula for calculating the diameter of the circle directly in contact with the probe which is called the formula for the diameter of the outer circle. It is expressed by formula (3):a÷3.14÷ 1.08÷ conβ×2=D, where D is the diameter of the circle. The formula is derived as follows. Given the circular defect diameter, what is the value displayed in the instrument, D×3.142×1.08×cos β=a, conβ refers to the adjustment of the instrument's depth indication, a is the indicated distance of OO. The full moon-shaped circular test block is processed as shown in FIG. 14-3, and FIG. 14-3 is an exploded view of the circular body.

Cut from point A to point B along a dashed line (points AB are the intersections of the circle and the diameter). After cutting, it forms the left outer arc AB and the right outer arc AB that are equal, and the left inner arc AB and the right inner arc AB that are equal. As shown in FIG. 14-4, it is called a half-moon test block, and as shown in FIG. 14-5, it is called a crescent-shaped test block. The probes are placed on the endpoints of the two test blocks. The pulse a in the two figures represents the distances traveled by the surface wave in the inner arc, and the distances are equal, and the pulse b in the two figures represents the distances traveled by the surface wave in the outer arc, and the distances are equal. The pulses c in the two figures represent the perimeter distance of the surface wave traveling in the inner and outer arcs, respectively, and the distances are equal. Experiments show that in the process of surface wave propagation, even if it encounters a small end corner, it will propagate. The experiment shows that the thickness of line may impart different energies to the contact surface between the probe and the endpoint generated in the front-rear direction. With a thin line, the difference between the front and rear is big, while with a thick line, there difference between the front and rear is small. Crescents are thinner than half-moons, and half-moons are thinner than full moons.

FIG. 14-4 is a schematic diagram illustrating flaw detection of a half-moon with surface waves of a transverse wave oblique probe, and FIG. 14-5 is a schematic diagram illustrating flaw detection of a crescent with surface waves of a transverse wave oblique probe.

It is experimentally verified that Snell's law is also applicable to surface waves having been subjected to wave mode conversion, provided that there are endpoints that generate surface waves, and surfaces that have surface wave propagated. The energy of a surface wave is related to the thickness of the endpoint surface line, the roughness of the surface, and the angle of the surface and the transverse wave. The distance of the reflected wave discussed above is the propagating distance of surface waves. If the instrument is not adjusted according to the surface wave, the adjustment according to transverse wave shall be divided by (3230÷2980=) 1.08. In addition, the indicated distance of the reflected wave is the round-trip distance of the acoustic wave, so it involves the perimeter of the polygon and the perimeter of the circle. Dividing it by two is the length of the round-trip. Dividing by π is the diameter of the circle, which is the average diameter of the multiple deformations. The specific calculation will later be illustrated in connection with the actual practice.

In the weld flaw detection, transverse waves are present, defect endpoints (the endpoints may be points or lines) are present, and defect surfaces are present. Will surface waves be generated at the defect endpoints and transmitted on the defect surfaces through transverse waves? Put the transverse wave oblique probe on the test piece shown in FIG. 15, which is a schematic diagram of heterogeneous hole flaw detection test block. This figure just removes the shaded part in the test piece of FIG. 10. It is found that the transverse wave generates surface waves through the endpoints of the defects a, b, c, and d. The surface waves propagate and reflect on the surfaces of the defects a, b, c, and the results are the same as in FIGS. 11 to 14, a, b, c, and the surface wave propagation and reflection are the same, only that there are the additional reflected and diffracted waves that the defect end-point transverse wave reflected waves and other end-point transverse waves can hit, and more information about the defect, because the defect is empty, so there is no reflected wave of the transverse wave propagating inside the shape.

As shown in FIG. 15-1 to FIG. 15-4, where FIG. 15-1 is a schematic diagram illustrating the flaw detection of a plane defect with endpoint surface waves, FIG. 15-2 is a schematic diagram illustrating the flaw detection of a triangular defect with endpoint surface waves, FIG. 15-3 is a schematic diagram illustrating the flaw detection of a polygonal defect with endpoint surface waves, and FIG. 15-4 is a schematic diagram illustrating the flaw detection of a circular defect with endpoint surface waves.

This kind of circle in the weld is called the inner circle, and the formula dictating the conversion to the circle diameter is called the inner circle diameter formula, which is expressed by formula (4), D=A÷3.14÷ 1.08÷cos β×2.4, where A is the value of the instrument indicating the distance of 2 minus the value indicated by 1, where the obtained value represents the surface wave perimeter of the circle, and is set to A, D is the diameter of the circle, cos indicates that the scanning line of the instrument is adjusted according to depth, β is the refraction angle of the probe, the origin of the formula, A=D×3.14÷ 2.4×1.08×cos β, is as follows. The difference between the diameter formulas of the inner and outer circles follows; the outer circle is the direct contact between the probe's incident point and the endpoint of the circle, which is like a line contact, while in the inner circle the transverse wave is in contact with the endpoint, where the point of contact is a range. That is, the transmitting and receiving are not in the same position, the surface wave did not complete a full circle of the inner circle, but 83% of the full circle, so the calculated inner circle is divided by 2.4 and the outer circle is divided by 2.0.

Take the regular quadrilateral as an example to check the reflected waves that appear during flaw detection, as shown in FIG. 15-5, which shows a schematic diagram illustrating the flaw detection of the square shape with the endpoint surface waves.

First, when the four corners of the square defect are not R corners, pulse 1 is a transverse wave reflected wave at point A, and a surface wave is generated at the endpoint A. The surface wave propagates along the ABCD plane and the ADCB plane. Pulse 2 is superposition of the reflected waves of the surface wave at points B and D. Pulse 3 is the superposition of reflected waves of the surface waves at point C. Pulse 4 is the superposition of reflected waves of the surface waves at ABCD and ADCB planes at points D and B respectively. Pulse 5 is the superposition of the reflected waves of the surfaces waves in two directions which each travels around the square defect for a full circle. Pulse 6 is the Qt wave generated at the D point by the surface wave on the AD plane, and is defined as Qd. Pulse 7 is the Qt wave generated at the C point by the surface wave of the BC plane, and is defined as Qc. During this period, depending on the size of the defect, there may be reflected waves of the transverse waves or diffracted waves at points B and D, regarding Ql reflected waves that will be generated at points C and D, let's not talk about it for now.

Second, when the corner A of the square defect is R and the other corners are not, the reflected wave does not change.

Third, when only the B corner or the D corner is the R corner, the position and number of the reflection pulses remain unchanged, except that the pulses 2 and 4 have no superposition of the B corner or D corner reflections.

Fourth, when only the C corner is the R corner, the reflected wave of pulse 3 is gone, and other reflected waves still appear in their original positions.

Fifth, the corners B and D are R corners, the reflected waves 2 and 4 are gone, and the reflecting positions of other reflected waves are unchanged.

Sixth, if the four corners are all R-corner reflections, it is similar to a circular defect, and the reflected waves are only 1, 5, 6, and 7. The difference from the circular defect is that the circular defect does not have a Ql wave, and there will be an additional Qt wave between 6,7. If it is not a square but an unequal quadrilateral, only the overlapping waves are simply reflected separately.

Due to the different vibration modes of the longitudinal wave, the transverse wave and the surface wave, with the longitudinal wave, the vibration and the propagation directions are the same, and with the transverse wave, the vibration direction and the propagation direction are perpendicular to each other. Surface waves are a combination of longitudinal and transverse vibrations. They propagate in an elliptical trajectory on the surface, where the major axis of the ellipse is perpendicular to the wave propagation direction. The minor axis of the ellipse is parallel to the wave propagation direction. The vibration of the longitudinal wave at the endpoint generates tensile and compressive stress, or a small amount of alternating stress according to the shape and angle of the endpoint, which is not enough to generate a surface wave that can be received. The vibration of the transverse wave at the endpoints generates shear stress. Under the action of shear stress, the defect endpoint enables a part of the transverse wave to be converted to alternating stress to create a surface wave. The magnitude of the alternating stress is related to factors such as whether surface waves can be generated at the endpoints and the orientation of the defect.

The above experiments tell us that the endpoints of the defect can generate surface waves under the action of transverse waves, and surface waves can propagate along the surface of the defect. When encountering the corner, there is reflection, and the size of the defect surface can be calculated based on the position of the reflected wave. The surface waves will continue to propagate after reflecting at the corners, and generate circumferential echoes around the polyhedron after revolving about the polyhedron for a full circle. These combined are the shape of the defect and can be verified against each other.

This method of making a transverse wave generate a surface wave at a defect endpoint is called the defect endpoint surface wave method. When the flaw is found in the flaw inspection, it is most important to obtain the size and shape of the defect. At this time, the surface wave must be found, because the surface wave can measure the size and shape of the defect surface. Transverse wave flaw detection of the defect endpoint can produce deformed surface waves. After the endpoint reflected wave is determined, is there any surface wave in the echoes on the defect surface in the reflected waves of the defect?

If so, how do we determine which wave or waves are surface echoes? Let waves of different sound speeds appear on the screen in different colors, so that the flaw detector can learn them at a glance. The function of ultrasonic waves tells us that since surface waves can measure the size of the defect surface and the shape of the defect, there must be a way to prove that there is a surface wave in the reflected waves. The deformed surface wave is generated when the transverse wave hits the endpoint. After the surface wave is reflected back, it is converted into a transverse wave by the endpoint and received by the probe. When a surface wave encounters an endpoint during its propagation, it will inevitably be converted into a transverse wave. The deformed transverse wave then propagates to the bottom surface and reflects, and then returns along the original path to be received by the probe. The presence of this transverse wave generated by the surface wave can tells the flaw detector that there is an echo of the defect surface wave among the many reflected waves. This wave is the TRT wave, as shown in FIG. 16, which is a schematic diagram illustrating the generation of TRT wave.

The TRT wave is the endpoint reflected wave a generated by the transverse wave T1 at the defect endpoint A, and at the same time, the endpoint deformed surface wave R is generated. When the surface wave R propagates along the defect surface to the defect end corner B, a reflected echo b is generated, and at the same time, it is decomposed to generate the deformed transverse wave T2 (at this time, a diffracted wave c sometimes appears at the end corner B). T2 propagates to the bottom to generate the echo d, which is collectively called TRT wave, or Qt wave (wave named by Q of Qushifa), where t represents transverse wave. It can be seen that Qt wave is derived from surface wave. The presence of Qt waves proves the presence of surface waves in the defect's reflected waves. When the plane defect is vertical, the surface wave produces a deformed transverse wave at the end corner B and also produces a deformed longitudinal wave, collectively referred to as the TRL wave, or Ql wave, where l represents the longitudinal wave. At this time, the transmit transverse wave hitting point B may also produce a deformed longitudinal wave. The two longitudinal waves are almost coincident. The Ql wave is also derived from the surface wave. The appearance of the Ql wave proves that the defect surface is vertical or approximately vertical. At this time, the energy of the Qt wave is reduced.

The position where the Qt wave appears is calculated according to formula (5), $a+(\delta-a) \times \cos \beta$.

The position where the Ql wave appears is calculated according to formula (6), $a+(\delta-a) \div 1.8 \times \cos \beta$, where: $\delta$ value represents the thickness of the plate, if it is a secondary-wave then $\delta$ is doubled namely $\delta \times 2$; a represents the depth indicating value of the endpoint of the surface wave generated by the defect; $\beta$ represents the refraction angle of the probe; 1.826 is the ratio of the sound velocities of the longitudinal and transverse and waves (5900/3230); $\cos \beta$ indicates that the scanning line of the instrument is adjusted according to the depth display (converting the acoustic wave path of the deformed wave to a depth value). This formula does not consider the height of the defect itself because Qt wave is generated from point B. If we consider the height b of the defect itself, the formula is $a+(\delta-a-b) \times \cos \beta$ so that Qt value will be more accurate. If we know the defect's own height, the flaw detection is over, and calculating the Qt value would be meaningless. If calculated according to formula (5), the actual positions where Qt waves are displayed are all greater than the calculated positions. The difference is related to the size of the defect surface and the slope of the defect, but these differences are not large. For example, let the defect surface be 4 mm, and let the slope go from the smallest to the largest, then using a 45° probe to detect flaws, the difference between the Qt wave actually displayed and the calculated Qt value is at most about 1 mm. Using a 70° probe for flaw detection, the maximum difference is 2.5 mm. Therefore, when calculating according to formula (5), the defect size can be completely ignored. If the lower endpoint of the defect is found through the diffraction of the lower endpoint, the size of the defect surface is calculated, but it is inaccurate because some surface defects have a slope, and error is accompanied by the movement of the probe, and with some defects the lower end of the defect cannot be found at all.

When a defect is found during flaw detection, sometimes what appears as a single defect wave may be the reflected waves of multiple paths converging together. To confirm the reflected wave, a motion called a probe push-pull-twist is used. Push means to slowly push the probe forward, pull means to slowly pull the probe backward, twist means to twist the probe left and right. Under these actions, the probe all performs a linear, rather than zigzag movement. Through the push and pull and twist of the probe, it is observed which waves are rising or falling at the same time, which wave's wave-front line and wave-rear line are rising and falling at the same time, and which wave's wave-front line and wave-rear line are such that the wave-front rises and the wave-rear line falls or otherwise the wave-front line falls and the wave-rear line rises, which wave's peak rises and falls at the same time, or a rising peak appears at the same time as it falls, or to opposite namely a falling peak appears at the same time when rising. We can observe the wave peak, wave-front line, and wave-rear line at the same time, but sometimes when the sensitivity is low, the wave lines are not as obvious as when it is high, and the wave peak is not visible when it is very high. This observation can distinguish the echoes of different paths that overlap, or the several reflection points of the defect itself that are overlapped. After the distinguishing, the data of the defect's shape is obtained, namely the data of the defect's three-dimensional shape is obtained.

The reflected pulses generated by different sound velocities and different paths on the screen are processed by software and displayed in different colors. For example, a normal transverse wave is set to one color, a longitudinal wave to one color, a surface wave to one color, a transverse to longitudinal transition is set to one color, a longitudinal to transverse transition is set to one color. Similarly, a transverse to surface transition, a surface to longitudinal transition, a surface to transverse transition all have their respective colors, and combinations of these colors. Which enables the observation to be more intuitive.

Through the push-pull-twist of the probe, the defect's end-point reflected wave is found. As long as the reflected wave is not a vertical reflection from the defect surface, the end-point reflected wave can be found. The end-point reflected wave is not necessarily the highest reflected wave, but it must be the front most reflected wave. Through calculation and observation, check if there is the Qt wave. If there is, it is proved that the defect has surface waves.

For example: let the thickness of the test plate be 40 mm, the refraction angle of the probe be 45°, the indicated depth of the defect's reflected wave be 15 mm. At this time, the position where the Qt wave appears is calculated according to formula (5), 15+(40-15)×cos 45°=32.6. See if there are reflected waves near the scanning line 32.6 of the instrument. If there are, it is proved that there is generated a surface wave by the defect. (This wave is also within the thickness of the plate. If it is judged as a defect wave by the reflection method, the result is an error. For some defect this wave is higher than the defect reflected wave). For another example, let the thickness of the plate be 15 mm, the probe refraction angles be 45°, 60°, 70° respectively, and the indicated depth of the defect reflected wave be 10 mm. Then according to formula (5), the Qt value of each angle is calculated, where the 45° Qt value is At 13.5 mm, the 60° Qt value is at 12.5 mm, and the 70° Qt value is at 11.7 mm. It is not difficult to see that the reflected wave and Qt wave are close or connected together. If the surface wave reappears at this time, the entire peak shape looks like the reflected wave of an irregular defect, and in the past it will be determined as a sawtooth reflection of a crack. The defect reflection waveform is a combination of the reflected, diffracted, and deformed waveforms of the defect. Sometimes it is only a single reflected wave, sometimes it is a reflected wave and a diffracted wave, sometimes it is a reflected wave and a deformed wave, and sometimes it is all the reflected, diffracted, and deformed waves. The defect's reflection waveform also depends on the width of the defect, not the length of the defect. As shown in FIG. 17-1 and FIG. 17-2, FIG. 17-1 is a schematic diagram illustrating the flaw detection of a parallel transverse through-hole having a thread of a probe, and FIG. 17-2 is a diagram illustrating the flaw detection of a vertical transverse through-hole having a thread of a probe. If in ultrasonic flaw detection the characterization is carried out based on the reflected waveform, it is imperfect theory that would produce imperfect conclusions.

As shown in FIG. 17-1 and FIG. 17-2, regarding the probe sound beam diffusion for the defect that is parallel to flaw detection surface, even if the defect surface is irregular in the length direction, it is difficult to reflect the reflected wave, because the difference in the diffused sound paths in the horizontal direction is very small. The reflected wave of the transverse through hole of the M4 screw is almost the same as the reflected wave of the Φ4 mm transverse through hole. For the sound paths hitting the same defect, there would be no distinction if there is no difference. For flaw detection in the vertical direction, even the number of screw threads of the M4 screw can be distinguished, because the difference in the vertical distances of the diffused sound paths in the vertical direction is relatively large, and there is distinction when there is difference.

Regarding the number of Qt waves, one vertical surface of the defect generates one Qt wave. So the number of Qt waves indicates that there are the same number of defect surfaces that generate surface waves. If the defect surface is vertical or approximately vertical, in addition to generating Qt waves, Ql waves are also generated at the same time. If it is a circular defect, there are three Qt waves appearing on the two sides and bottom of the circle. The distance of the three waves is related to the diameter of the circle. The circular defect also produces a deformed longitudinal wave perpendicular to the flaw detection surface. This longitudinal wave is a reflected wave hitting the upper surface. Its appearance proves that the defect is round, as shown in FIG. 18, which is a schematic diagram of the number of circular defect Qt waves. To prove whether it is a longitudinal wave, in addition to calculation, you can use your finger to couple to the longitudinal wave position, and the longitudinal wave should be beating with your finger at the same time. If it is a deformed longitudinal wave generated by an arc, other reflected waves are different.

The presence of Qt waves proves that there are defect surfaces that produce surface waves and surface wave reflections. How to determine which wave is a surface wave? Because Qt wave and surface wave are both related to the endpoint reflected transverse wave, through the push, pull and twist action of the probe, if there is also a wave in the defect waves that changes synchronously when the endpoint reflected wave and the Qt wave are changing synchronously, then this wave is the surface wave. If multiple waves change synchronously, then there are surface waves on multiple surfaces, and there are at least as many surface waves as there are Qt waves, and there are at least as many surfaces that have surface waves.

The position of the Qt wave sometimes shows a reflected wave generated when the defect lower end-point diffracted wave propagates to the bottom surface. The method of differentiation is as follows. The push, pull, and twist of probe can show that the wave is not synchronized with the endpoint reflected wave and the surface wave, and is synchronized with the diffracted wave at the defect's lower endpoint. Sometimes the Qt wave looks like a wave, but when distinguishing a surface wave from a diffracted wave, the wave-front line may change synchronously with the endpoint reflected wave and the surface wave, while the wave-rear line may change synchronously with the diffracted reflected wave. This is the change that the Qt wave and the diffracted reflected wave are almost close together, and the identification of the wave-front line and the wave-rear line is shown in FIG. 19. FIG. 19 is a diagram illustrating the distinguishing between a wave-front line, a wave-rear line, and a peak.

Sometimes there are Qt waves, but no surface waves are seen, and only one end-point reflected wave appears. At this time, the flaw detection sensitivity can be increased. If still no surface wave has appeared, by pushing or pulling or twisting the probe, if the wave-front line, wave-rear line of the endpoint reflected wave and Qt wave rise and fall simultaneously, it means that the defect surface is very small and the two waves are together. If only the wave-rear line and the Qt wave rise and fall at the same time, it means that this wave is a reflected wave of the diffracted wave generated at the other end of the defect. At this time, there is no surface wave generated by the defect. This "Qt" wave is the reflection of the incident transverse wave on the bottom surface through the lower endpoint of the defect. As shown in FIG. 20, FIG. 20 is a schematic diagram of a false "Qt" wave.

The presence of Q waves is conditional on the defect. As shown in FIG. 21, division is performed with the upper endpoints of the defect respectively pointing to the coordinate origin. For primary-wave flaw detection, in the third quadrant, there are vertical and horizontal defects that generate surface waves, while in the fourth quadrant the defect generates no surface waves. For secondary-wave flaw detection, in the fourth quadrant, there are vertical and horizontal defects that generate surface waves, while in the third quadrant the defect generates no surface waves. It can be seen from FIG. 21 that the position of the defect and the position of the probe determine the presence or absence of surface waves. If no surface wave is found with the primary-wave, the secondary-wave can be used. If it is not present on one side, it can be checked on the other side. In addition, not all surface waves would lead to the generation of Qt waves. The magnitude of the inclination of the defect also determines the presence or absence of Qt waves. Even if the defect produces a surface wave, the greater the inclination of the defect, the lower the Qt wave to the degree of being absent. A horizontal plane defect may lead to the production of surface waves, but no Qt waves would appear. Generally, Qt waves would become lower and lower when the inclination of the defect is greater than 45°.

How to determine the existence of surface waves in the absence of Qt waves? When the endpoint reflected wave is determined, and there are waves appearing thereafter, then by pushing and pulling and twisting the probe, if there is a wave that synchronously rises and falls subsequent to the rise and fall change of the endpoint reflected wave, and by the horizontal and depth positions of the reflected waves at both ends of the defect it is determined that the inclination of the defect surface that generates the surface is greater than 45° and less than or equal to 90°, then the wave that synchronously changes is the surface wave.

When after the endpoint reflected wave rises there is a wave that synchronously falls, and after the endpoint reflected wave falls there is a wave that synchronously rises, then this wave is the diffracted wave of the other end of the defect. Sometimes when the probe is pushed or pulled or twisted, the reflected wave doesn't undergo a rise or fall change, but the front and rear end lines of the reflected wave change up and down. This phenomenon is the reflection of two parts, one is the diffracted wave of the other end of the defect, and the other is the reflection of the surface wave. The reflected waves are connected together. The front line represents the reflection of the diffracted wave and the rear line represents the reflection of the surface wave.

Any defect has an endpoint. The surface wave energy generated at the endpoint is related to the stress generated by the ultrasonic transverse wave at that point, and it is related to the angle between the end corner and the transverse wave. In ultrasonic flaw detection, the endpoint that can produce the surface wave with the maximum energy should be found.

Ultrasonic flaw detection is based on the defect's reflected echo to determine the existence of the defect. When the sound beam is perpendicular to the defect surface, there is only one reflected wave. If when flaw detection is performed on this surface the defect is perpendicular to the sound beam, and when the surface is replaced with another one it is still perpendicular, then there would be reflection at the intersection of two defect surfaces namely the endpoint of the defect. For any defect surface that is not perpendicular to the sound beam, there are reflection and diffraction at the upper and lower endpoints of the defect, as well as the reflection of the defect surface. The heights of these reflected waves depend on the angle between the sound beam and the defect surfaces. Whether these waves can be distinguished depends on the size of the defect, the resolution of the instrument, and the slope of the defect.

As shown in FIG. 16, when the transverse wave propagates to the defect's endpoint, in addition to generating reflected and diffracted waves, more importantly surface waves are generated, which are called endpoint surface waves. As R shown in FIG. 16, the endpoint surface wave propagates along the defect surface, and then encounters an end corner where a surface wave is generated. Meanwhile, a deformed transverse wave or a deformed longitudinal wave is generated and transmitted through the workpiece. Then when it encounters a surface, it is reflected. When it encounters a polyhedron, the surface wave will continue to propagate, and each reflection can determine the size of the defect surface. If it is a single-sided defect, the surface wave would be directly reflected when it propagates to the end corner. If it is a polyhedron-like defect, the surface wave propagates and reflects on each surface, then propagates and then reflects back to the original point, which reflects the size of each surface and the size of the volume-shaped perimeter. If it is a cylindrical or spherical defect, the surface wave would orbit for a full circle and then return to the original point, and the propagation path is equivalent to the circumference of the circle.

Regarding the surface waves mentioned above, can all the defect's endpoints produce surface waves? Is there always reflection when a surface waves propagates to the end corners? Can it return to the origin after propagation? Can the end corner of the defect generate deformed transverse wave and longitudinal wave that are converted from surface waves the same time when surface wave reflection occurs? The same applies to reflected, diffracted, and deformed waves generated by incident transverse waves at the upper endpoint, lower endpoint of the defect, and defect surface. These are related to the inclination of the defect, the included angle of the defect surface, and the intensity during the propagation of the ultrasonic wave. If the transverse wave flaw detection can determine the endpoint of the defect, the surface size generated by the endpoint can be used to determine the size and shape of the defect, which is simpler, faster, more realistic and more comprehensive than the judgement based on reflected and diffracted waves.

The surface wave can reflect the shape and size of the defect, but it cannot fully reflect the inclination of the defect. When the ultrasonic wave encounters a defect during its propagation, the defect surface can generate reflected, refracted and deformed waves. Both the upper and lower endpoints have the functions of generating reflected, diffracted and deformed waves. The process of ultrasonic wave propagation generates kinetic energy. Different propagation methods generate different kinetic energy. When kinetic energy is converted into force, there are tensile and compressive stress, shear stress and alternating stress. The defect has an orientation and the probe has an angle. When the sound beam and the defect surface are perpendicular to each other, there is only one force. As long as it is not perpendicular, the lower endpoint of the defect can decompose the force and change the vibration mode, thereby deriving one wave from another wave (wave mode conversion) and changing the direction of propagation. The magnitude of this function of the endpoint is related to the angle of the defect and the angle of the sound beam. Snell's law and formula are applicable to the reflection, refraction and wave mode conversion of the defect surface during the ultrasonic flaw detection process.

According to Snell's law, the conversion angle between the longitudinal wave and the transverse wave is bound by a range. When the reflection angle between the transverse wave and the defect surface is less than 33°, in addition to the transverse wave reflection, a deformed longitudinal wave reflection less than 90° can also be generated. When reflected longitudinal wave and the reflected transverse wave hit the bottom surface, it further produces reflected longitudinal wave and reflected transverse wave. If Snell's law is met, the reflected wave will generate a deformed transverse wave and a deformed longitudinal wave, as shown in FIG. 22. Conversely, when the incident angle of the longitudinal wave is less than 90°, in addition to longitudinal wave reflection, a deformed transverse wave reflection less than 33° can also be generated. The reflection, diffraction, and deformation of the lower endpoint of the defect is somewhat different from those of the defect surface. For the time being, they are both considered in accordance with Snell's law, collectively referred to as the lower end of the defect (including the defect surface and the lower endpoint).

The type, shape, location, and angle of defects in the weld are unknown. And some defects may occur at any position in the weld, and they are all-round. When a sound wave encounters a defect, it is bound to generate a reflected wave, a diffracted wave, and a deformed wave. This is why in the flaw detection of welds, with the appearance of a defect, so many reflected waves will suddenly fall on the screen (in addition to the weld corner reflected wave and the deformed wave generated by the weld corner). And we only determine the wave in front of the corner reflected wave (bottom wave) as the defect wave, and the subsequent waves are not considered and analyzed. Because the wave appearing in front of the bottom wave is a direct reflected wave of the defect, it is sufficient to accurately analyze the defect. The waves that appear behind the bottom wave are very variable. Most of the waves cannot be explained by the reflection method. The waves in front of the bottom wave can easily be used to quantify, characterize and locate the defect. The waves that appear after the bottom wave have no actual value. This flaw detection method has been inherited from the beginning to the present. So is it accurate when the waves in front the bottom wave are defined as the direct reflected waves of the defect? Practice tells us that the reflected waves in front of the bottom wave are not necessarily all direct reflected waves of the defect. It is also subject to misjudgments to analyze the defects waves in front of the bottom wave by the reflection method. As mentioned earlier, sometimes the positioning of the defect is accurate, but the defect is elsewhere. Sometimes a defect is positioned but in actuality there is no defect, while sometimes no defect is positioned but in actuality there is a defect. In fact, in ultrasonic flaw detection, whether in front of or in rear of the bottom wave, each reflected pulse appearing on the screen is a display of different shapes and parts of the defect by the ultrasonic wave through different functions. This display tells the flaw detector various information about the defect.

How to understand all the reflected pulses on the screen? First, check the kinds of waves that can be generated by the transverse wave oblique probe. As shown in FIG. 23, FIG. 23 is a schematic diagram of the waves generated by the transverse wave oblique probe.

Why are there a longitudinal wave and a surface wave in the transverse wave oblique probe? The reason is very simple. As long as there is vibration, there will generate the force and direction of propagation, and pull and compression of longitudinal waves, shear of transverse waves, and alternating stress of surface waves. There would also be longitudinal wave whose direction of vibration is the same as the direction of propagation, and transverse wave whose direction vibration is perpendicular to the direction of propagation, and surface wave of which the combination of the longitudinal vibration and transverse vibration propagates on the surface along an elliptical path. Functions of various probes are mainly based on the functions suggested by their names, but other functions that are also present in the probe cannot be ignored. These functions may influence the flaw detection, such that the wave that may occur during the flaw detection process cannot be clearly interpreted.

The transverse wave oblique probe mainly generates transverse wave and also generates surface and longitudinal waves, as shown in FIG. 23. Transverse wave oblique probes are made based on the third critical angle of Snell's law. Theoretically, pure transverse waves are generated, but surface waves are also generated the same time refracted transverse waves are generated. As the angle of refraction increases, the energy of the surface wave also increases. The surface wave is attenuated during the movement of the probe, and the surface wave is easily absorbed by the coupling agent during the flaw detection, but it exists objectively. If there is a defect on the surface in front of the probe, as the coupling agent in front of the probe decreases, the defect detected by the surface wave will have a display of a reflected pulse.

In addition, the edges of the wafer of the probe generate diffracted waves as the defect through the transmitted and received vibrations. The diffracted waves generated at the upper and lower ends of the wafer are also refracted in a certain angular range when they are transmitted to the surface of the workpiece through plexiglass. It then propagates in the form of longitudinal waves in the workpiece with a relatively low energy. If there is a defect reflected echo forming a loop with the longitudinal wave, a reflected echo will appear on the screen.

Further, when the ultrasonic transverse wave is propagated, it can generate reflected waves, diffracted waves, and deformed waves after encountering a heterogeneous interface (defect). Which lead to the emergence of the later Huygens principle, the reflection characteristics of waves, the diffraction characteristics of waves, and the conversion characteristics of waves.

Wave's conversion characteristics: when the ultrasonic transverse wave propagates to the interface (defect surface) of two different media or the interface of the profiled surface of a medium and the endpoint of the defect, not only will the reflected wave and diffraction wave with the same wave mode be generated, but also a reflected wave or surface wave with a converted wave mode be generated. This characteristic is the theoretical basis for using the wave's conversion function for detection, as shown in FIG. 24-1 to FIG. 24-3, where FIG. 24-1 is a schematic diagram of wave mode conversion, FIG. 24-2 is a schematic diagram of wave mode conversion, and FIG. 24-3 is a schematic diagram of wave mode conversion.

In ultrasonic flaw detection with a transverse wave oblique probe, reflected waves, diffracted waves and deformed waves from the defect will appear on the screen. The method of comprehensive analysis and judgment of these waves is called the reflection-diffraction-deformation flaw detection method.

In the reflection-diffraction-deformation flaw detection method, the reflected wave having the reflection characteristic and the diffracted wave having the diffraction characteristic tell us the presence or absence of a defect. The endpoint deformed surface wave having the deformation characteristics tells us the shape and size of the defect. The combination of the deformed transverse wave, the deformed longitudinal wave, and the transverse wave and as well as their paths tell us how the waves came into being, tell us the angle or direction of the defect, and collectively tell us what the defect looks like and where it is. After the defect is found by the transverse wave, these reflected waves, diffracted waves and deformed waves from the defect, together with the reflected waves of the weld fillet, are drawn or compiled into software through the following ten sets of various wave reflection loops, whereby it can clarify the generation of each reflected echo appearing in the weld flaw inspection screen.

The first group is shown in FIG. 25-1. FIG. 25-1 is a schematic diagram of the loop of the reflected, diffracted, and deformed waves of the defect in primary-wave flaw detection.

The second group is shown in FIG. 25-2. FIG. 25-2 is a schematic diagram of the loop of the reflected, diffracted, and deformed waves of the defect in primary-wave flaw detection.

The third group is shown in FIG. 25-3 and FIG. 25-4. FIG. 25-3 is a schematic diagram of the loop of the reflected, diffracted, and deformed waves of the defect in primary-wave flaw detection. FIG. 25-4 is a schematic diagram of the loop of the reflected, diffracted, and deformed waves of the defect in primary-wave flaw detection.

The fourth group is shown in FIG. 25-5. FIG. 25-5 is a schematic diagram of the loop of the reflected waves of the defect in primary-wave flaw detection.

The fifth group is shown in FIG. 25-6 and FIG. 25-7. FIG. 25-6 is a schematic diagram of the loop of the reflected, diffracted, and deformed waves of the defect in secondary-wave flaw detection. FIG. 25-7 is a schematic diagram of the loop of the reflected, diffracted, and deformed waves of the defect in secondary-wave flaw detection.

The sixth group is shown in FIG. 25-8. FIG. 25-8 is a schematic diagram of the reflected echo when the defect reflected wave encounters the weld with an enhanced height.

The seventh group is shown in FIG. 25-9. FIG. 25-9 is a schematic diagram of the reflected, diffracted, and deformed waves of the weld corner.

The eighth group is shown in FIG. 25-10. FIG. 25-10 is a schematic diagram of the loop of the reflected wave in primary-wave flaw detection of a heterogeneous plate with a heterogeneous fillet weld.

The ninth group is shown in FIG. 25-11. FIG. 25-11 is a schematic diagram of the loop of the reflected wave in secondary-wave flaw detection of a heterogeneous plate with a heterogeneous fillet weld.

The tenth group is shown in FIG. 25-12. FIG. 25-12 is a schematic diagram of the loop of the secondary-wave perpendicularly reflected by the defect in the weld.

Pulse 1 is the primary vertical reflected wave of the defect surface, pulse 2 is the secondary vertical reflected wave of the defect surface, and the distance is different from the primary reflected wave by an additional propagation b of the sound wave within the probe. The distance b can be determined by the reflected wave during the test of the incident point of the probe of the IIW test block. And the distance between the secondary-wave and the subsequent reflected wave is the distance that the sound wave travels in the probe.

As shown in FIG. 25-13, if the scanning line is adjusted according to the sound path, the interval b between the two waves represents the sound path. If adjusted by depth, the distance b between two waves represents depth. How to determine the size of such defects? 1. Flaw detection on the other side, 2. Flaw detection by secondary-wave, 3. Flaw detection by changing the angle. If it is not vertical, it can be determined by calculating the reflected, diffracted, and deformed waves at the upper and lower endpoints of the defect.

Through the analysis of the above ten sets of reflected echo paths, it is found that the highest reflected wave of the defect is sometimes not a direct reflected wave of the defect, but a deformed wave. Sometimes the foremost reflected wave of the defect is not a direct reflected wave of the defect, but also a deformed wave. Sometimes the defect doesn't have a normal reflected wave, but has a deformed wave reflection. Sometimes in the flaw detection range, there are multiple similar defect reflected waves appearing at the same time, but this is not the reflected waves of multiple defects, but the reflected waves of a single defect and the reflected and deformed waves having different paths of this defect. Sometimes there is only one defect reflected wave, with a wide wave width, and several wave peaks are connected together. These peaks represent the defect's reflected waves, diffracted waves, and deformed waves, etc., each of the peaks has a different propagation path of its own. In addition, the heterogeneity of the flaw detection site causes a deformed wave to be displayed in the weld. The emergence of these problems leads to inaccurate conclusions of the flaw detection, but the flaw detection personnel do not know yet, because all flaw detection is based on the reflection method to analyze and assess the defect.

Using the reflection-diffraction-deformation flaw detection method, combined with the ten sets of defect wave return pats, and by plotting (without software), all the reflected pulses appearing on the screen, totaling 77+2Q echoes, are analyzed to determine how all reflected pulses are generated. Although the 77+2Q echoes don't actually appear at the same time, all the reflected pulses appearing would not fall out of the principle of generation of the 77+2Q echoes. The formation of the 77+2Q echoes is related to the formation of the weld and the shape and location of the defect. The 77+2Q echoes don't include multiple reflections at one location. The following is a case of application of 77+2Q echo analysis.

Example 1: 40 mm thick plate with a butt weld, there is a 4 mm wide plane defect at 15 mm measuring from the upper surface towards the center, the defect is inclined by 20°, the 45° transverse wave oblique probe is used for flaw detection, a primary-wave inspection found a defect wave at 15 mm, the wave covers the defect's upper endpoint reflected wave a and lower endpoint diffracted wave b, surface wave r, Qt wave, etc., and by pushing, pulling and twisting the probe, it is found that there is a defect reflected wave at the depth of 24 mm, as illustrated in FIG. 26-1.

Push and pull and twist probe. According to FIG. 25-4, one of the 77+2Q echoes, transverse wave—transverse wave—longitudinal wave, is drawn and measured. As shown in FIG. 26-2, (21+25+42/1.826)÷2×cos 45°=24, it is found that the reflected wave at 24 mm is the incident transverse wave hitting the defect, and the defect surface has an inclination. The reflected transverse wave generated by the defect surface is reflected to the bottom and then transformed into a deformed longitudinal wave reflection which is received by the probe. According to Snell's rate, the inclination of the defect can be calculated. For example, a 45° probe, the sound beam hits a defect surface inclined at 20°, and the defect forms an angle of (45°−20°=)25° with the sound beam, resulting in the reflected transverse wave whose sound beam forms an angle of (90°−25°=)65° with the normal line of the defect surface. The transverse wave propagates to the bottom surface, and a transverse wave at an angle of 10° from the normal line of the bottom is generated. According to Snell's law, sin 10°/3230=sin βt/5900, βt=18°, the transverse wave generates a reflected transverse wave of 10°, which is not received by the probe. The 18° deformed longitudinal wave generated enters the probe's incident point, so as to calculate the inclination of the defect drawing (afterwards, it will be done by software). If the reflection method is used to calculate the reflected wave at 24 mm, the conclusion will be wrong.

Example 2: A test block is 40 mm thick, a Φ3 mm transverse through hole is 10 mm from the surface, and a 45° transverse wave oblique probe is selected. The instrument's depth indication is adjusted. The reflected wave that appears during the second wave inspection is shown in FIG. 26-3. The first is the secondary-wave transverse through-hole reflected pulse B, which indicates that the depth of the transverse through-hole is 70 mm. The second is the reflected pulse R of the surface wave of the transverse through-hole, indicating at 73 mm, (73−70=3, the 45° probe flaw detection difference is the diameter of the transverse through-hole), the diameter of the transverse through-hole is 3 mm. The fourth is the Qt wave. The indicated depth is 70+10×cos 45°=77 mm, the third reflection pulse, the depth indication is 75 mm, is one of the 77+2Q echoes, and it is 2-TT1T5T6T7 in FIG. 26-3., total transverse wave reflection, calculated as follows, (OA+AB+BC+CD+DO)÷2×cos 45°=(56+43+10+54+50)÷2×0.707=75 mm. Any reflected pulse in the weld can be explained clearly by using the plotting analysis with the reflection-diffraction-deformation flaw detection method.

Application of reflection-diffraction-deformation flaw detection method with the transverse wave oblique probe The requirements for the probe by reflection-diffraction-deformation flaw detection method are as follows: 1. Conventional probes, good probe will enable the flaw detection to be more accurate; 2. If only one angle is selected, the main angle is 45°. The requirements for sensitivity areas follow: 1. Use Φ0.5 mm horizontal through hole as the initial sensitivity; 2. Allow the minimum defect according to the design requirements as the initial sensitivity; 3. The sensitivity should be formulated in accordance with the grain size of the weld. The requirements for the side length of the defect are: 1. The reflection-diffraction-deformation flaw detection determines that there is no change in the length direction of the defect, and the side length of the 6 dB method is used; 2. If with the reflection-diffraction-deformation flaw detection of the two ends of the defect the length direction changes, the probe is tilted 15°-45° to use the endpoint reflection-diffraction-deformation method to determine the endpoints of the defect.

Examples of Reflection-Diffraction-Deformation Flaw Detection Method

First, planar flaw detection: planar flaws include crack, unfused, not welded through, where the flaw detection method for these kinds of plane defects in various states are as follows;

1.1 How to determine the size, shape and properties of the defect when the plane defect is parallel to the detection surface, as shown in FIG. 27-1. FIG. 27-1 is a schematic diagram of detection of horizontal plane flaw.

First, the scanning line of the instrument is adjusted according to the depth display, the probe refraction angle β, and pulse 1 is the reflected wave plus the diffracted wave a of the plane defect A. Pulse 2 is the reflected wave plus the diffracted wave b at point B of the plane defect. Pulse 3 is the reflected wave r generated at point B when the surface wave generated at the endpoint A of the plane defect propagates to the point B, and the reflected wave generated on surface AB is propagated in the opposite direction to the incident angle. If a formed weld is encountered, then the reflected echo as illustrated in FIG. 25-8 would occur. If the defect surface is not flat, then there will be a reflected wave appearing between the two waves a and b. So how to determine the width of the plane defect? Move the probe back and forth to find the highest reflected echo of each of the points A and B, and we will see that the corresponding depth values of the two highest pulses of the waves a and b are the same. The moving interval of the probe between the two highest points is the horizontal value, namely the width displayed value of the corresponding defect. The reflection-diffraction-deformation flaw detection method uses point A as the defect endpoint. The surface wave generated at the endpoint is pulse 3. When the probe moves back and forth, if pulse 1 and pulse 3 rise or fall at the same time, find the highest point, then the distance between the two waves of a and r is the display value of the sound path depth of the surface wave along the width of the defect. The velocity of the transverse wave is 1.08 times that of the surface wave. The instrument is adjusted by the transverse wave, so the depth value displayed by the instrument must be divided by 1.08. The depth display needs to be converted to the hypotenuse, that is, the actual size of the defect, it is calculated as follows, (ar value÷1.08)÷cos β. The result is the width of the defect.

Example: If the ar value indicated by the instrument is 3 mm and the refraction angle of the probe is 45°, (3÷1.08)÷cos 45°=4 mm. In flaw detection, if the defect waves are only wave 1, wave 2, wave 3, and the depth positions of wave 1 and wave 2 are the same, and the horizontal positions are different, it can be confirmed that the defect is horizontal and planar. The detection reflection results on both sides of this defect are similar. This kind of defect is only unfused between layers, but it is not common.

1.2 How to determine the size, shape and nature of the defect when the plane defect is perpendicular to the detection surface? The first is how many types of echoes can be generated when this defect is detected. From the first group to the fifth group, it can be seen that this defect will appear according to the reflected waves of more than twenty loops depending on the location. Taking an actual defect as an example, there is a test block of a thickness of 40 mm, and at a depth of 15 mm, there is a 4 mm high vertical defect. A 45° transverse wave oblique probe is used, as shown in FIG. 27-2.

First, the scanning line of the instrument is adjusted according to the probe refraction angle β depth display. During flaw detection, the endpoint reflected wave of the defect is determined and it is also determined regarding the presence or absence of Qt wave. Pulse 1 is the reflected wave at the endpoint A of the vertical plane defect. Pulse 2 is a diffracted wave at point B of a plane defect. Pulse 3 is the reflected wave r generated when the surface wave generated by endpoint A of the plane defect propagates to point B. Pulse 4 is a deformed longitudinal wave generated when the incident transverse wave hits the lower end of the defect surface. This longitudinal wave is reflected to the bottom surface C. After reflection on the bottom surface, it forms a transverse wave—longitudinal wave—longitudinal wave loop with the longitudinal wave emitted by the probe. As illustrated i FIG. 25-5, the calculation is as follows. First, the dimensions of each channel are measured by drawing, (21+26÷1.826+41÷1.826)÷2×cos 45°=20. This wave appears at a depth of 20 mm from the scan line. The presence or absence of this wave is related to the position and shape of the defect and the angle of refraction of the probe. Pulse 5 is a vertical echo generated when wave Ql and the deformed longitudinal wave generated at point B by the transverse wave hit point D on the bottom surface. The two waves are superimposed together, as shown in FIG. 25-1 and FIG. 25-2. This wave is only available when the defect surface is vertical or approximately vertical. It is also one of the waves that prove the shape of the defect. According to the figure above, it is calculated that the pulse appears at the scanning line 15+25÷1.826×cos 45°=25.

Pulse 6 is the transverse wave generated when the transverse wave hits the lower end of the defect surface, which is then reflected to the bottom surface and directly received by the probe, forming a transverse wave—transverse wave—transverse wave loop. As shown in FIG. 25-3, according to the above figure, it is calculated that the pulse appears at the position (21+25+41)×cos 45°=30.7 of the scanning line.

Pulse 7 is a reflected wave generated when the diffracted wave generated by the transverse wave hitting the point B of the defect propagates to point D of the bottom surface, as the a and the Qt wave generated at point B in FIG. 25. As shown in FIG. 25-2, the two waves superimposed together, which can be distinguished from each other by pushing pulling and twisting the probe. At this time, the wave-rear line represents the Qt wave. According to the figure above, it is calculated that this pulse appears at position 15+25×cos 45°=32.6 of the scanning line.

How to determine the height of a plane defect? The reflection-diffraction-deformation flaw detection method is as follows. When the probe moves back and forth, if pulse 1, pulse 3 and pulse 7 rise or fall at the same time, find the highest point of pulse 1 and pulse 3, then the distance between the two waves is the acoustic path of the surface wave along the width of the defect. The scan line of the instrument is set as a transverse wave, and the speed of the transverse wave is approximately 1.08 times the speed of the surface wave. The number of acoustic path displayed by the instrument needs to be divided by 1.08, and the depth display needs to be converted into a hypotenuse, that is, the actual size of the defect is calculated as follows, (ar value÷1.08)÷cos β, and the result is the height of the defect. Example: If the ar value indicated by the instrument is 3 mm and the refraction angle of the probe is 45°, (3÷1.08)÷cos 45°=4 mm, the result is the height of the defect.

In flaw detection, if wave 1, wave 2, wave 3, wave 5, wave 7 meet the above conditions, it can be confirmed that the defect is vertical plane, and the height of the defect can be calculated at the same time. Such defect has similar reflection results for flaw detection on both sides. Such defects include cracks, unfused and incomplete weld at the groove bevel.

Second, circular and semi-circular flaw detection. Circular flaws include spherical air holes, horizontal through holes (strip air holes) and flat bottom holes. The semi-circular defect is considered as a half of the circular defect. The flaw detection method is as follows.

2.1. Flaw defection of transverse through holes and spherical air holes, as shown in FIG. 28-1.

Example: Weld flaw inspection a plate with a thickness of 50 mm using a 45° probe, scanning line depth adjustment, it is found at depth 20 mm there is a point-shape defect wave A, a reflected wave at 22 mm is r, a reflected wave at 28 mm is L, a cluster of 3 reflected waves at 42 mm. First confirm the Qt wave of the defect wave, 20+30×cos 45°=41.2, this wave is the Qt wave of the defect. There is a surface that generates three Qt waves. Push pull and twist the probe, the reflected waves A, r, Qt change synchronously, where r wave is surface wave. When the finger is beating on the upper surface of the defect, the L wave is beating synchronously. This is a longitudinal wave. The calculation is 20+20÷1.826×cos 45°=28 mm. This defect is a single pore with an aperture of 22−20=2 mm. (45° probe inspection, depth adjustment, the distance between the reflected wave and the surface wave is the aperture. If calculated, according to formula (4), D=A÷3.14÷1.08÷cos β×2.4, D=2÷3.14÷1.08÷cos 45°×2.4=2 mm. Two points of this defect can prove that the defect is a circular defect. First, there are longitudinal waves generated on the upper surface. The second point is that there are three Qt waves with approximately equal spacing, and each wave changes with the push and pull and twist of the probe.

2.2. Flat bottom hole (vertical detection surface) flaw inspection, as shown in FIG. 28-2, flat bottom hole (parallel to detection surface) flaw inspection, as shown in FIG. 28-3.

FIG. 28-2 and FIG. 28-3 are analyzed together. Pulse 1 is the reflected wave at point A, pulse 2 is the reflected wave at point B. The positions of the highest reflected waves at points A and B are the same in the horizontal position, and the difference in depth distance is the height of the defect. As shown in FIG. 28-2, the depth position is the same, and the horizontal distance difference is the length of the defect. As shown in FIG. 28-3, if the flat bottom hole becomes a through-hole, there is no reflection at point A in absence of point A. Since the sound beam is obliquely hitting the surface of the cylinder, the surface wave propagates in an elliptical trajectory. Pulse 3 is a diffracted wave at point c, and the reflected wave is low. Pulse 4 is the superposition of echoes generated when the two-way surface waves generated by the surface of the cylinder propagates to point D. Surface wave propagation conforms to Snell's law. Through the depth distance displayed by the surface wave on the instrument, check the corresponding aperture in the chart in FIG. 31, where the Y value represents the depth distance of the pulse 4 surface wave and X represents the corresponding aperture.

Regarding the calculation of the Y value, first finds the position indicated by the pulse 2 which is the highest reflected pulse at point B. After the determination, through push and pull of the probe to find the position of the highest reflected wave for the pulse 3. At this time, this position is the position of the highest reflected wave at point B. If it is not in this position, this reflected wave is not pulse 3. When the position of the highest reflected wave of Pulse 3 is fixed, pulse 2 has moved forward. At this time, the values of the pulse 2 and pulse 3 indicated by the instrument is the Y value. Regarding the surface wave generated by the endpoint A, after the sensitivity is increased, sometimes two pulses that are connected together may appear after pulse 2 and pulse 3, respectively. Surface waves can also be used to determine the length and diameter of the defect.

For all weld flaw inspections, in addition to the bottom wave reflected by the weld corners, other reflected, diffracted, and deformed waves of the weld corners are also regular, only depending on the angle of the probe and the shape of the weld corners and the grain size of the material, some waves appear, some waves do not appear, some have strong reflections, and some have weak reflections. For the purpose of weld flaw detection, all the reflected waves need to be analyzed. First, determine which waves are the normal reflected, diffracted, and deformed waves of the weld corners, and these waves should have independent and clear peaks. In addition to this, all other waves that appear would have their causes. For example, there is no defect wave that appears before the bottom wave, but there is a wave behind the bottom wave which is not a regular reflected wave, then this wave is a problematic wave. In another case, there is one defect reflected wave before the bottom wave and there is also an irregular reflected wave behind the bottom wave. For any wave to be assessed, 77+2Q echo analysis method can be used.

The use for flaw detection of the surface wave generated by the transverse wave oblique probe itself such as R1 shown in FIG. 25-8 and the surface wave R2 generated by the lower weld corner is illustrated in FIG. 29. To determine whether it is a surface wave, tap your finger in front of the probe, and if the reflected pulses bounce at the same time, determine that it is reflected wave of a surface defect. The level of the wave reflection is related to the size of the defect and the amount of coupling agent in front of the probe. Coupling agents can easily absorb surface waves. Surface waves produced by conventional 70° probes are relatively high. The smaller the angle is, the smaller the surface wave is generated. The 45° probe is so small that it does not affect the flaw detection. Regarding the assessment of the surface crack in the lower weld, use the finger as above if conditions permit. Generally, it is connected with the reflected wave of the weld corner, and it can be assessed by push pull and twist during analysis. If there is a defect under the skin of the sheet near the edge of the weld, it is called detecting the defect under the skin. As shown in FIG. 30, the reflected wave of the defect is in the initial pulse, and the Qt wave generated is easily misjudged as a defect in the weld. If it is misjudged, however many times of repair of the weld is in vain.

The reflection-diffraction-deformation flaw detection method with the transverse wave oblique probe according to the present which is mainly based on 45° probe flaw detection has the following advantages.

1. Weld flaw detection, full coverage of the acoustic path is achieved in the same thickness range, compared with the 60°, 70° probes, the 45° probe has the shortest travel distance, the highest sensitivity, the best near-surface defect resolution, and the strongest defect detection capability.

2. Use the reflection method for flaw detection to examine the reflection range of the 45° to 70° probes with respect to the defect surface. For circular defects, if we use probes covering all angles from 45° to 70° for flaw detection, then the primary-wave arc AB only covers about one-fifteenth of the circumference of the circle, as shown in FIG. 33-1.

If we use probes covering all angles from 35° to 85° for flaw detection, then the primary-wave still only covers about one-sixth of the circumference of the circle, as shown in FIG. 33-2.

For vertical plane defects, if you use a transverse wave probe at all angles for flaw detection, all found is the reflection at the upper endpoint and the diffraction at the lower endpoint. The plane-shape presents a total reflection, which the probe cannot receive, as shown in FIG. 34.

For other types of defects, probes at various angles only show wave heights for reflections in different parts of the defect. If an angle probe cannot detect a certain defect, there are only two cases one of which is that the sound wave fails to scan the defect, and the other is a low sensitivity.

3. For the flaw detection of a weld with a somewhat wide formation with a relatively thin plate, influenced by the length of the leading edge of the probe, it can be seen by plotting that if the sound path of the 45° probe does not reach the full coverage with a primary and secondary-wave flaw detection, and there are positions that cannot be scanned, then the tertiary wave is required to carry out the flaw detection.

4. The weld would generate tensile stress, compressive stress or alternating stress during the welding process. These stresses run through the entire welding process and a period of time after welding. Whether it is a butt weld or a corner weld, the cracks generated are more inclined at an angle of 45°, which is related to the 45° shear stress combined by various stresses. For cracks with an angle of inclination of 45°, using a 45° probe for flaw detection is the best choice, and it is not easy to miss detection (including longitudinal cracks and transverse cracks).

5. According to the law of conservation of energy, the more the wave mode conversion happens during the same sonic flaw detection process, the more the energy is decomposed, the more the sensitivity is reduced, and the more it is not conducive to finding defects. According to Snell's law, the 45° probe has less wave mode conversion than the 60° and 70° probes. For example, in the case of a vertical plane defect, when 45° sound waves hit the defect plane a total reflection will occur, and when 60°, 70° sound waves hit the defect surface, then in addition to generating transverse wave reflection, a deformed longitudinal wave is generated, which reduces the energy of the reflected transverse wave. Not all waves can be received by the probe.

6. Under the same sensitivity, check the distance amplitude curve of the probes at the three angles. 45° probe produces the highest curve, 60° the second, 70° probe has the lowest. The reason for the highest is that with the probes of the three angles detecting the same defect, the 45° has the shortest sound path, and the 70° has the longest sound path. However, in actual flaw detection process, when the weld groove angle is at 20° and 30°, for the defect that is present in such weld, the reflected wave height in flaw detection with 45° is sometimes lower than the reflected wave height in flaw detection with 60° and 70° probes. One of the reasons is that the shape and angle of the defect in the weld is to a degree related to the groove bevel angle, and has a certain relationship with the welding form and welding method. If only the reflected wave height of the defect is used for quantification, then the probe can only be selected according to the condition of the weld. The flaw detection with the reflection-diffraction-deformation method doesn't select the probe depending on the conditions of the weld, only the 45° probe is used for flaw detection, and the quantification is not based on the reflected wave height, and the distance wave amplitude curve is only a reference.

7. In flaw detection of a plate with the transverse wave oblique probe, there is no reflection other than the reflection at the edge of the plate. If there is reflection, it is only a defect, and the flaw detection is very easy. If there are welds on the top and bottom of the plate, the surface connecting the weld to the plate is an R angle. This formation results in increased reflection, and reflected waves and deformed waves (deformed longitudinal waves and surface waves) in different directions. But however many of these waves there are, they are all regular, the existence of these reflected waves depends on the size of the R angle and the presence or absence of it. Not for every weld, these waves must appear every time. Sometimes one, sometimes two, sometimes three or more, but they are very regular. And there is only one peak, more would be problematic. The reflected waves appearing other than this, as long as they appear on the screen, have their causes, which should be analyzed. The defects near the upper and lower surfaces of the weld mentioned above are connected to or close to the primary or secondary bottom wave, which makes the bottom wave wider and more peaks. These are abnormal reflections and must be taken seriously.

8. For weld flaw inspection, the anisotropy of the plate and the grain size of the weld will change the flaw inspection sensitivity and probe refraction angle. This change directly affects the precise positioning of the defect and the determination of eligibility. The reflection method relies on the test block for adjustment, and the instrument can only serve as a reference, because the anisotropy difference of each plate is different. One test block cannot represent the changes in the flaw inspection of all plates and welds. Especially for TMCP steel, the anisotropy is particularly obvious. Even if the plates have the same chemical composition, performance and size, the anisotropy difference is different. For transverse wave flaw detection, the thicker the plate, the more severe the anisotropy. The larger the probe angle, the greater the change in angle and sensitivity caused by the anisotropy of the material. The smaller the probe angle, the smaller the change in angle and sensitivity. There is no difference in the 0° probe angle, and the sensitivity is slightly different. Compared with the 60° and 70° probes, the 45° probe has a small difference in anisotropy in flaw detection, which can reach an acceptable level, the refraction angle changes within three degrees, and the sensitivity changes within 15%. The 45° probe reflection-diffraction-deformation method does not consider anisotropy including TMCP steel.

9. Compared with probes of other angles, when the wafer size is the same, the 45° probe has a shorter leading edge, which is also beneficial for flaw detection.

10. For flaw detection of the same weld, the short sound path of 45° can increase the frequency of the probe, so that the ability to find defects increases, the pulse width becomes narrower, the blind zone is smaller, and the resolution of the defect is increased. (Influence of noise wave and attenuation should be considered).

11. For 45° transverse wave oblique probe, the endpoint reflection, diffraction and deformation functions are higher than 60° and 70° probes.

12. In addition to weld flaw detection, the 45° transverse wave oblique probe can also replace the normal probe for flaw detection on many products. For primary-wave flaw detection on one surface with longitudinal wave, regarding the defect, no matter how the probe moves, it is the same defect surface that is detected, and there are requirements for the bottom wave. But for the flaw detection with the transverse wave reflection-diffraction-deformation method, the primary-wave flaw detection on one surface can comprehensively express the defect.

13. The 45° probe can cover a large detection range for detecting workpieces and welds with curved shapes. Defect assessment can be performed by reversed thinking, with the detection surface as a flat surface and the defect as a curved surface. Curved surface flaw detection is more likely to produce deformed waves, and even 45° probe flaw detection is inseparable from plotting analysis.

14. For any product that uses a normal probe for flaw detection, if it is possible to use the 45° transverse wave oblique probe for flaw detection, the accuracy would be higher than the flaw detection with normal probe. This is because the transverse wave reflection-diffraction-deformation flaw detection method can detect the shape of the defect. For example, in the case of flaw detection of a plate, the normal probe flaw detection only discovers the delamination, while for other defects in the plate such as interlayer cracks and impurities and so on, one case is that they can easily miss the detection, the second case is that they cannot be detected. Furthermore, only the position walked by the probe is the detected position. When the probe doesn't reach the defect, the defect cannot be detected. If the 45° transverse wave probe is used instead, the probe only needs to travel one circle around the edge of the plate or walk by area according to the size of the plate, the full coverage detection of the plate can be achieved. For the defects that can be or cannot be detected by the normal probe, the 45° transverse wave oblique probe can all well detect, and the defects can be rendered three-dimensionally.

Finally, it should be noted that the foregoing embodiments are merely used to illustrate but not to limit the technical solutions of the present disclosure. Although the present disclosure has been described in detail in connection with the foregoing embodiments, those having ordinary skill in the art shall understand that it is possible to modify the technical solutions described in the foregoing embodiments, or to substitute some or all of the technical features equivalently. And these modifications or substitutions do not render the essence of the corresponding technical solutions to depart from the scope of the technical solutions of various embodiments of the present disclosure.

What is claimed is:

1. A weld flaw detection method using a transverse wave oblique probe, comprising the following steps:
- S1: determining a flaw detection sensitivity based on a grain size of the weld;
- S2: transmitting a pulse of ultrasonic wave to the weld from a traverse wave oblique probe of and generating a reflected wave, a diffracted wave, and a deformed wave upon detecting a defect;
- S3: determining a type and a size of the defect by the deformed wave having deformed characteristics wherein the deformed surface wave at an endpoint of the defect propagates on a surface of the defect, wherein the defect is a plane defect, a circular defect, a semicircular defect, or a polygonal defect;
- S4: determining a length of the defect using a 6 dB drop method when the reflected, diffracted, and deformed waves to the endpoint are the same; and
- S5: positioning the defect, wherein the positioning starts from identifying the end point by the reflected wave.

2. The flaw detection method according to claim 1, wherein in step S3,
- the plane defect is parallel to a detection surface, is perpendicular to the detection surface, is inclined from being perpendicular to the detection surface toward to the probe, or is inclined from being perpendicular to the detection surface to away from the probe side,
- wherein the circular or the semi-circular defect is a spherical air hole, a transverse through-hole, a flat-bottom hole, or a semi-circular defect, and
- wherein the polygonal defect is a triangular defect, a quadrilateral defect, or a hexagonal defect.

3. The flaw detection method according to claim 1, wherein
- in step S4,
- when the reflected, diffracted, and deformed waves to the endpoint are different, indicating the defect is irregular in a longitudinal direction, moving the probe horizontally away from the end point until the reflected, diffracted, and deformed waves disappear, and then rotating the probe is tilted 15°-45° toward the defect to generate the reflected, diffracted, and deformed waves for positioning the end point.

4. The flaw detection method according to claim 3, further comprising analyzing reflected waves and deformed waves generated by weld corners to evaluate the quality of formation of the weld and to determine the presence or absence of defects on the surface and near-surface of the weld, with a first assumption that a reflected wave appearing in front of the reflected wave of the weld corner is determined as a reflected wave of the defect, a wave appearing after the reflected wave of the weld corner is not considered in the analysis, and with a second assumption that an irregular wave appearing after the reflected wave of the weld corner is considered to be from a defect with all the waves appearing on the scanning line are analyzed.

5. The flaw detection method according to claim 1, wherein
- the endpoint of the defect generates a surface wave that propagates along the surface of the defect, and generates the reflected wave upon encountering a corner, wherein the size of the surface of the defect is calculated based on the position of the reflected wave; and
- wherein, the surface wave continues to propagate around a polyhedron a full cycle to generate circumferential echoes, which is used to determine the shape of the defect.

6. The flaw detection method according to claim 4, wherein
- the reflected wave, diffracted wave, and deformed wave from the defect, together with the reflected waves from the weld corners, form reflection loop, wherein the reflection loop is mapped or programmed into software to confirm the generation of each reflected echo appearing on the weld flaw detection screen; and
- determining the shape of the defect according to confirmed data.

7. The flaw detection method according to claim 6, wherein
- the reflected waves with different sound velocities and generated by different paths on the screen are processed by software and displayed in different colors, wherein a normal transverse wave is assigned a first color, a longitudinal wave assigned a second color, a surface wave is assigned a third color, a longitudinal wave deformed from a transverse wave is assigned a fourth color, a transverse wave deformed from a longitudinal wave is assigned a fifth color; and a surface wave deformed from a transverse wave is assigned a sixth color, a longitudinal wave deformed from a surface wave is assigned a seventh color, and a transverse wave deformed from a surface wave is assigned an eight color.

8. The flaw detection method according to claim 1, wherein
- plurality of pulses of ultrasonic wave are processed by software to appear in a line to minimize a width of a blind area and increase resolution.

* * * * *